(12) United States Patent
Plummer et al.

(10) Patent No.: US 9,849,494 B2
(45) Date of Patent: Dec. 26, 2017

(54) AUTOMATED BENDER AND SYSTEMS AND METHODS FOR PROVIDING DATA TO OPERATE AN AUTOMATED BENDER

(71) Applicant: Greenlee Textron Inc., Rockford, IL (US)

(72) Inventors: Jeffrey Plummer, Rockford, IL (US); Sean Daugherty, Gilberts, IL (US); Ryan Mantell, Woodstock, IL (US); Gerald Tully, Wuppertal (DE)

(73) Assignee: TEXTRON INNOVATIONS INC., Rockford, IL (US)

( * ) Notice: Subject to any disclaimer, the term of this patent is extended or adjusted under 35 U.S.C. 154(b) by 671 days.

(21) Appl. No.: 14/541,541

(22) Filed: Nov. 14, 2014

(65) Prior Publication Data
US 2015/0135793 A1 May 21, 2015

Related U.S. Application Data

(60) Provisional application No. 61/904,588, filed on Nov. 15, 2013, provisional application No. 62/045,867, filed on Sep. 4, 2014.

(51) Int. Cl.
*B21D 7/024* (2006.01)
*B21D 7/12* (2006.01)
(Continued)

(52) U.S. Cl.
CPC ............... *B21D 7/12* (2013.01); *B21D 7/021* (2013.01); *B21D 7/024* (2013.01); *B21D 7/04* (2013.01);
(Continued)

(58) Field of Classification Search
CPC . B21D 7/12; B21D 7/04; B21D 7/021; B21D 7/024; B21D 7/10; B21D 11/22; G05B 19/402
(Continued)

(56) References Cited

U.S. PATENT DOCUMENTS 2,817,384 A  12/1957  Mabery
4,180,997 A  1/1980  Evenson
(Continued)

FOREIGN PATENT DOCUMENTS

DE  102008047542 A1  3/2010
EP  01202336  10/1984
(Continued)

OTHER PUBLICATIONS http://www.startechnologysrl.it/eng/software.html, 3 pages.
(Continued)

*Primary Examiner* — David B Jones
(74) *Attorney, Agent, or Firm* — Klintworth & Rozenblat IP LLP

(57) ABSTRACT

An automated bender and its method of operation according to some embodiments of the disclosure is provided. The automated bender includes a carousel which has all of the necessary components for bending a variety of conduit sizes provided thereon. The carousel can be rotated to a desired bending position to bend a particular type of conduit. A straight workpiece is fed into the automated bender and a bent workpiece, which may have multiple bends therein, is output from the automated bender. This bending process is performed without manual intervention. Software for achieving same is provided.

28 Claims, 36 Drawing Sheets

(51) Int. Cl.
- B21D 7/04 (2006.01)
- B21D 7/10 (2006.01)
- B21D 11/22 (2006.01)
- G05B 19/402 (2006.01)
- B21D 7/02 (2006.01)

(52) U.S. Cl.
CPC .............. *B21D 7/10* (2013.01); *B21D 11/22* (2013.01); *G05B 19/402* (2013.01)

(58) Field of Classification Search
USPC .......................................................... 72/306
See application file for complete search history.

(56) References Cited

U.S. PATENT DOCUMENTS

| | | | |
|---|---|---|---|
| 4,403,496 A | 9/1983 | Kowal | |
| 4,624,466 A | 11/1986 | Steinberger | |
| 4,843,859 A | 7/1989 | Togoshi | |
| 5,499,522 A * | 3/1996 | Schwarze | B21D 7/021 72/149 |
| 5,987,958 A | 11/1999 | Moore, Jr. et al. | |
| 6,038,903 A | 3/2000 | Traub | |
| 6,152,435 A | 11/2000 | Snell | |
| 6,757,576 B2 | 6/2004 | Greer et al. | |
| 7,024,903 B2 * | 4/2006 | Schmauder | B21D 7/021 72/149 |
| 7,172,186 B2 | 2/2007 | Saito et al. | |
| 7,213,478 B2 | 5/2007 | Harada et al. | |
| 7,254,972 B1 * | 8/2007 | Wang | B21D 7/021 72/149 |
| 7,305,274 B2 | 12/2007 | Greer et al. | |
| 8,443,644 B2 | 5/2013 | Wolf | |
| 2002/0104361 A1 | 8/2002 | Broggi et al. | |
| 2003/0080267 A1 | 5/2003 | Eslick | |
| 2004/0065131 A1 | 4/2004 | Schmauder et al. | |
| 2004/0251608 A1 | 12/2004 | Saito et al. | |
| 2005/0015176 A1 | 1/2005 | Harada et al. | |
| 2008/0107490 A1 | 5/2008 | Hughes | |
| 2010/0130106 A1 | 5/2010 | Hyatt et al. | |
| 2010/0180653 A1 | 7/2010 | Wolf | |
| 2011/0100160 A1 | 5/2011 | Petrescu et al. | |
| 2012/0243954 A1 | 9/2012 | Rusch | |
| 2012/0303149 A1 | 11/2012 | Bollendorf | |

FOREIGN PATENT DOCUMENTS

| | | |
|---|---|---|
| EP | 0200979 | 11/1986 |
| EP | 1396295 | 3/2004 |
| WO | 96/24445 A | 8/1996 |
| WO | 2009/135845 | 11/2009 |

OTHER PUBLICATIONS http://metal.baileighindustrial.com/metalworking/mandrel—benders, 3 pages.
http://metal.baileighindustrial.com/mandrel—tubebender—mb—80—cnc, 2 pages.
http://metal.baileighindustrial.com/mb—nce1, 2 pages.
http://metal.baileighindustrial.com/mandrelbenders—mb—nch—2—series, 2 pages.
http://www.blmgroup.com/en/products/bending.aspx, 2 pages.
http://www.blmgroup.com/en/products/bending/tube/elect—xl.aspx, 1 page.
http://www.hornmachinetools.com/, 3 pages.
http://www.addisonmckee.com/benders, 2 pages.
http://www.eatonleonard.com/mainpages/cnc—tube—bending—machines.html, 1 page.
http://youtu.be/ayPD5s4uiXM, uploaded by BillaVista on Sep. 29, 2009.
http://youtu.be/5SFs4O64RIE, uploaded by JaimeeJD2 on Feb. 14, 2011.
http://youtu.be/yigRgG_NlyU, uploaded by COONEYMARINE1's channel on Jun. 22, 2010.
http://youtu.be/vglQqs1f6XM, uploaded by GRBInnovations's channel on Mar. 9, 2012.
http://youtu.be/uYc_r5igaWQ, uploaded by Ahmet Ozer on Mar. 31, 2013.
http://youtu.be/pOcqZQAmMgU, uploaded by TRACTO-TECHNIK GmbH & Co. KG on Jul. 26, 2011.
http://youtu.be/Mrbs—17rfxw, uploaded by BaileighIndustrial on Dec. 22, 2011.
http://youtu.be/O2VilX74X0o, uploaded by GTMPOWER on Aug. 2, 2013.
Instructional Manual for 854 Quad Bender, 2007 Greenlee Textron Inc., 25 pages.
International Search Report and Written Opinion for PCT/US2014/65678 dated Mar. 23, 2015, 12 pages.
International Search Report and Written Opinion for PCT/US14/65673 dated Mar. 13, 2015, 11 pages.
Gupta et al. "Automated Process Planning for Sheet Metal Bending Operations," CMU research showcase, 1998, pp. 1-35.
Office Action from corresponding Chinese Patent Application No. 201480062357.0 dated Jun. 20, 2017, 12 pages.
English Translation of Office Action from corresponding Chinese Patent Application No. 201480062357.0 dated Jun. 20, 2017, 15 pages.
Partial Supplementary European Search Report from European Application No. 14862980.1, dated Oct. 2, 2017, 11 pages.
Machine translation for EP 0120336.
Machine translation for EP 0200979.
Machine translation for EP 1396295.
Office Action from U.S. Appl. No. 14/541,565, dated Jul. 27, 2017.

* cited by examiner

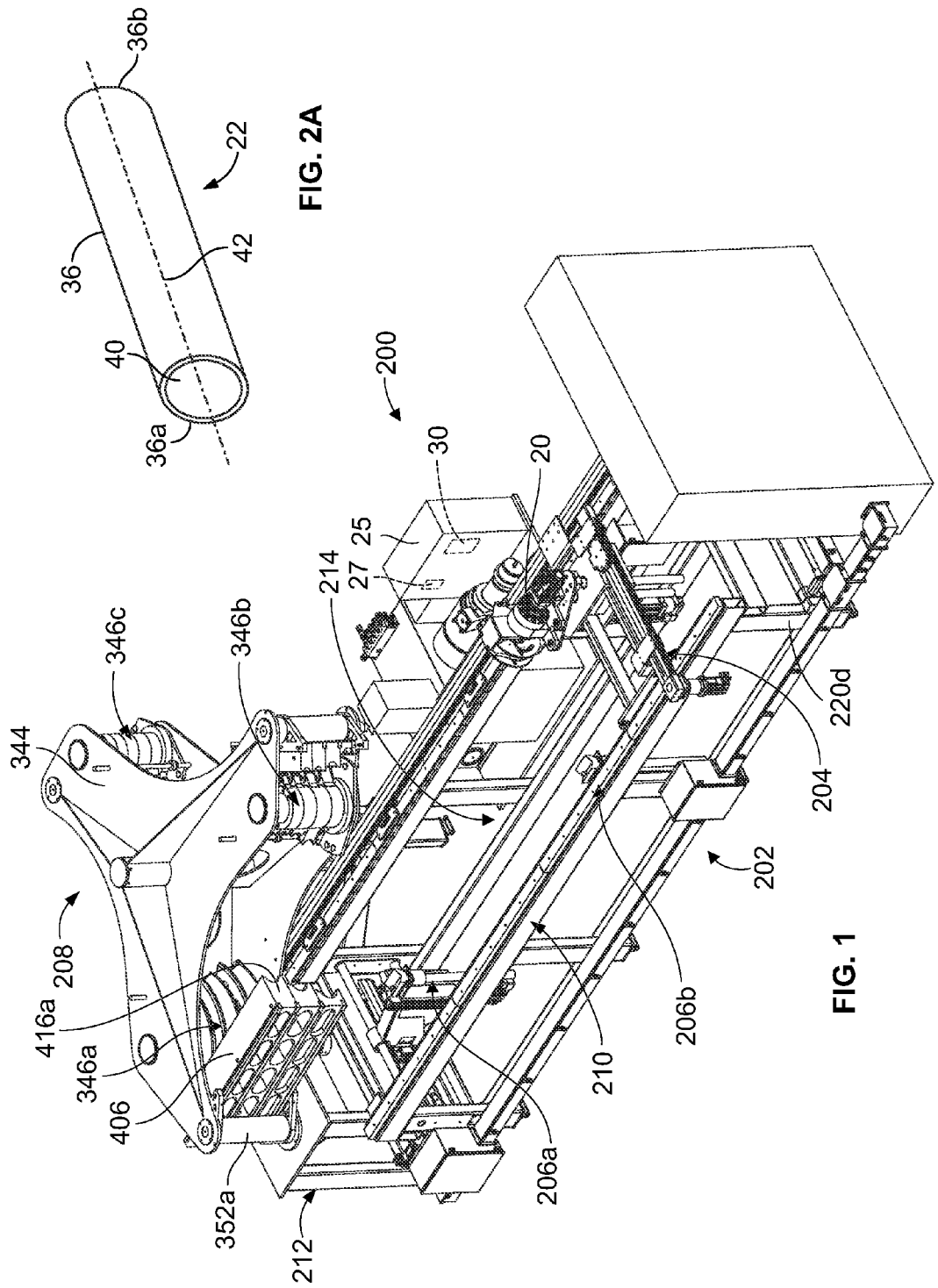

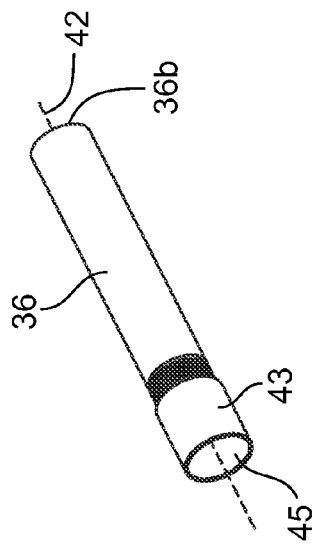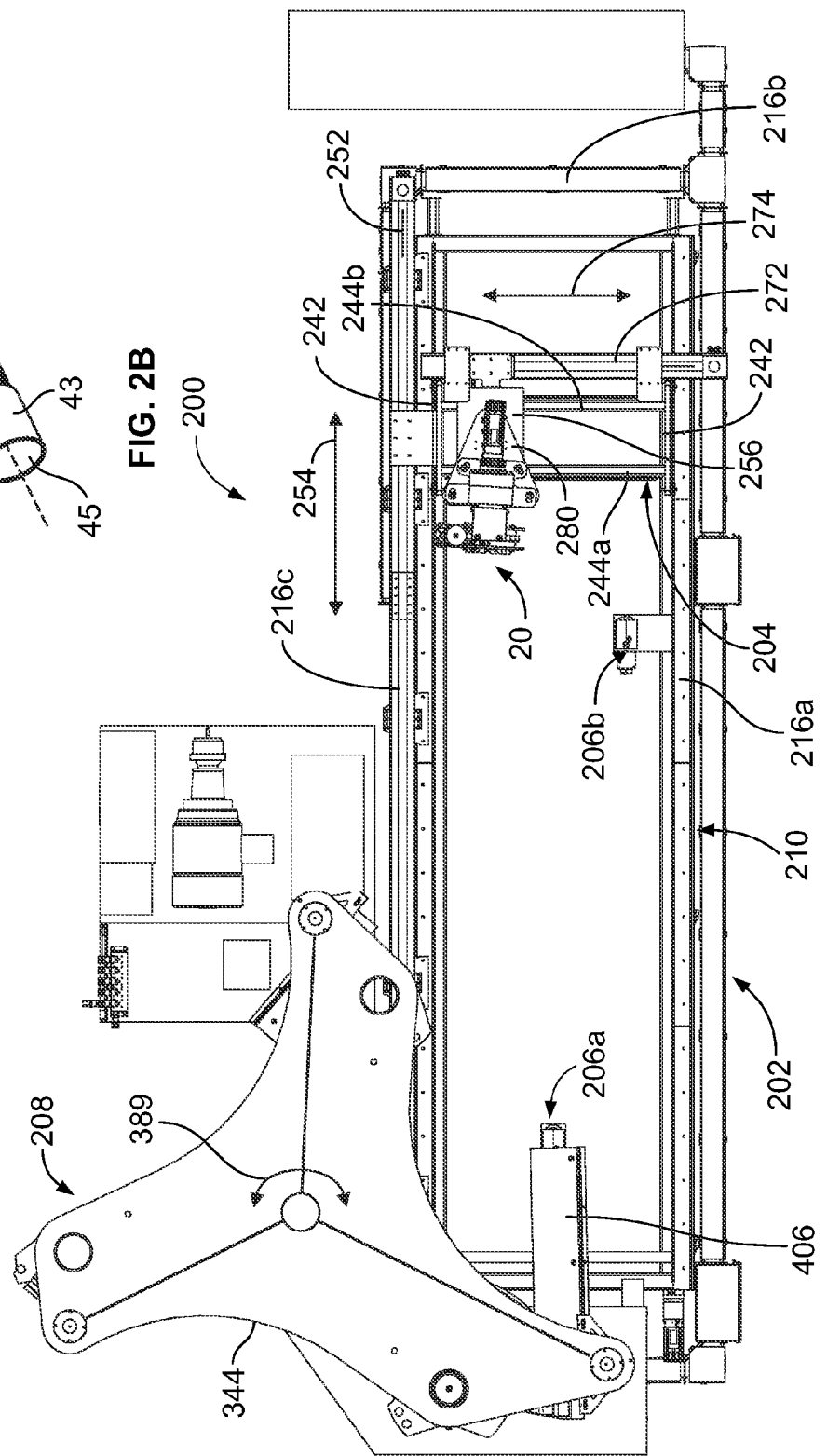

FIG. 41

| | | | | |
|---|---|---|---|---|
| 1102 — vers | AUTOMATED BENDER | | | |
| | 2013 | | | |
| 1104 — units | ENG | | | |
| 1106 — bendtype | SEQUENT | | | |
| 1108 — pipetype | EMT | | | |
| 1110 — pipesize | 100 | | | |
| 1112 — height | 0 | | | |
| 1114 — length | 0 | | | |
| 1116 — angle | 0 | | | |
| 1118 — straight | 0 | | | |
| 1120 — h1 | 0 | | | |
| 1122 — h2 | 0 | | | |
| 1124 — vangle | 0 | | | |
| 1126 — pipe_num | SEAN_0000 | SEAN_0001 | SEAN_0002 | |
| 1128 — seq_bends | 5 | | | |
| 1130 — l1_a1 | 6 | 15 | | |
| 1132 — l2_a2 | 18 | 30 | | |
| 1134 — l3_a3 | 42 | 15 | | |
| 1136 — l4_a4 | 60 | 45 | | |
| 1138 — l5_a5 | 80 | 90 | | |
| 1140 — conc_bend | 0 | | | |
| 1142 — conc_angle | 0 | | | |
| 1144 — conc_start | 0 | | | |
| 1146 — conc_radi | 0 | | | |
| 1148 — PI_batch | 10.125 | 0 | | |

FIG. 44

AUTOMATED BENDER AND SYSTEMS AND METHODS FOR PROVIDING DATA TO OPERATE AN AUTOMATED BENDER

This application claims the domestic priority of U.S. Provisional application Ser. No. 61/904,588, filed on Nov. 15, 2013 and U.S. Provisional application Ser. No. 62/045,867 filed on Sep. 4, 2014, the disclosure of each provisional application is incorporated by reference herein in its entirety.

FIELD OF THE DISCLOSURE

The present invention relates to an automated bender that is used to clamp a workpiece, such as a tube, pipe or conduit, rotate the workpiece so that the workpiece can be properly positioned for a bending operation, and bend the workpiece, and to systems and methods for providing data to operate the automated bender.

BACKGROUND

There are several prior methods of clamping and rotating tubing, pipe and conduit. A first method is that the user manually installs the proper size mandrel or collets to secure the tubing, pipe or conduit which is then manually fed into the bending machine. The user must also manually rotate for alternative bends on the same piece of tubing, pipe or conduit. Another method is that the user manually installs the proper size mandrel or collets to secure the tubing, pipe or conduit which is then automatically fed into the bending machine. All prior methods consisted of either having no rotation of the workpiece, manual rotation of the workpiece or the workpiece was automatically rotated using motors, geared motors, or a form of hydraulic or pneumatic actuation.

Current tube, pipe and conduit benders have collets and mandrels that have to be changed whenever a new diameter (inner diameter or outer diameter) tube, pipe or conduit is used. This becomes very costly to obtain and store numerous sizes of collets and mandrels.

In addition, currently architects create drawings and the drawings get passed to the electrical contractors. The electrical contractors then either print the drawings and take them to the field to bend conduit as needed to be installed based on the print, or they spend time creating individual drawings to pass them in a form that the individual contractor's prefabrication shop uses to create the bent conduit. This method is time consuming.

SUMMARY

An automated bender in accordance with some example embodiments includes a carousel which has all of the necessary components for bending a variety of conduit sizes provided thereon. The carousel can be rotated to a desired bending position to bend a particular type of conduit. A straight workpiece is fed into the automated bender and a bent workpiece, which may have multiple bends therein, is output from the automated bender. This bending process is performed without manual intervention. Software for achieving same is provided.

An automated bender in accordance with some example embodiments includes a carousel; and at least two bending shoes attached to the carousel, each the bending shoe having a plurality of channels therein into which the workpiece can be seated, each the bending shoe being rotatable relative to the carousel, each the bending shoe being rotatable independently of the other bending shoes.

An automated bender in accordance with some example embodiments includes a mounting frame; a carousel rotatably mounted on the mounting frame; at least first and second bending shoes attached to the carousel, each the bending shoe having a plurality of channels therein into which the workpiece can be seated, each the bending shoe being rotatable relative to the carousel, each the bending shoe being rotatable independently of the other bending shoes; a first follower bar attached to the carousel and moveable relative to the first bending shoe, the first follower bar having a plurality of channels therein into which the workpiece can be seated, wherein in use the workpiece is capable of being positioned between the first bending shoe and the first follower bar; a second follower bar attached to the carousel and moveable relative to the second bending shoe, the second follower bar having a plurality of channels therein into which the workpiece can be seated, wherein in use the workpiece is capable of being positioned between the second bending shoe and the second follower bar; and a motor attached to the mounting frame, wherein when the carousel is rotated, one of the bending shoes engages with the motor.

An automated bender in accordance with some example embodiments includes a mounting frame; a carousel rotatably mounted on the mounting frame; first and second bending shoes attached to the carousel, each the bending shoe having a plurality of channels therein into which the workpiece can be seated, each the bending shoe being rotatable relative to the carousel, each the bending shoe being rotatable independently of the other bending shoes; a first follower bar attached to the carousel and moveable relative to the first bending shoe, the first follower bar having a plurality of channels therein into which the workpiece can be seated, wherein in use the workpiece is capable of being positioned between the first bending shoe and the first follower bar; a second follower bar attached to the carousel and moveable relative to the second bending shoe, the second follower bar having a plurality of channels therein into which the workpiece can be seated, wherein in use the workpiece is capable of being positioned between the second bending shoe and the second follower bar; a clamping apparatus mounted on the mounting frame and which is capable of holding an end of the workpiece, the clamping apparatus being movable relative to the mounting frame and to the carousel for engaging an opposite end of the workpiece with one of the bending shoes; and a seat mounted on the mounting frame and which is capable of holding a portion of the workpiece, the seat being positioned between the clamping apparatus and the carousel, the seat is capable of movement relative to the clamping apparatus, and is capable of movement with the clamping apparatus.

A computer-implemented method of operating a bender in accordance with some example embodiments includes seating a workpiece on at least one seat; moving the workpiece toward a clamping apparatus; engaging an end of the workpiece with the clamping apparatus; engaging an opposite end of the workpiece with a bending shoe; moving the workpiece using the clamping apparatus to position the workpiece at a position wherein a bend is to be effected in the workpiece; and bending the workpiece, wherein the method is performed under control of at least one processor.

An automated bender in accordance with some example embodiments includes a clamping apparatus configured to hold a workpiece; a carousel mounted with the clamping apparatus, the clamping apparatus configured to move the workpiece to the carousel based on data, the data being determined at least in part from an architectural drawing by a processor; and a shoe and a follower bar mounted on the carousel, the clamping apparatus configured to move the workpiece between the shoe and the follower bar to create a desired bend in the workpiece based on the data.

An apparatus in accordance with some example embodiments includes at least one memory storing computer program code; and at least one processor configured to execute the computer program code, wherein the computer program code comprises instructions, which when executed by the at least one processor, cause the at least one processor to control an automated bender to at least: introduce a workpiece into a channel of a follower bar of the automated bender; advance the workpiece via the channel through a shoe assembly; position a shoe of the shoe assembly at a determined location of the workpiece to bend the workpiece; and rotate the shoe to bend the workpiece between the shoe and the follower bar.

A computer-readable medium includes code which when executed by a processor causes the processor to determine data for bending a workpiece from an architectural drawing, and export the data for being inputted to an automated bender, the automated bender configured to bend the workpiece loaded to the automated bender based on the data.

This Summary is provided merely for purposes of summarizing some example embodiments so as to provide a basic understanding of some aspects of the disclosure. Accordingly, it will be appreciated that the above described example embodiments are merely examples and should not be construed to narrow the scope or spirit of the disclosure in any way. Other embodiments, aspects, and advantages of various disclosed embodiments will become apparent from the following detailed description taken in conjunction with the accompanying drawings which illustrate, by way of example, the principles of the described embodiments.

BRIEF DESCRIPTION OF THE DRAWINGS

The organization and manner of the structure and operation of the disclosed embodiments, together with further objects and advantages thereof, may best be understood by reference to the following description, taken in connection with the accompanying drawings, which are not necessarily drawn to scale, wherein like reference numerals identify like elements in which:

FIG. 1 is a perspective view of an automated bender which incorporates the features of some example embodiments;

FIG. 2A is a perspective view of workpiece which may be bent by the automated bender of FIG. 1;

FIG. 2B is a perspective view of alternate workpiece which may be bent by the automated bender of FIG. 1;

FIG. 3 is a top plan view of the automated bender;

FIG. 41 is a screenshot of an example BIM drawing;

FIG. 44 is a table of an example CSV output file.

DETAILED DESCRIPTION OF THE ILLUSTRATED EMBODIMENTS

Figure 4:
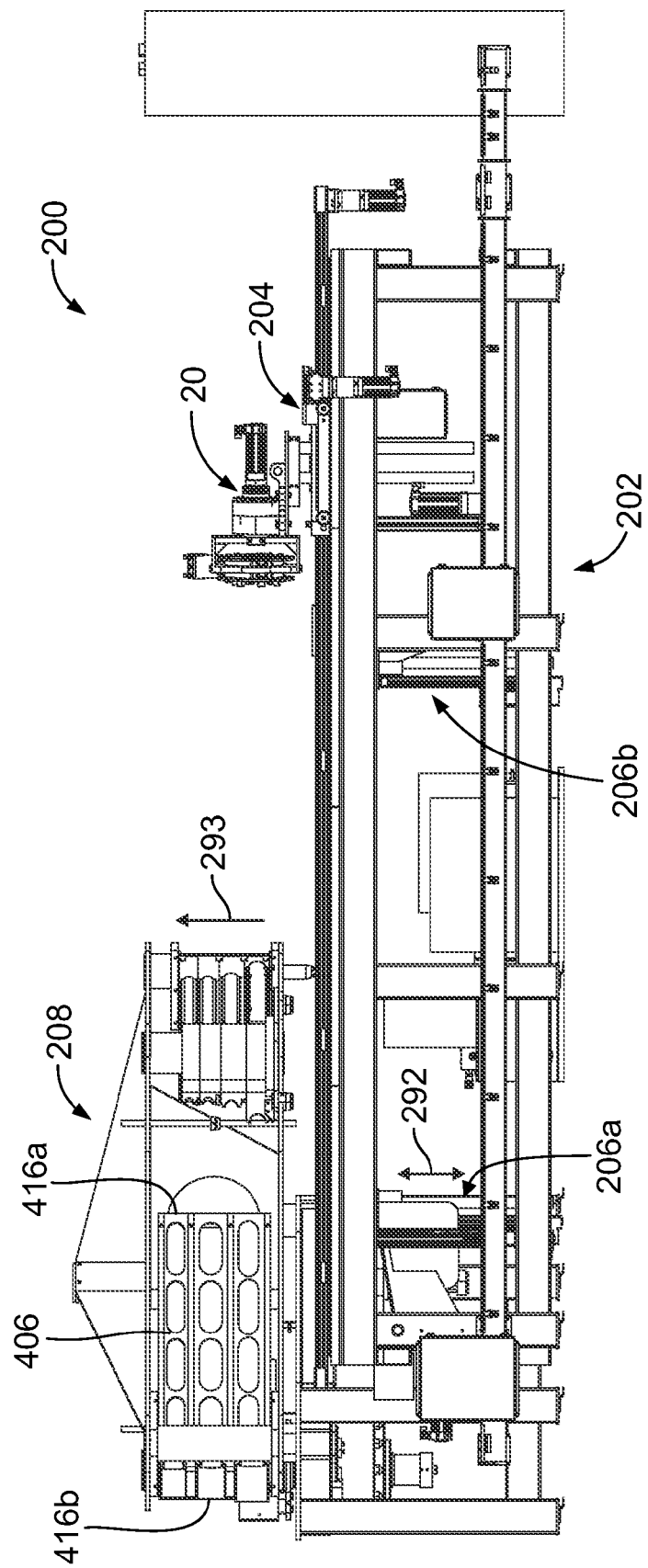
FIG. 4 is a side elevation view of the automated bender.
Figure 5:
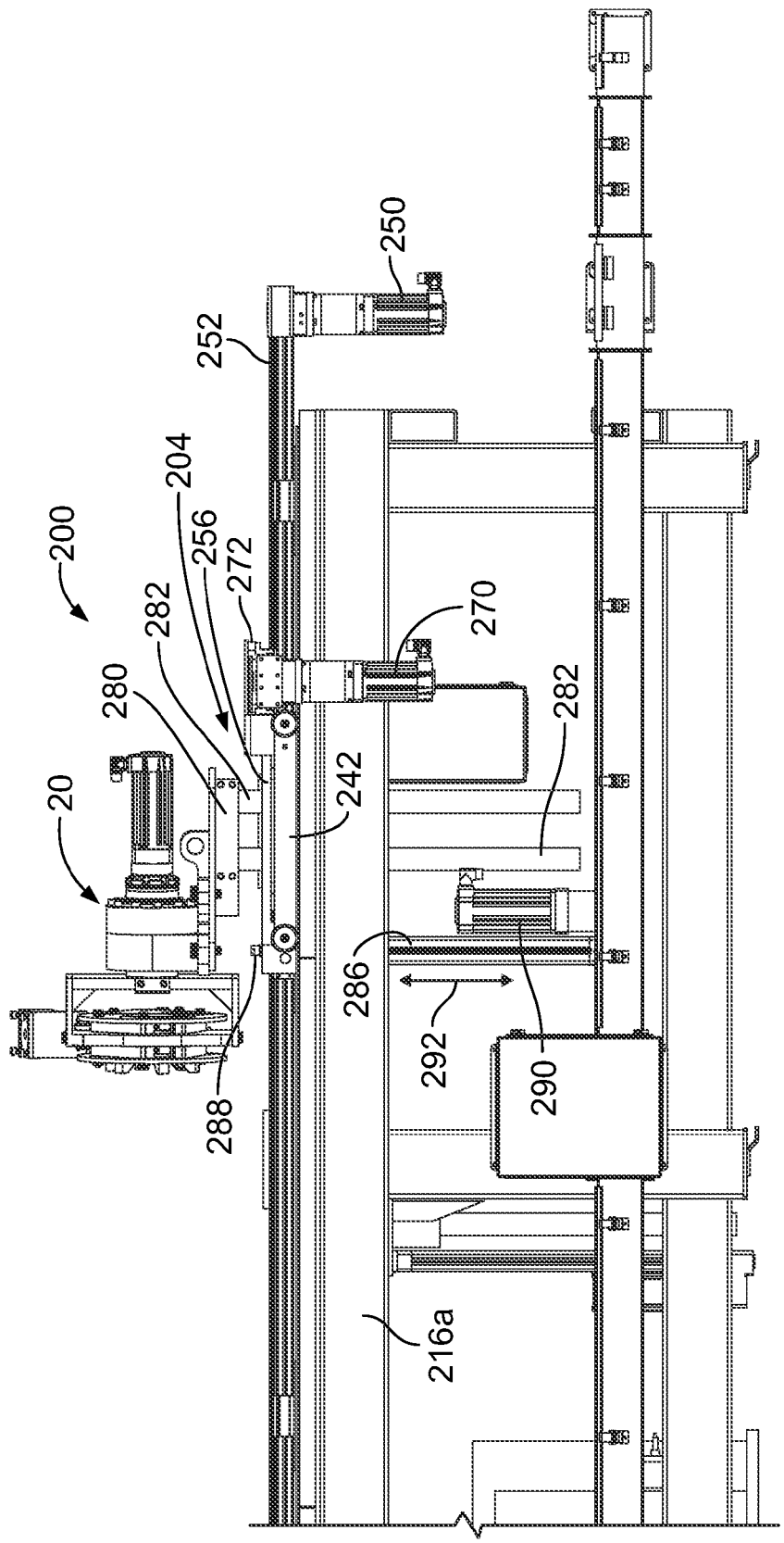
FIG. 5 is another side elevation view of a portion of the automated bender.

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein. Therefore, unless otherwise noted, features disclosed herein may be combined together to form additional combinations that were not otherwise shown for purposes of brevity. It will be further appreciated that in some embodiments, one or more elements illustrated by way of example in a drawing(s) may be eliminated and/or substituted with alternative embodiments within the scope of the disclosure.

An automated bender 200 is provided which is used to clamp a workpiece 22, such as a tube, pipe or conduit, to rotate the workpiece 22 so that the workpiece 22 can be properly positioned for a bending operation, and bend the workpiece 22.

The automated bender 200 allows for the fabrication of workpieces based data that is automatically extracted from architectural drawing models using an application 901, which may, for example, be implemented as a plug-in application. The architectural drawing models include building information modeling (BIM) drawings. The BIM drawings may be produced by software used by architects, structural engineers, mechanical, electrical and plumbing (MEP) engineers, designers and contractors, etc. Example types of BIM software include AUTODESK REVIT, BENTLY and other BIM applications. The applications, and any of the software described herein, may be implemented by hardware, software or firmware, or a combination thereof, and may be stored locally, embodied in the form of a portable computer-readable medium and code, and/or distributed over a network, etc.

The workpiece 22 to be bent may include any typical workpiece 22, e.g., having an outer diameter between about 0.5" and 7", which is to be bent into a defined shape having one or more bends in the workpiece 22. As shown in FIG. 2A, the workpiece 22 has a body having front end 36a, and an opposite rear end 36b which defines a length therebetween, and a sidewall 36 which may have a central passageway 40 therethrough. The workpiece 22 has a longitudinal axis or centerline 42. The sidewall 38 may take a variety of cross-sectional shapes, such as for example, but not limited to, circular, rectangular, square, hexagonal. The workpiece 22 is preferably made of metal, but could be another solid bendable material. While the workpiece 22 is generally shown and described herein as being a tube, pipe or conduit, it should be understood that the workpiece 22 could take other forms and shapes, such as a solid rod. In some embodiments, the workpiece 22 may have a connection coupling 43 provided on the front end 36a as shown in FIG. 2B. The connection coupling 43 has a central passageway 45 which aligns with a central passageway 40, and may be threadedly attached to the body.

As shown in FIG. 1, the automated bender 200 generally includes a mounting frame 202, a clamping apparatus 20 mounted on a carriage assembly 204 which is in turn mounted to the mounting frame 202, a workpiece holding apparatus formed of a first assembly 206a mounted on the mounting frame 202 and a second assembly 206b mounted on the mounting frame 202, a bending carousel apparatus 208 mounted on the mounting frame 202, and a control device 25, which may be at least partially mounted on the mounting frame 202, and/or may be at least partially mounted a remote location to the mounting frame 202. For example, the control device 25 may include one or more computing devices that may be mounted to the mounting frame 202 and/or may include one or more computing devices that may be disposed remotely from the mounting frame 202, but that may be communicatively coupled to the automated bender 200, such as through a wireless and/or wireline communication link. The mounting frame 202 is seated on a stationary surface, such as a floor of a building or the floor of a mobile work unit such as a semi-trailer.

As shown in the embodiment of the invention shown generally in FIGS. 1-32, the mounting frame 202 includes a first frame assembly 210 and a second frame assembly 212. The clamping apparatus 20 and the first and second assemblies 206a, 206b forming the workpiece holding apparatus are mounted on the first frame assembly 210. The bending carousel apparatus 208 is mounted on the second frame assembly 212. It is to be understood that the design of the mounting frame 202 is not limited to two separate assemblies, and may be formed of a single assembly, or more than two assemblies.

Figure 6:
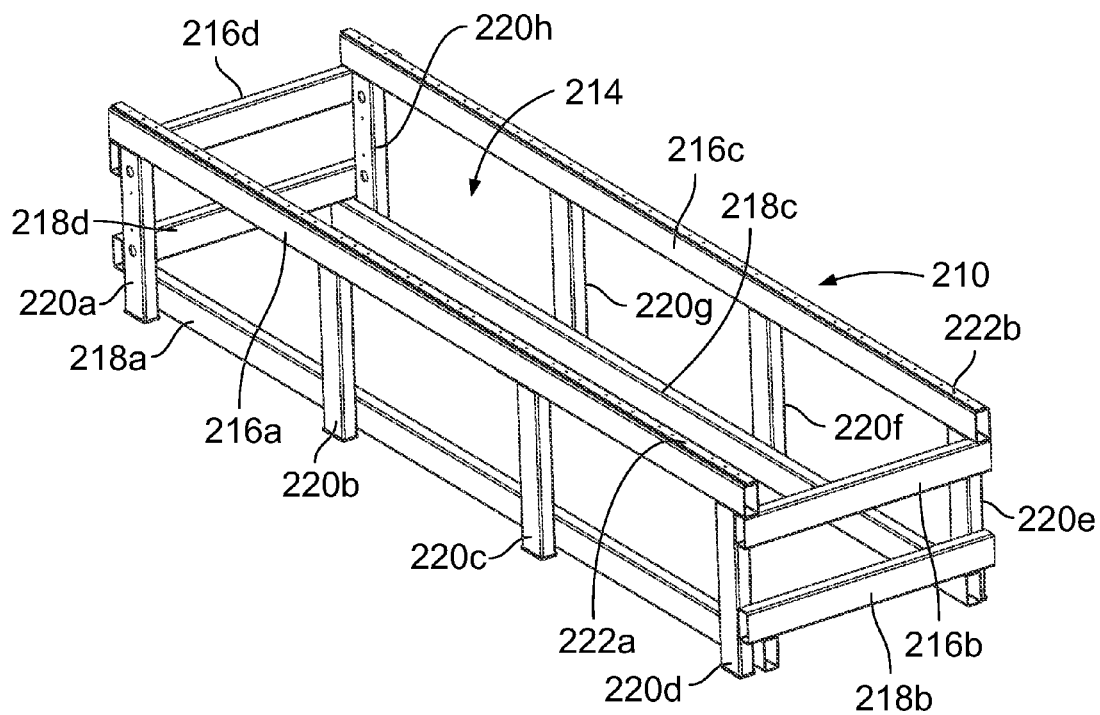
FIG. 6 is perspective view of a portion of a frame of the automated bender.

The first frame assembly 210, see FIG. 6, may be generally rectangular such that an open space 214 is formed therewithin. The first frame assembly 210 includes upper rectangular rails 216a-216d and lower rectangular rails 218a-218d attached together by a plurality of spaced apart posts 220a-220h. The posts 220a-220h are suitably attached to the floor. The components of the first frame assembly 210 are preferably made of metal and are suitably connected together, such as by welding the components together. A track 222a, 222b is formed in the top surface of each elongated rail 216a, 216c. The track 222a, 222b can be provided on a separate member attached to the elongated rails 216a, 216c, or can be formed in the elongated rails 216a, 216c. Each track 222a, 222b is formed of an inverted V-shaped recess which extends along the length of the rails 216a, 216c. The rails 216a and 216c allow the clamping apparatus 20 which is holding the rear end 36b of the workpiece 22 to be moved towards the bending carousel apparatus 208 for controlling bending of the workpiece 22 based on the data, e.g., conduit type, conduit size, bend location, type of bends etc. determined by the application 901 and inputted to the control device 25.

Figure 7:
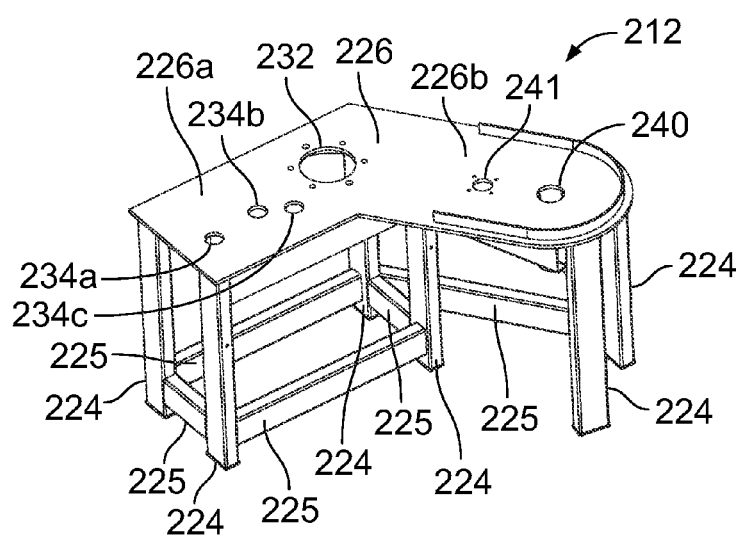
FIG. 7 is perspective view of another portion of a frame of the automated bender.
Figure 8:
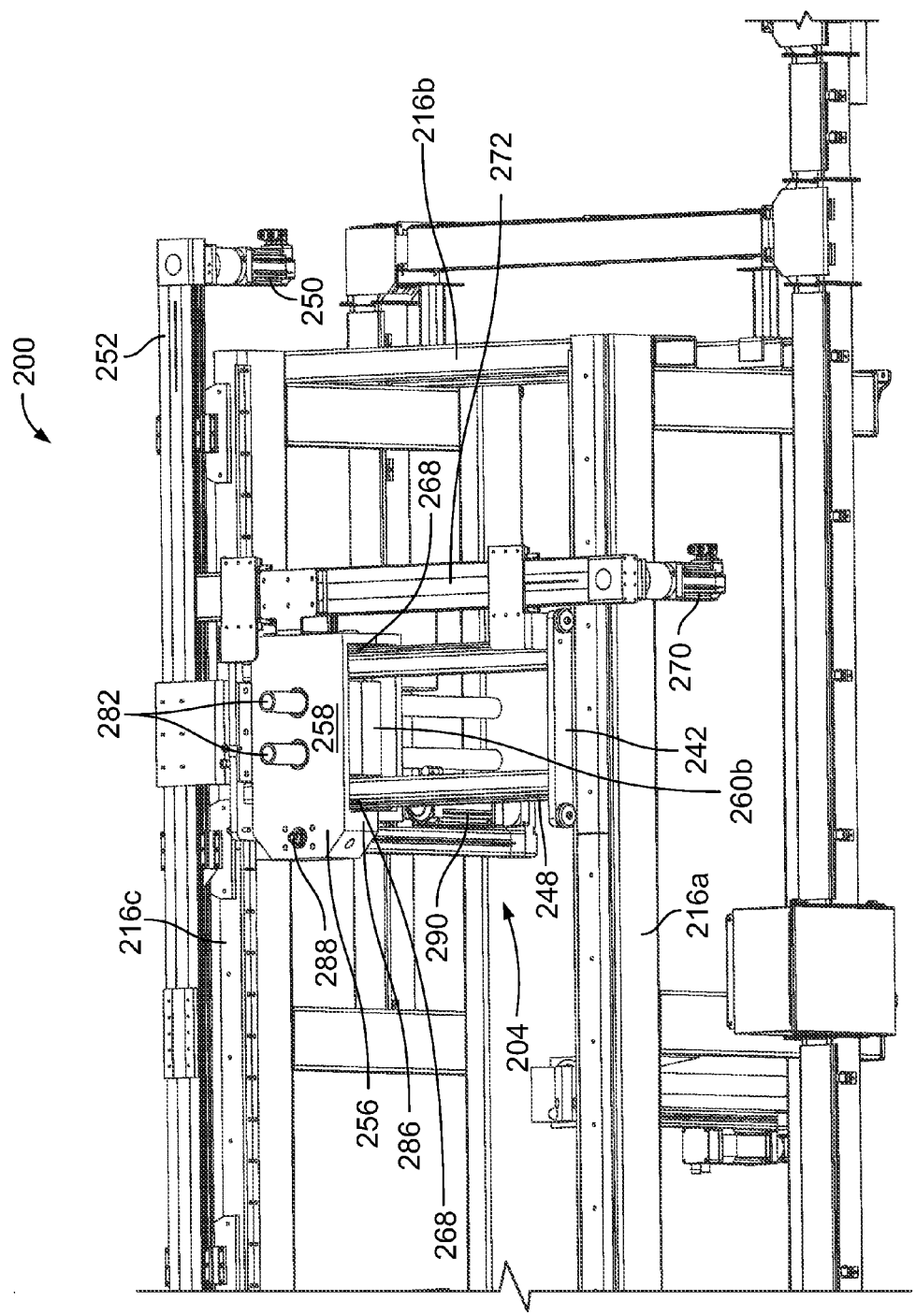
FIGS. 8 and 9 are perspective views of portions of the automated bender.

The second frame assembly 212, see FIG. 7, is generally L-shaped and includes posts 224 connected together by rails 225 to form a base and a top plate 226 mounted on top of the posts 224. The posts 224 are suitably attached to the floor. The top plate 226 has a first portion 226a which is angled relative to a second portion 226b to form a generally L-shaped surface. The second portion 226b may have a curved edge and an upstanding guard provided on its upper surface along the edge thereof. The components of the second frame assembly 212 are preferably made of metal and are suitably connected together, such as by welding the components together. The first portion 226a has spaced apart apertures 232, 234a-234c provided therethrough. The second portion 226b has spaced apart apertures 240, 241 provided therethrough.

The control device 25 may include one or more computing devices. In some embodiments, one or more computing devices that may provide functionality of the control device 25 may be at least partially mounted on the mounting frame 202, such as the first frame assembly 210. Additionally or alternatively, in some embodiments, one or more computing devices that may provide functionality of the control device 25 may be positioned off of the mounting frame 202 and may be communicatively coupled to the bender 200, such as via a network, a wireless communication link, and/or a wired line communication link. In some example embodiments, the control device 25 may be configured to provide an interface for receiving or entering the data used to control bending of the workpiece 22. The control device 25 includes a non-transitory memory 27 and a processor 30 to process the inputted data used for accurately bending the workpiece 22. While illustrated as a single memory 27, it will be appreciated that in some example embodiments, the memory 27 may include multiple individual memory devices collectively providing functionality of the memory 27, which may be distributed across one or more computing devices that may provide functionality of the control device 25. Similarly, while illustrated as a single processor 30, it will be appreciated that in some embodiments, the processor 30 may include multiple processors collectively configured to provide functionality of the processor 30 and which may be distributed across one or more computing devices that may provide functionality of the control device 25. In some example embodiments, the memory 27 may comprise non-transitory memory. The memory 27 stores code which when executed by the processor 30 uses the data to fabricate the workpiece 22, e.g., as described herein. In this regard, the processor 30 may be configured to control operation (e.g., movement) of one or more components of the automated bender 200 that may be used to manipulate a workpiece 22 for purposes of bending the workpiece 22 based at least in part on inputted data, code stored in memory 27, and/or based on a hardware configuration of the processor 30. The data may include various types of information including a type of workpiece 22, a size of the workpiece 22, a type of bend, a determined location of the bend, etc. (see, e.g., FIG. 37). The data sent by the application 901 is used by the automated bender 200 for bending the workpiece 22 based on the architectural drawings. The control device 25 may also include a keypad for entering additional data and/or a display for viewing the data.

Figure 9:
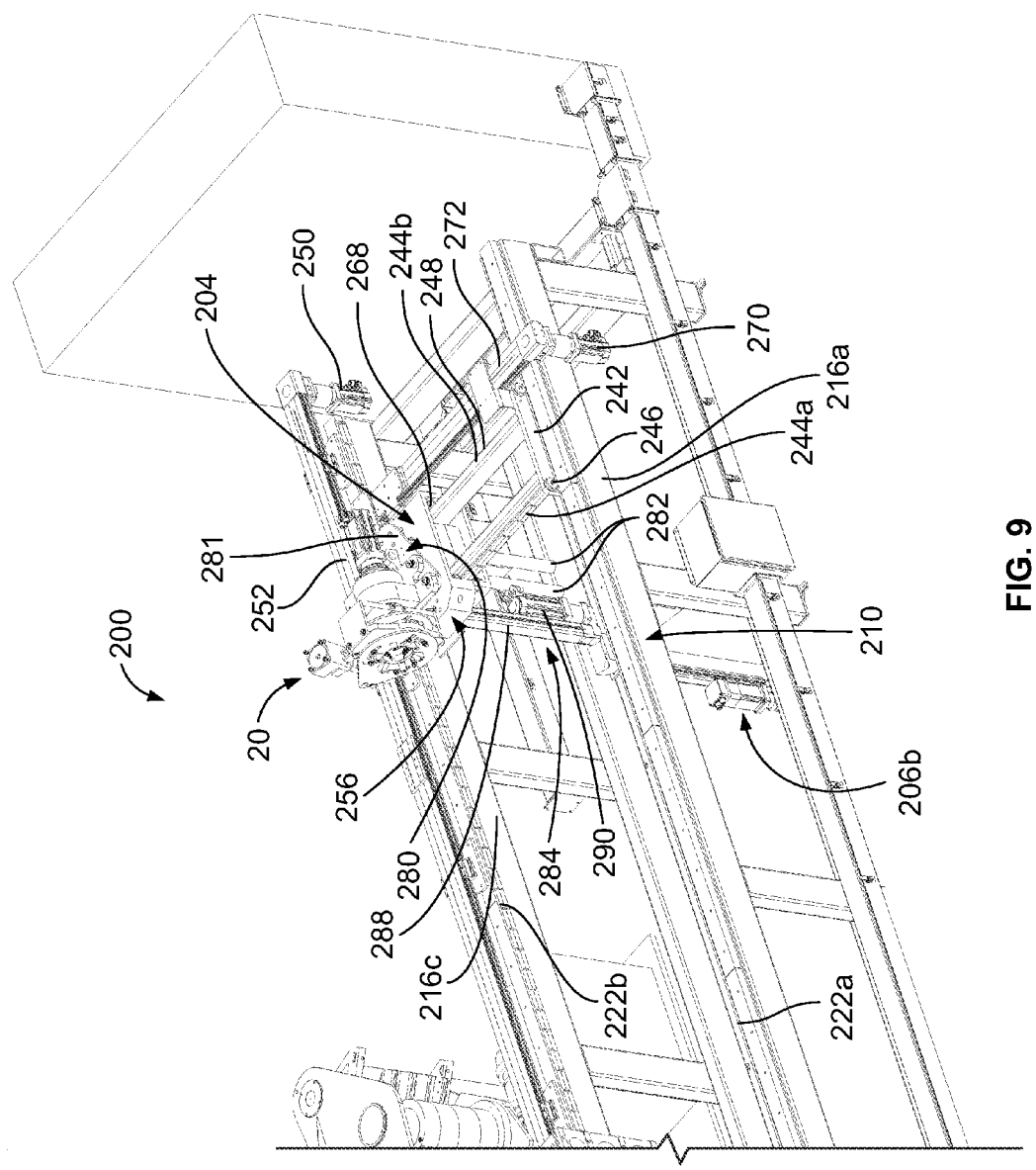

The clamping apparatus 20 is mounted to the carriage assembly 204, see FIG. 9, which can translate along the tracks 222a, 222b. The carriage assembly 204 includes a pair of plates 242, each of which extends parallel to the length of the elongated rails 216a, 216c, and a pair of cross rails 244a, 244b which extend between the plates 242. Each plate 242 has wheels 246 rotatably attached thereto which seats in the respective tracks 222a, 222b to enable the carriage assembly 204 to translate along the rails 216a, 216c. A motor 250 and its driving assembly 252 are attached to the carriage assembly 204 and to the first frame assembly 210 and are used to drive the carriage assembly 204 horizontally back and forth along the length of the rails 216a, 216c in the directions of arrows 254, see FIG. 3. The control device 25 is in communication with the motor 250 for controlling and for monitoring the motor 250. Accordingly, the memory 27 and/or processor 30 may be configured to control driving of the carriage assembly 202 along the length of the rails 216a, 216c. Suitable motors 250 include, but are not limited to, servo motors, stepper motors and DC motors.

Each cross rail 244a, 244b has a track 248 formed in a side surface thereof which extend along the length of the cross rails 244a, 244b. The tracks 248 can be provided on a separate member attached to the cross rails 244a, 244b, or can be formed in the cross 244a, 244b.

The carriage assembly 204 further includes a first mount 256 which seats on the cross rails 244a, 244b and can translate relative to the cross rails 244a, 244b, and a second mount 280 upon which the clamping apparatus 20 is mounted as described herein. The second mount 280 can be lifted relative to the first mount 256 by a lifting assembly 284.

Figure 10:
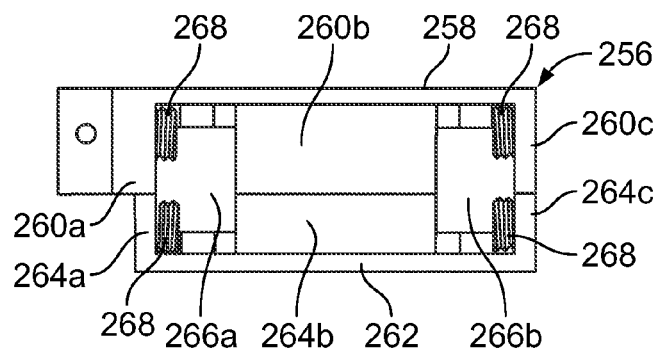
FIG. 10 is a side elevation view of a carriage assembly which forms a portion of the automated bender.
Figure 11:
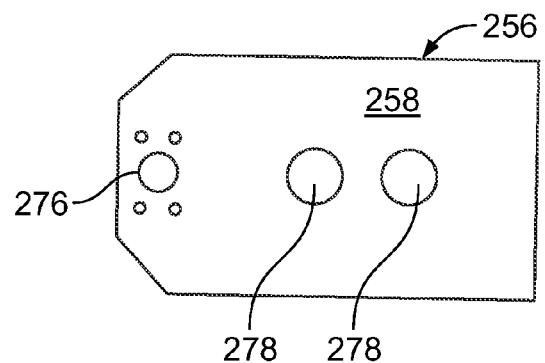
FIG. 11 is a top plan view of the carriage assembly.
Figure 12:
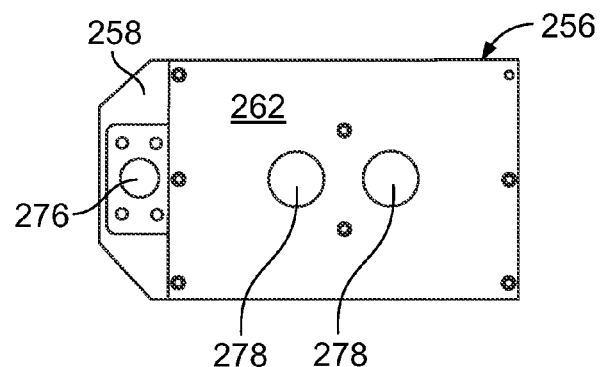
FIG. 12 is a bottom plan view of the carriage assembly.
Figure 13:
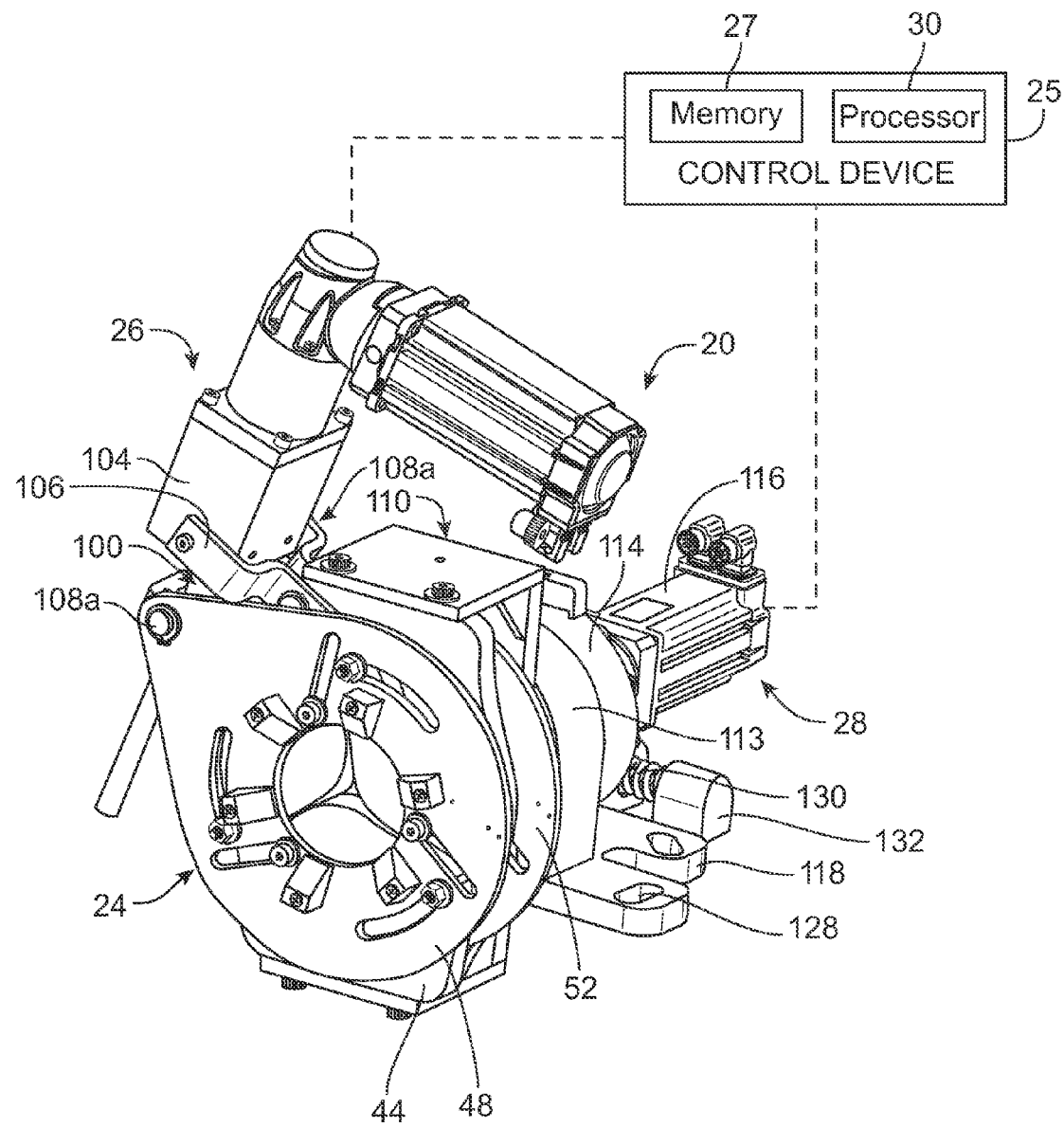
FIG. 13 is a perspective view of a clamping apparatus used which forms a portion of the automated bender, showing a control device in schematic form.
Figure 15:
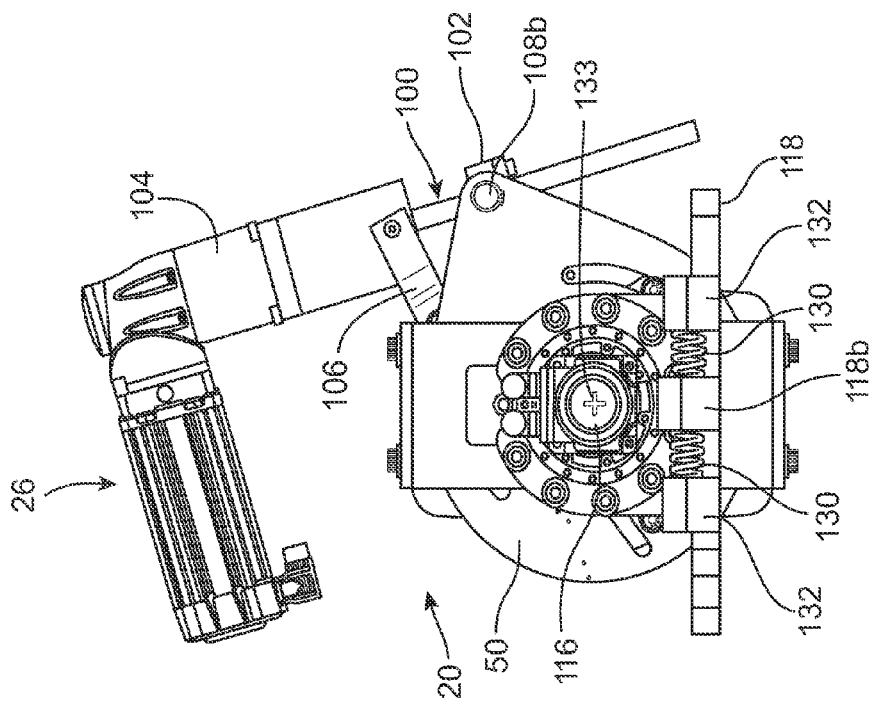
FIG. 15 is a rear elevation view of the clamping apparatus.
Figure 14:
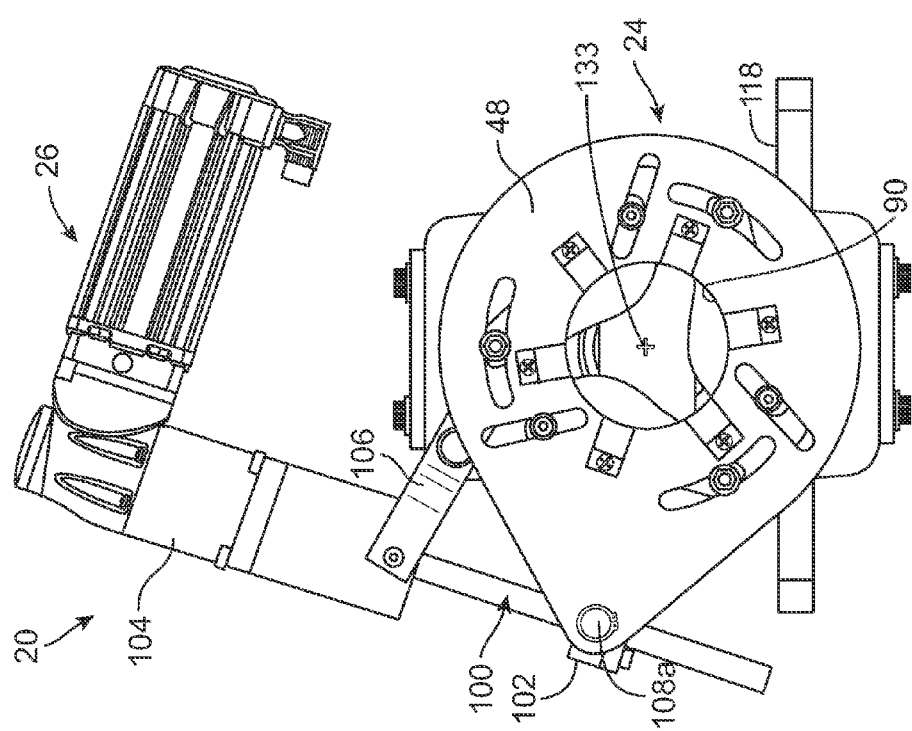
FIG. 14 is a front elevation view of the clamping apparatus.
Figure 16:
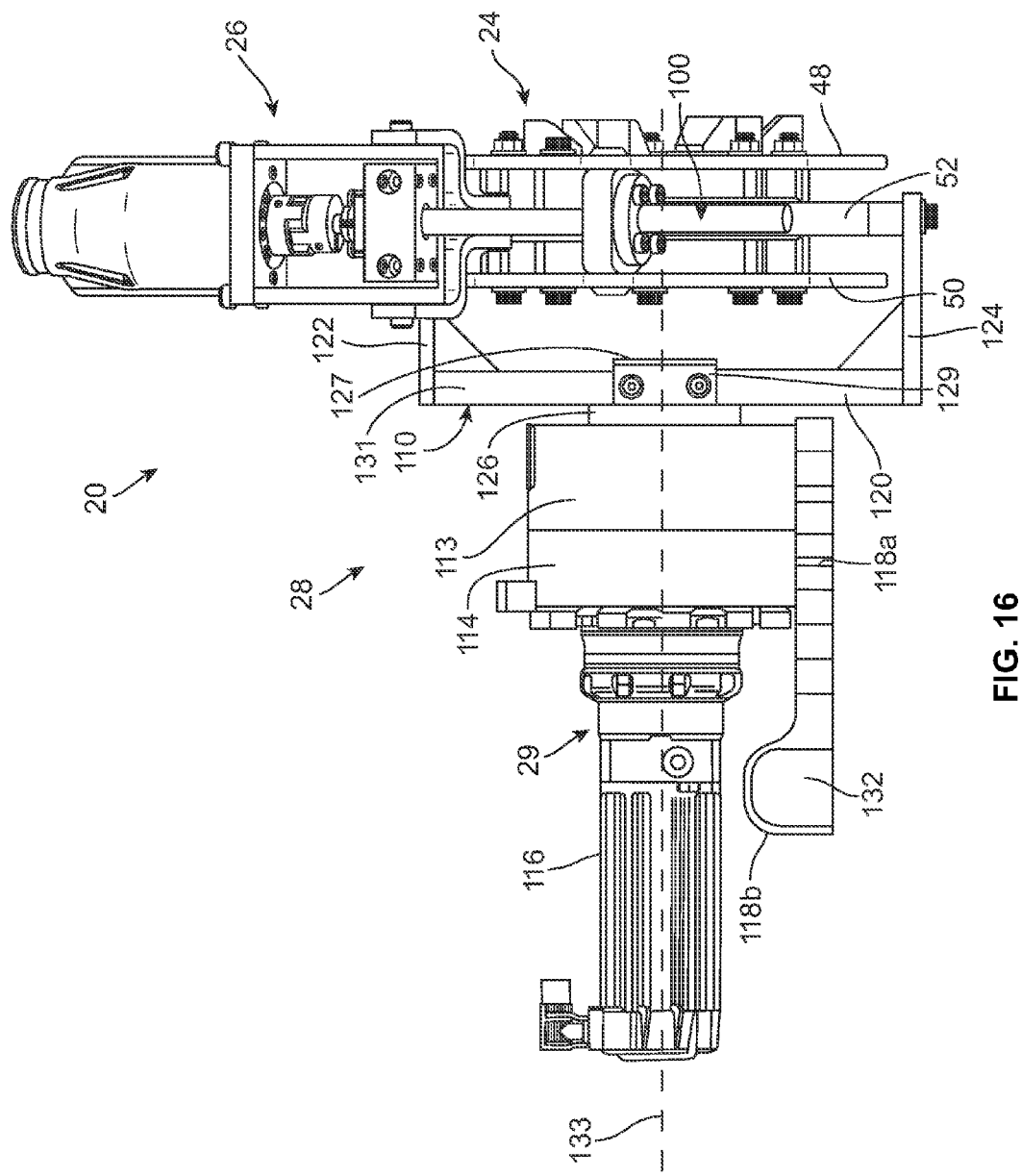
FIG. 16 is a side elevation view of the clamping apparatus.
Figure 17:
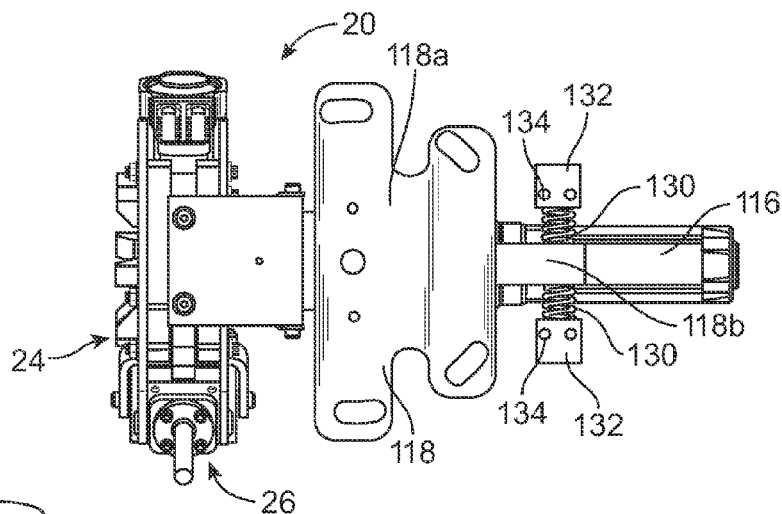
FIG. 17 is a bottom plan view of the clamping apparatus.
Figure 18:
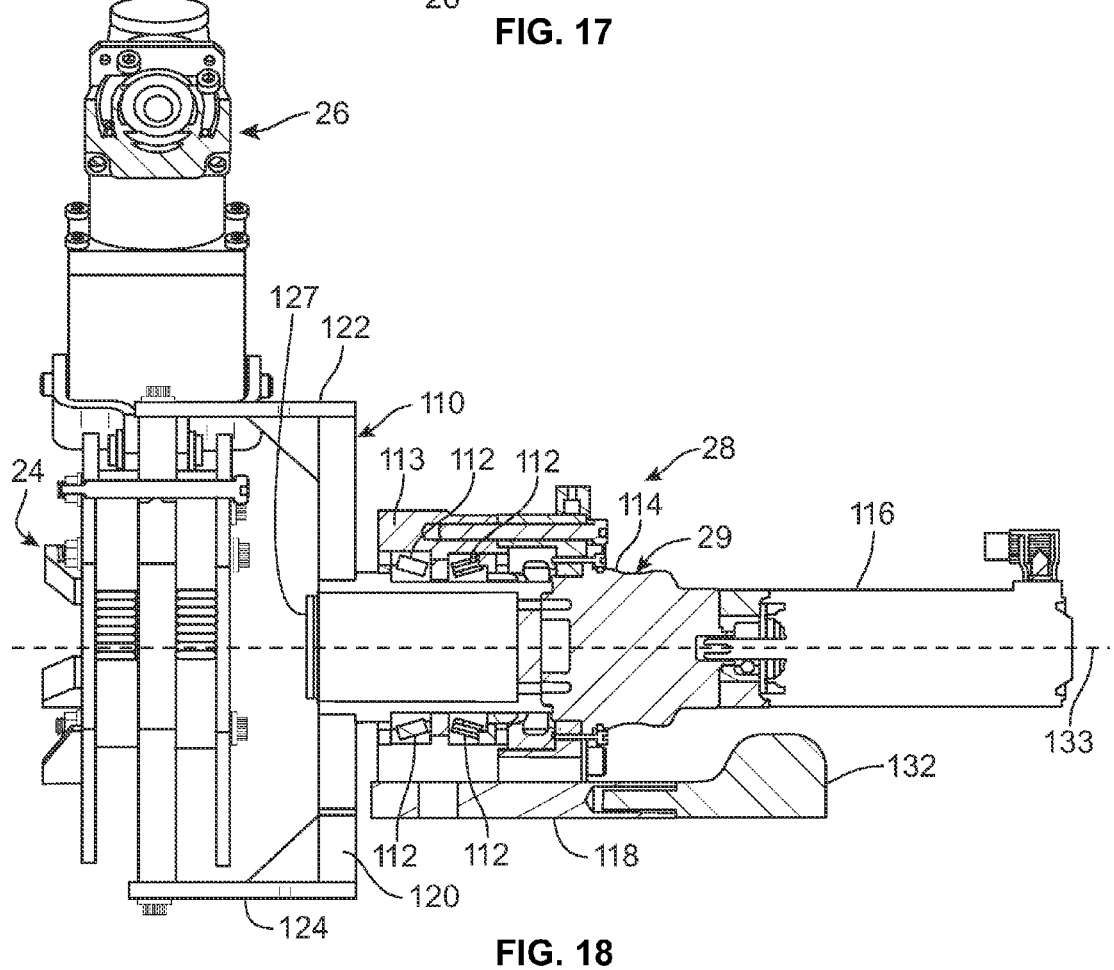
FIG. 18 is a cross-sectional view of the clamping apparatus.
Figure 19:
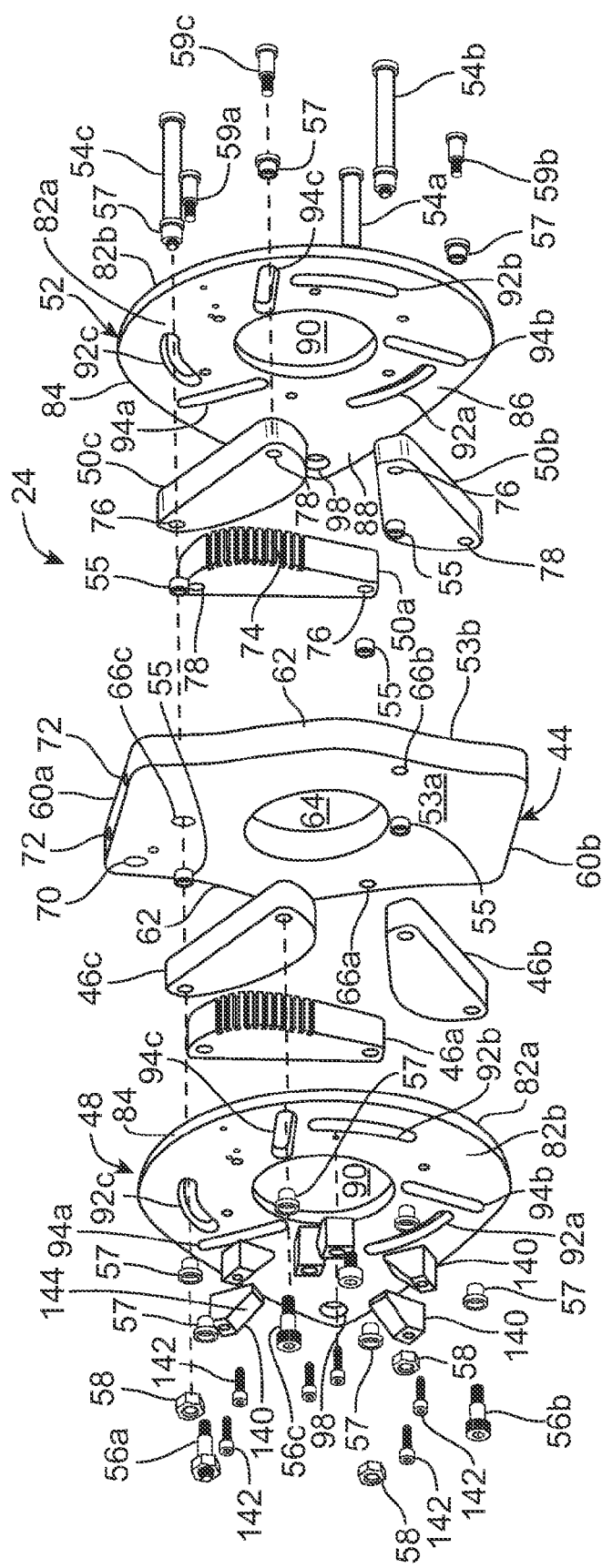
FIG. 19 is an exploded perspective view of components of the clamping apparatus.

As shown in FIGS. 10-12, the first mount 256 includes a top plate 258 having three legs 260a-260c depending downwardly therefrom, and a bottom plate 262 having three legs 264a-264c extending upwardly therefrom. Legs 260a, 264a align; legs 260b, 264b align; and legs 260c, 264c align, such that passageways 266a, 266b are formed through the mount 256. A plurality of rotatable wheels 268 are provided on legs 260a, 260c, 264a, 264c; the wheels 268 mate with the tracks 248 on the cross rails 244a, 244b. The top plate 258 has an aperture 276 therethrough proximate to an end thereof. The top plate 258, legs 260b, 264b and bottom plate 262 has a pair of spaced apart apertures 278 therethrough.

As shown in FIG. 9, the second mount 280 has a planar top plate 281 having pair of spaced apart tubes 282 extending downwardly from the plate 281. The top plate 281 seats on top of the top plate 258 of the first mount and the tubes 282 extend through the apertures 278.

A motor 270 and its driving assembly 272 are attached to the cross rail 244b and to the rails 216a, 216c, and are used to drive the first mount 256 back and forth along the length of the cross rails 244a, 224b in the directions of arrows 274, see FIG. 3, by the wheels 268 rolling along the track 248. The control device 25 is in communication with the motor 270 for controlling and for monitoring the motor 270. Accordingly, the memory 27 and/or processor 30 may be configured to control driving the first mount 256. Suitable motors 270 include, but are not limited to, servo motors, stepper motors and DC motors.

The lift assembly 284 is used to lift the second mount 280 away from the first mount 256. The lift assembly 284 is attached to the first mount 256 and includes a housing 286 having an actuating rod 288 therein and a motor 290 for moving the actuating rod 288 upwardly and downwardly. The control device 25 is in communication with the motor 290 for controlling the motor 290 and for monitoring the motor 290. Accordingly, the memory 27 and/or processor 30 may be configured to control movement of the actuating rod 288. Suitable motors 290 include, but are not limited to, servo motors, stepper motors and DC motors. The housing 286 extends downwardly from the plate 258 of the first mount 256 and has a central passageway which aligns with the aperture 276. The actuating rod 288 is mounted in the housing 286 and extends through the aperture 276. The actuating rod 288 can translate upwardly and downwardly within the housing 286. When the actuating rod 288 is lifted sufficiently upward relative to a position of the second mount 288, the end of the actuating rod 288 engages the underside of the second mount 280 to move the second mount 280 vertically upwardly relative to the first mount 256 in the directions of arrows 292, see FIG. 4. The engagement of the tubes 282 in the apertures 278 prevents the second mount 280 from disengaging from the first mount 256.

The clamping apparatus 20 is mounted on the top plate 281 of the second mount 280. As a result, the clamping apparatus 20 can translate along the directions of any one of arrows 254, 274, 292 as needed to operate the bender 200 as described herein.

The clamping apparatus 20, see FIGS. 13-19, is used to hold the workpiece 22 so that a bend can be formed in the workpiece 22, and is further used to rotate the workpiece 22 so that additional bend(s) can be formed in the workpiece 22 without having to disengage the workpiece 22 from the clamping apparatus 20. Such a clamping apparatus 20 may be a rotary chuck which is fully described in co-pending application Ser. No. 14/081,262, filed on Nov. 15, 2013, which is incorporated by reference in its entirety. It will be appreciated that the clamping apparatus 20 shown herein is provided as a non-limiting example of a suitable clamping apparatus that may be used with the automated bender 200. Rotation of the workpiece 22 by the clamping apparatus 20 may be performed under control of the memory 27 and/or processor 30, such as based on the data determined by the application 901. The clamping apparatus 20 solves the issue of having to manually change collets or mandrels because the clamping apparatus 20 enables the user to securely clamp the workpiece 22 and rotate the workpiece 22 into a desired position. The clamping apparatus 20 includes a clamp assembly 24, a drive mechanism 26 for operating the clamp assembly 24, a rotary assembly 28 for rotating the clamp assembly 24 and its drive mechanism 29.

The clamp assembly 24 includes a stationary base plate 44, a first set of serrated jaws 46a, 46b, 46c sandwiched between the base plate 44 and a first actuator plate 48, a second set of serrated jaws 50a, 50b, 50c sandwiched between the base plate 44 and a second actuator plate 52, and a set of pivot fasteners 54a, 54b, 54c and their associated spacers 55, 57 and their associated lock nuts 58, a first set of drive fasteners 56a, 56b, 56c and their associated spacers 57, and a second set of drive fasteners 59a, 59b, 59c and their associated spacers 57. The pivot fasteners 54a, 54b, 54c may be formed of bolts. The drive fasteners 56a, 56b, 56c, 59a, 59b, 59c have threaded ends and may be formed of bolts.

The set of pivot fasteners 54a, 54b, 54c and their associated lock nuts 58 connect the actuator plate 52 to the jaws 50a, 50b, 50c to the base plate 44 to the jaws 46a, 46b, 46c to the actuator plate 48. The first set of drive fasteners 56a, 56b, 56c and their associated spacers 57 connect the actuator plate 48 to the jaws 46a, 46b, 46c. The second set of drive fasteners 59a, 59b, 59c and their associated spacers 57 connect the actuator plate 52 to the jaws 50a, 50b, 50c.

The base plate 44 has opposite flat side surfaces 53a, 53b having an upper edge 60a, a lower edge 60b, and opposite side edges 62. Each upper and lower edge 60a, 60b is generally planar. The base plate 44 has a central circular opening 64 around which are three uniformly spaced pivot holes 66a, 66b, 66c, each of which pass completely through the base plate 44. Each pivot hole is preferably 120° from its adjacent pivot holes. Each pivot hole 66a, 66b, 66c is located the same radial distance from the center of the circular opening 64. A securement hole 70 is located toward a top side corner of the base plate 44. A first set of mounting openings 72 are provided in the upper edge 60a of the base plate 44 for attachment to the rotary assembly 28 as described herein, and a second set of mounting openings (not shown) are provided in the lower edge 60b of the base plate 44 for attachment to the rotary assembly 28 as described herein.

The first and second actuator plates 48, 52 are mirror images of the other. Each actuator plate 48, 52 has opposite flat side surfaces 82a, 82b and has an outer edge 84 which generally defines a teardrop-shape having a main body portion 86 and an extended portion 88. The main body portion 86 of each actuator plate 48, 52 has a generally central circular opening 90 around which are three uniformly spaced arced rotation slots 92a, 92b, 92c and three uniformly spaced linear drive slots 94a, 94b, 94c are provided. The start end of each arced rotation slot 92a, 92b, 92c is 120° from the start end of its adjacent arced rotation slots 92a, 92b, 92c, and the start end of each linear drive slot 94a, 94b, 94c is 120° from the start end of its adjacent linear drive slots 94a, 94b, 94c. Each arced rotation slot 92a, 92b, 92c is arced about the center of the opening 90. Each arced rotation slot 92a, 92b, 92c has a corresponding linear drive slot 94a, 94b, 94c. Each arced rotation slot 92a, 92b, 92c is located the same radial distance from the center of the circular opening 90, and each linear drive slot 94a, 94b, 94c is located the same radial distance from the center of the circular opening 90. Each linear drive slot 94a, 94b, 94c extends in a somewhat radial manner from the center of the opening 90. The extended portion 88 has a drive hole 98 extending therethrough for attachment to the drive mechanism 26.

The first set of jaws 46a, 46b, 46c are proximate to the first side surface 53a of the base plate 44 and proximate to side surface 82a of actuator plate 48. The second set of jaws 50a, 50b, 50c are proximate to the second side surface 53b of the base plate 44 and proximate to side surface 82a of actuator plate 50.

Each jaw 46a, 46b, 46c, 50a, 50b, 50c is uniformly shaped and is hardened to prevent deformation of the jaw 46a, 46b, 46c, 50a, 50b, 50c. Each jaw 46a, 46b, 46c, 50a, 50b, 50c has a workpiece engaging surface 74, which may, for example, be formed by a plurality of teeth to form serrations thereon, a first pivot hole 76 and a second pivot hole 78 provided therethrough. The serrations are parallel to an axis defined through a center of the openings 90 in the actuator plates 48, 52. The second pivot hole 78 have an internal thread. The jaws 46a, 46b, 46c, 50a, 50b, 50c are uniformly spaced both rotationally around the openings 64, 90 and radially from the centers of the openings 64, 90 so that the workpiece engaging surface 74 of the jaws 46a, 46b, 46c, 50a, 50b, 50c form a working centerline 133 that passes through the center of the openings 64, 90.

Each pivot fastener 54a, 54b, 54c passes through a spacer 57 mounted in the respective rotation slot 92a, 92b, 92c in actuator plate 52, a corresponding jaw pivot hole 76 in jaws 50a, 50b, 50c, a pair of spacers 55 mounted in the respective pivot hole 66a, 66b, 66c of the base plate 44 (one spacer 55 is mounted into side surface 53b and another spacer 55 is mounted into side surface 53a), a corresponding jaw pivot hole 76 in jaws 46a, 46b, 46c, and a spacer 57 mounted in the respective rotation slot 92a, 92b, 92c in actuator plate 48. The jaws 46a, 46b, 46c, 50a, 50b, 50c abut against the spacers 57 to provide a space between the jaws 46a, 46b, 46c, 50a, 50b, 50c and the base plate 44. Each drive fastener 56a, 56b, 56c passes through a spacer 57 mounted in the respective linear slot 94a, 94b, 94c in actuator plate 48 and into a corresponding jaw pivot hole 78 in jaws 46a, 46b, 46c. The jaws 46a, 46b, 46c abut against the spacers 57 to provide a space between the jaws 46a, 46b, 46c and the actuator plate 48. The pivot hole 78 in jaws 46a, 46b, 46c are internally threaded to engage the threaded end of the drive fastener 56a, 56b, 56c to mate the actuator plate 48 and the jaws 46a, 46b, 46c together. Each drive fastener 59a, 59b, 59c passes through a spacer 57 mounted in the respective linear slot 94a, 94b, 94c in actuator plate 52 and into a corresponding jaw pivot hole 78 in jaws 50a, 50b, 50c. The jaws 50a, 50b, 50c abut against the spacers 57 to provide a space between the jaws 50a, 50b, 50c and the actuator plate 52. The pivot holes 78 in jaws 50a, 50b, 50c are internally threaded to engage the threaded end of the drive fastener 59a, 59b, 59c to mate the actuator plate 52 and the jaws 50a, 50b, 50c together. A lock nut 58 is secured to the ends of the pivot fasteners 54a, 54b, 54c and hold the jaws 46a, 46b, 46c, 50a, 50b, 50c, base plate 44 and actuator plates 48, 52 together, while allowing rotating movement of the actuator plates 48, 52 with respect to the base plate 44 and the jaws 46a, 46b, 46c, 50a, 50b, 50c. The actuator plates 48, 52 are aligned in registry with each other and with the circular opening 64 so that the centerline 133 of openings 90 and 64 form a common centerline that is co-linear with the working centerline of the jaws 46a, 46b, 46c, 50a, 50b, 50c.

The drive mechanism 26 drives the clamp assembly 24 based on the data from the control device 25. The drive mechanism 26 includes a threaded drive rod 100 preferably formed of ¾"-10 ACME screw, a threaded drive coupling 102 for attaching the drive rod 100 to the clamp assembly 24, a motor 104 attached to an end of the drive rod 100, mounting brackets 106 for attaching the motor 104 to the clamp assembly 24. Suitable motors 104 include, but are not limited to, servo motors, stepper motors and DC motors. The control device 25 is in communication with the motor 104 for controlling the motor 104 and for monitoring the motor 104. The threaded drive coupling 102 is in threaded engagement with the threaded rod 100. The drive coupling 102 includes two opposed protrusions 108a, 108b that pivotally engage the drive holes 98 of the actuator plates 48, 52 so that the drive coupling 102 does not rotate with the threaded drive rod 100. While the drive mechanism 26 is described as a threaded drive rod 100, threaded drive coupling 102 and motor 104, other drive mechanisms may be provided for operating the clamp assembly 24, such as pneumatic or hydraulic drive assemblies as are known in the art.

The mounting brackets 106 for attaching the motor 104 to the clamp assembly 24 extend between and are attached to the motor 104 and the base plate 44. This fixes the position of the motor 104 relative to the base plate 44 such that the motor 104 moves when the clamp assembly 24 is rotated as described herein.

The control device 25 of some example embodiments may be configured to monitor and determine the current draw of the motor 104. The control device 25 may be further configured to monitor and determine the rotation of the motor 104 and determine the travel length of the drive rod 100.

The clamp assembly 24 and its associated drive mechanism 26 are mounted to the rotary assembly 28. The rotary assembly 28 includes a frame 110, and its drive mechanism 29 which includes a series of roller bearings 112 mounted in a bearing carrier 113, a rotary gearbox 114, a motor 116 and a stable surface, such as a mounting plate 118, for the mounting the rotary gearbox 114 and the motor 116. The mounting plate 118 is stable relative to the ground. The roller bearings 112 may be tapered bearings, spherical roller bearings, cylindrical roller bearings, radial ball bearings, etc. The control device 25 is in communication with the motor 116 for controlling the motor 116 and for monitoring the motor 116. Accordingly, the memory 27 and/or processor 30 may be configured to control rotation of the rotary assembly 28 for purposes of driving the clamp assembly 24. Suitable motors 116 include, but are not limited to, servo motors, stepper motors and DC motors.

The frame 110 attaches the drive mechanism 29 to the clamp assembly 24. The frame 110 is generally U-shaped and includes a base plate 120, a first arm 122 extending from an upper end of the base plate 120, and a second arm 124 extending from a lower end of the base plate 120. The first arm 122 is fixedly secured to the planar upper edge 60a, 60a' of the base plate 44, 44' by suitable means such as fasteners that extend through the arm 122 and into the base plate 44, 44'. The second arm 124 is fixedly secured to the planar lower edge 60b, 60b' of the base plate 44, 44' by suitable means such as fasteners that extend through the arm 122 and into the base plate 44, 44'. A U-shaped stop plate 125 is attached to the base plate 120 and includes a base plate 127 and arms 129 extending from side edges of the base plate 127. The arms 129 are fixedly secured to the planar side edges 131 of the base plate 127 by suitable means such as fasteners that extend through the arms 129 and into the base plate 127.

A drive shaft 126 extending from the motor 116 is attached to the base plate 120 by suitable means, such as a bracket and fasteners. The stop plate 125 overlaps the end of the drive shaft 126 to protect the drive shaft 126 from damage when the workpiece 22 is inserted into the clamping apparatus 20 (the stop plate 125 prevents the workpiece 22 from contacting the drive shaft 126). Thus, when the motor 116 rotates, the frame 110 rotates around centerline 133, which rotates the clamp assembly 24 and its drive mechanism 26. The rotary gearbox 114 allows for 360 degree rotation of the clamp assembly 24 and its associated drive mechanism 26 and the workpiece 22 when mounted therein around centerline 133 relative to the ground. The rotary gearbox 114 has enough torque to rotate a workpiece 22 over 184 pounds in overall weight and that has a 90 degree bend in the middle of the workpiece 22. The gearbox 114 allows for pinpoint accuracy when rotating the workpiece 22. The bearing carrier 113 operates smoothly under harsh conditions. The bearing carrier 113 can withstand the full weight of a 10 foot length of 4 inch rigid conduit hanging from the clamp assembly 24.

The motor 116 is fixedly mounted to the second mount 280 via the mounting plate 118. The mounting plate 118 is formed of a flat plate having a main body portion 118a and an extension portion 118b extending from an end of the main body portion 118a. The mounting plate 118 is suitably attached to the top plate 281 of the second mount 280 such as by fasteners which extend through apertures 128 provided through the main body portion 118a. As shown, the apertures 128 are enlarged such that the mounting plate 118 can pivot relative to the ground and relative to the centerline 133, resulting in angular movement of the clamp assembly 24 relative to the centerline 133 and relative to the stable surface 117 as described herein. The bearing carrier 113 and the rotary gearbox 114 mount on the main body portion 118a and are affixed thereto such that movement of the mounting plate 118 moves the drive mechanism 29.

A pair of alignment springs 130 and their associated housings 132 are provided to allow the clamping apparatus 20 to pivot a predetermined amount relative to the second mount 280, preferably 12 degrees, to compensate for inconsistencies in material straightness in the workpiece 22, and to allow for an additional degree of freedom during spring back of the workpiece 22 during the bending process. In addition, once the workpiece 22 is unclamped from the clamp assembly 24 and the clamp assembly 24 is unloaded, the alignment springs 130 self-center the clamping apparatus 20 relative to the second mount 280.

The housings 132 are suitably fixed to the top plate 281 of the second mount 280 such as by fasteners which extend through bores 134 provided in the housings 132. An end of each alignment spring 130 seats within the respective housing 132 and the opposite end of each alignment spring 130 abuts against the extension portion 118b of the mounting plate 118.

The clamping apparatus 20 can pivot relative to the second mount 280 because of the enlarged apertures in the main body portion 118a of the mounting plate 118. The alignment springs 130 limit the amount of pivot and return the clamping apparatus 20 to the center position.

The first and second assemblies 206a, 206b, see FIGS. 1, 3, 4 and 20-23, forming the workpiece holding apparatus is positioned within the space 214 formed by the first frame assembly 210 and is used to hold the workpiece 22. The first assembly 206a is attached to posts 220a, 220h of the first frame assembly 210, and the second assembly 206b is positioned at approximately the midpoint of the first frame assembly 210 and is mounted to the post 220c of the first frame assembly 210.

Figure 20:
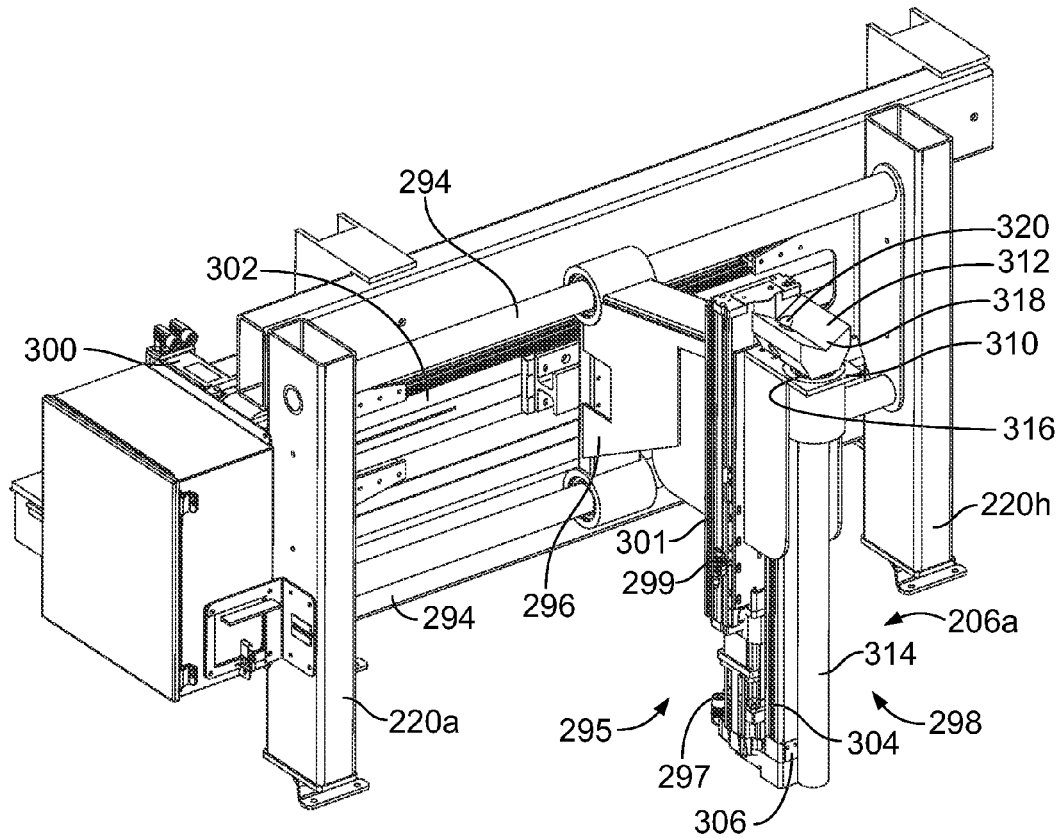
FIGS. 20-25 are perspective views of various portions of the automated bender.
Figure 21:
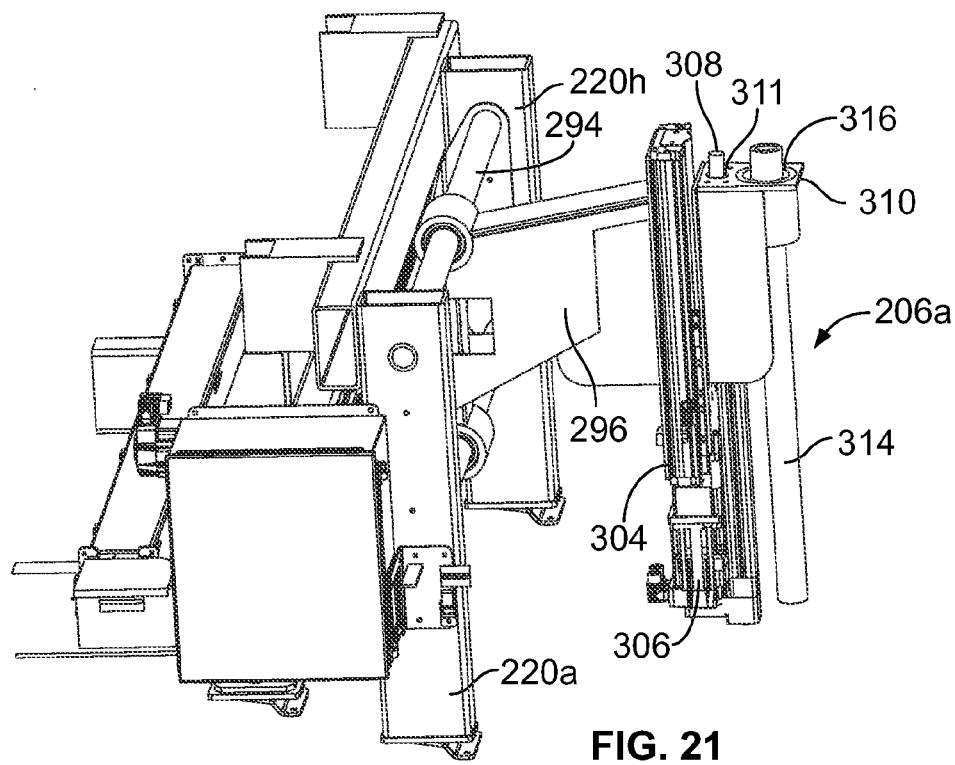

The first assembly 206a, FIGS. 20 and 21, includes a pair of tubes 294 which extend between the posts 220a, 220h, a mounting bracket 296 through which the tubes 294 extend, a first lift assembly 295 attached to the mounting bracket 296, a second lift assembly 298 attached to the first lift assembly 295, and a motor 300 and its driving assembly 302 for moving the mounting bracket 296 and lift assembly 298 in the directions of arrows 274.

The mounting bracket 296 has a pair of apertures through which the tubes 294 extend. The mounting bracket 296 can slide along tubes 294 in the direction of arrows 274 under the power of driving assembly 302. The motor 300 and its driving assembly 302 are attached to the posts 220*a*, 220*b* and to the mounting bracket 296, and are used to drive the mounting bracket 296 and the first and second lift assemblies 295, 298 back and forth along the length of the tubes 294 in the directions of arrows 274. The control device 25 is in communication with the motor 300 for controlling and for monitoring the motor 300. Accordingly, the memory 27 and/or processor 30 may be configured to control driving of the mounting bracket 296 and the first and second lift assemblies 295, 298. Suitable motors 300 include, but are not limited to, servo motors, stepper motors and DC motors.

The first lift assembly 295 includes a vertical housing 301 attached to the mounting bracket 296, and a motor 297 and its driving assembly 299 are attached to the housing 301. The control device 25 is in communication with the motor 297 for controlling and for monitoring the motor 297. Suitable motors 297 include, but are not limited to, servo motors, stepper motors and DC motors.

Figure 22:
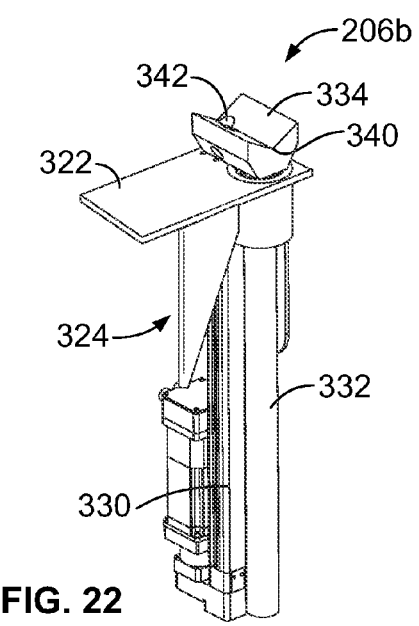
Figure 23:
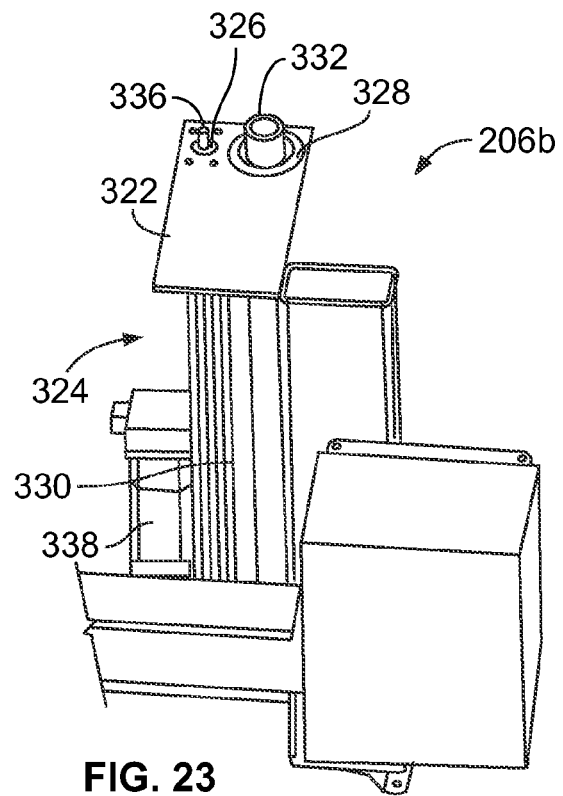
Figure 24:
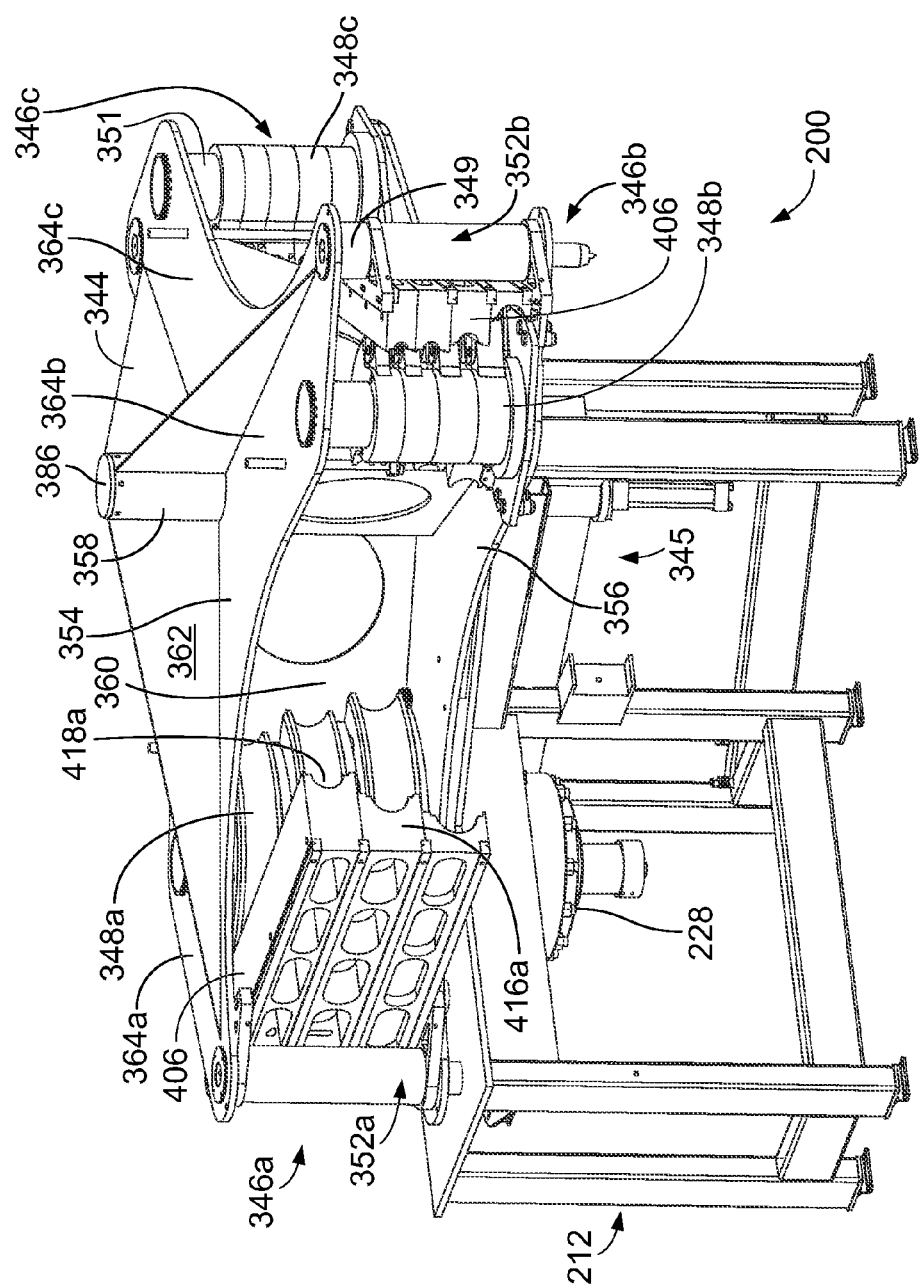

As shown in FIGS. 22 and 23, the second lift assembly 298 includes a vertical housing 304 slidably attached to the housing 301, a horizontal bracket 310 attached to the housing 304, a motor 306, and an actuating rod 308 in the housing 304 which is in communication with the motor 306 and extends through an aperture 311 in the bracket 310. The motor 297 and the driving assembly 299 of the first lift assembly 295 are used to lift the second lift assembly 298 relative to the first lift assembly 295 and the mounting bracket 296. In this regard, lifting of the second lift assembly 298 may be controlled by the memory 27 and/or processor 30 of some example embodiments.

Figure 37:
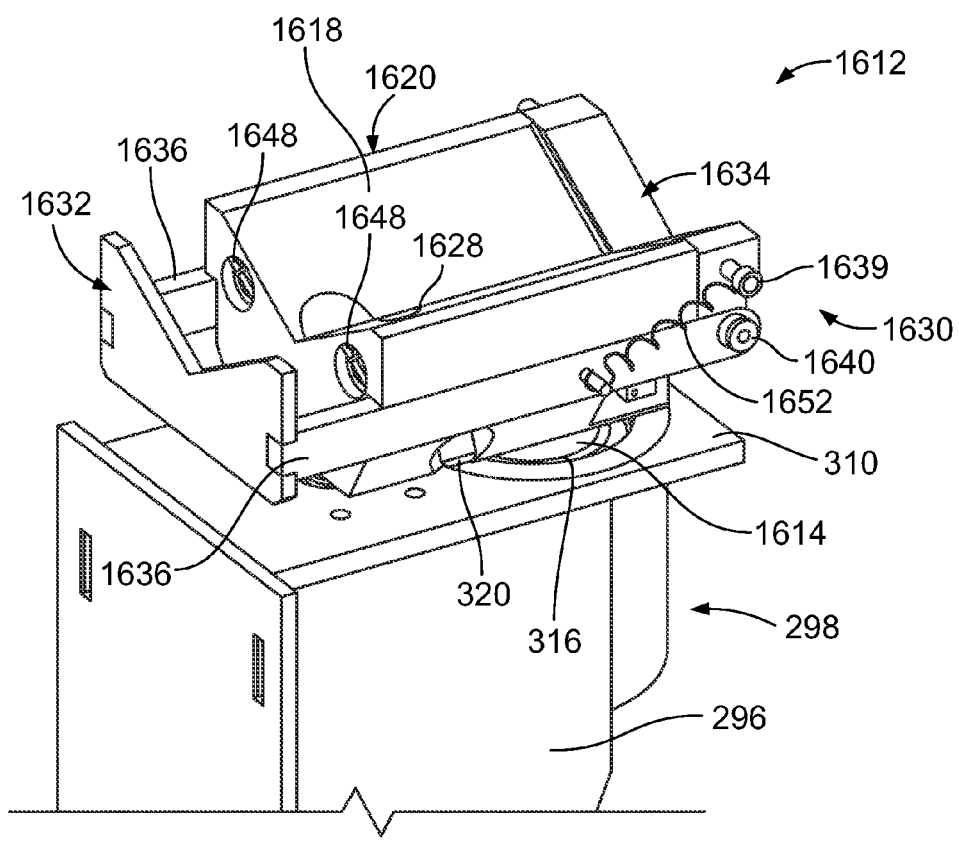
FIG. 37 is a perspective view of an alternate seat, in a first position, used in the automated bender.
Figure 38:
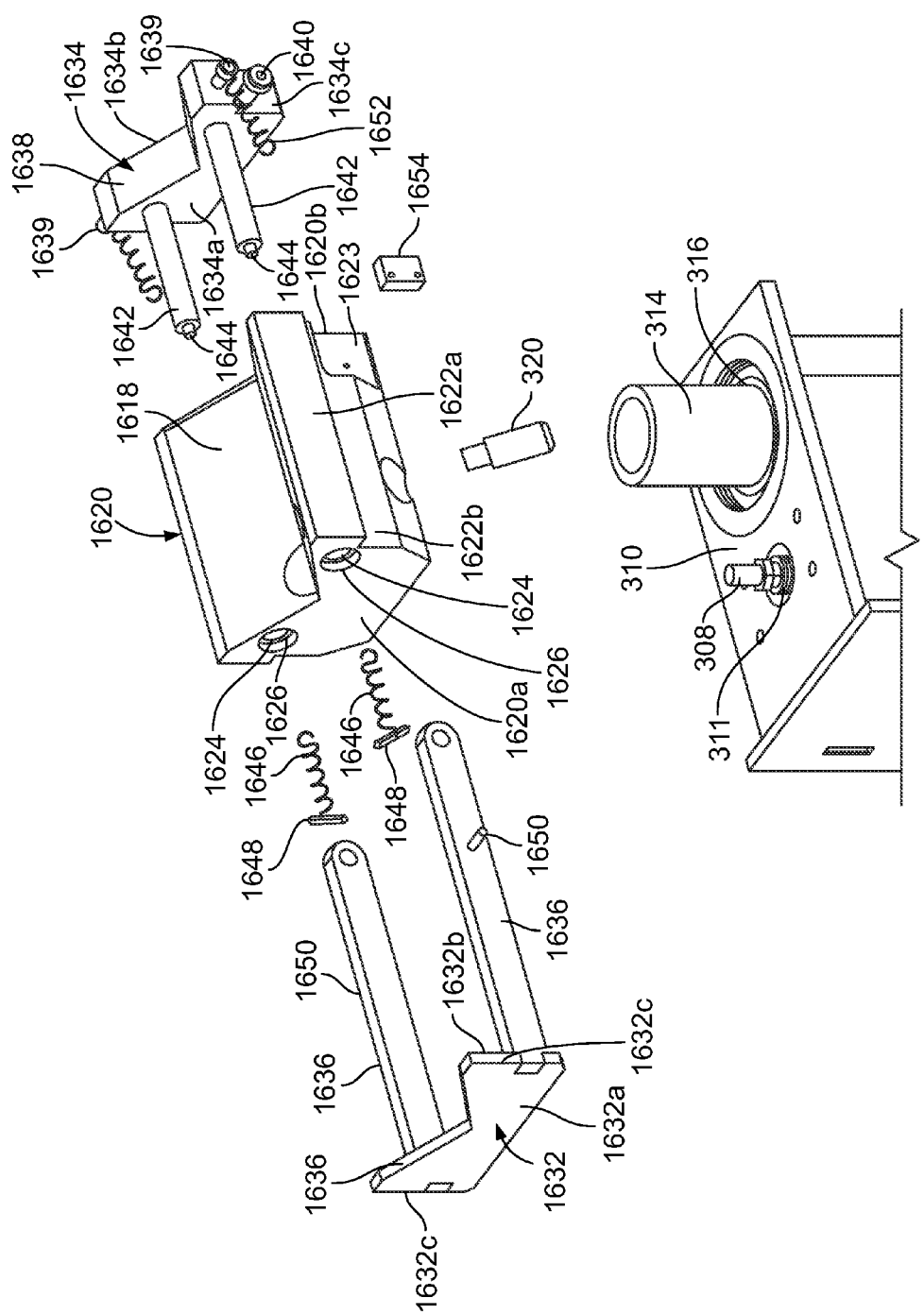
FIG. 38 is an exploded perspective view of the seat of FIG. 37.

As best shown in FIG. 20, the second lift assembly 298 further includes a seat 312 which seats on top of the bracket 310, and an elongated tube 314 which extends from the lower surface of the seat 312 and through an aperture 316 in the bracket 310. This seat 312 and tube 314 are a first embodiment of the seat 312 and tube 314. FIGS. 37-38 show a second embodiment of a seat 1612 and a tube 1614 which can be used in the automated bender 200 in place of seat 312 and tube 314.

The second lift assembly 298 is used to raise and lower the seat 312 toward/away from the top of the bracket 310 in the direction of arrows 292. The control device 25 is in communication with the motor 306 for controlling and for monitoring the motor 306. The memory 27 and/or processor 30 may accordingly be configured to control raising and lowering of the seat 312 in accordance with some example embodiments. Suitable motors 306 include, but are not limited to, servo motors, stepper motors and DC motors. The housing 304 extends downwardly from the bracket 310 and has a central passageway which aligns with the aperture 311. The actuating rod 308 is mounted in the housing 304 and extends through the aperture 311. The actuating rod 308 can be translated upwardly and downwardly within the housing 304 by the motor 306. When the actuating rod 308 is lifted sufficiently upward relative to a position of the seat 212, the end of the actuating rod 308 engages the underside of the seat 312 to move the seat 312 upwardly relative to the mounting bracket 296 in the directions of arrows 292.

The seat 312 is formed as a block and has a pocket 318, such as a V-shaped pocket, in its upper end thereof into which the workpiece 22 seats as described herein. The second lift assembly 298 further includes a sensor 320 provided therein, which may be mounted in the seat 312. The sensor 320 is used to determine whether the workpiece 22 is seated on the seat 312, and further used to determine when an end of the workpiece 22 is positioned proximate to the sensor 320. The sensor 320 is in communication with the control device 25 and can be embodied as any of a variety of sensors capable of detecting presence and/or proximity of a workpiece 22, such as by way of non-limiting example, a laser sensor.

The second assembly 206*b* includes a horizontal mounting bracket 322, and a lift assembly 324 attached to the mounting bracket 322. A pair of apertures 326, 328 are provided through the mounting bracket 322.

The lift assembly 324 includes a vertical housing 330 attached to the mounting bracket 322, a motor 338, and an actuating rod 336 in the housing 330 which is in communication with the motor 338 and extends through the aperture 326 in the mounting bracket 322. The lift assembly 324 further includes a seat 334 which seats on top of the bracket 322, and an elongated tube 332 which extends from the lower surface of the seat 334 and through aperture 328 in the mounting bracket 322. The lift assembly 324 is used to raise and lower the seat 334 toward/away from the mounting bracket 322 in the direction of arrows 292. The control device 25 is in communication with the motor 338 for controlling the motor 338 and for monitoring the motor 338. The memory 27 and/or processor 30 may accordingly be configured to control raising and lowering of the seat 334 in accordance with some example embodiments. Suitable motors 338 include, but are not limited to, servo motors, stepper motors and DC motors. The housing 330 extends downwardly from the mounting bracket 322 and has a central passageway which aligns with the aperture 326. The actuating rod 336 is mounted in the housing 330 and extends through the aperture 326. The actuating rod 336 can translate upwardly and downwardly within the housing 330 using the motor 338. When the actuating rod 336 is lifted sufficiently upward relative to a position of the seat 334, the end of the actuating rod 336 engages the underside of the seat 334 to move the seat 334 upwardly relative to the mounting bracket 322 in the directions of arrows 292. The seat 334 has a pocket 340, such as a V-shaped pocket, in its upper end thereof into which the workpiece 22 seats as described herein.

The bending carousel apparatus 208, see FIGS. 24-32, contains all of the components to form bends in the workpiece 22. The bending carousel apparatus 208 generally includes a carousel frame 344 which is capable of movement relative to the second frame assembly 212, a motor 238 for rotating the carousel frame 344 relative to the second frame assembly 212, shoe assemblies 346*a*-346*c* mounted on the carousel frame 344 and a motor 228, and a carousel lifting assembly 345 for lifting the carousel frame 344 away from and toward the second frame assembly 212. The control device 25 is in communication with motor 228 for controlling and for monitoring the motor 228. The memory 27 and/or processor 30 may accordingly be configured to control rotation and/or lifting of the carousel frame 344 in accordance with some example embodiments. For example, the control device 25 of some example embodiments is configured to control and monitor the motor 228 based on data that is inputted to the control device 25, e.g., the data that the application 901 automatically determined from architectural drawings for controlling the bending carousel apparatus 208 to bend the workpieces 22. The appropriately shaped workpieces 22 may then be shipped to the construction site for assembly, e.g., for use with prefabricated assembly and subassembly construction. Suitable motors for moving the bending carousel apparatus 208 include, but are not limited to, servo motors, stepper motors and DC motors.

Figure 27:
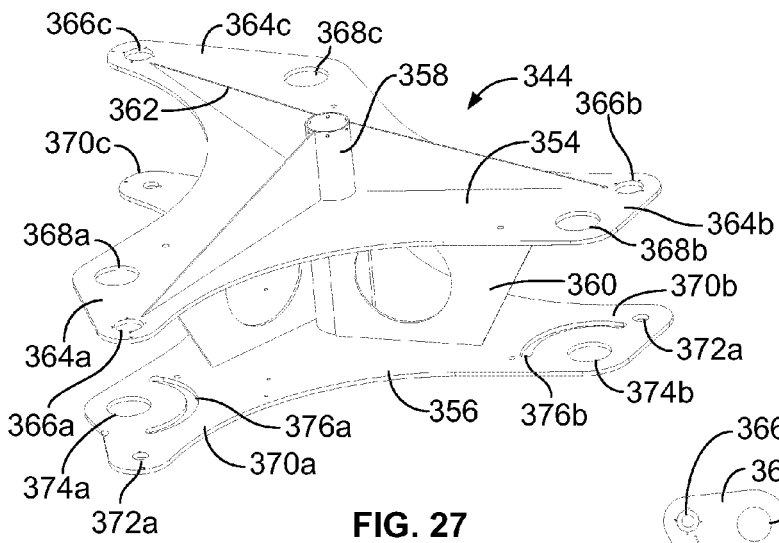
FIG. 27 is a perspective view of a carousel used in the automated bender.
Figure 28:
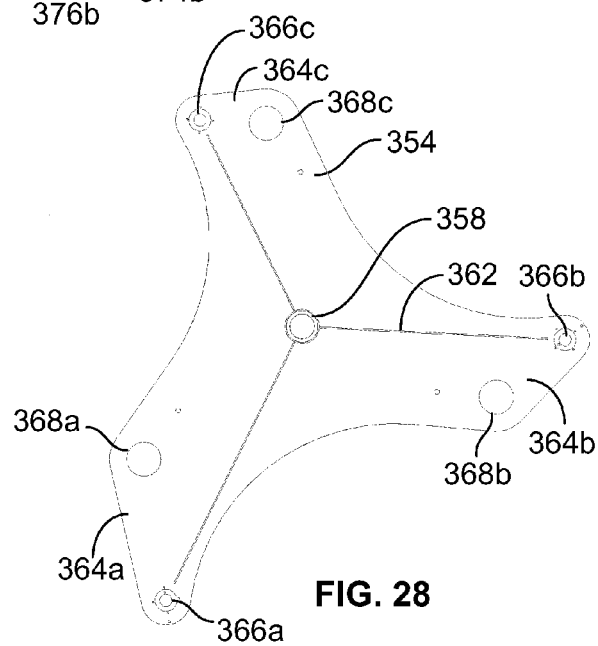
FIG. 28 is a bottom plan view of the carousel.
Figure 29:
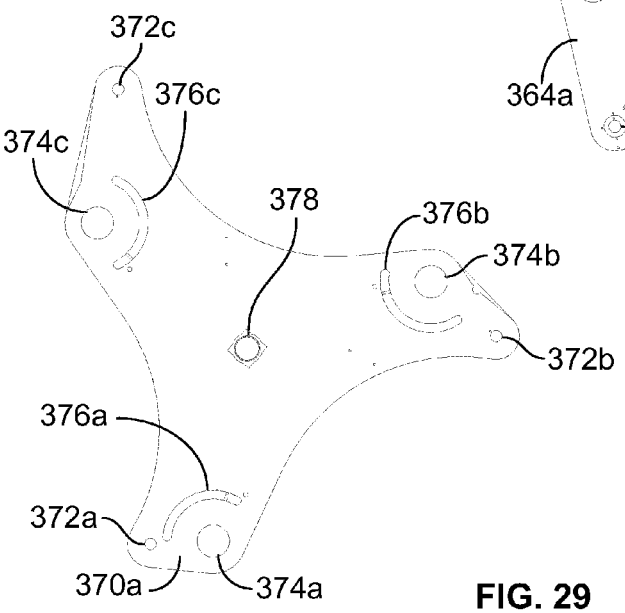
FIG. 29 is a top plan view of the carousel.

As best shown in FIGS. 27-29, the carousel frame 344 has an upper plate 354, a lower plate 356 spaced away from the upper plate 354 by a vertical central tube 358, and a plurality of vertical supports 360 extending between the plates 354, 356 and radiating outwardly from the central tube 358. The central tube 358 extends upwardly from the upper plate 354, and a cap 386 is affixed to the top of the central tube 358 for closing the end of the central tube 358. A plurality of ribs 362 are provided on the upper plate 354 and radiate outwardly from the central tube 358. The central tube 358 has a passageway extending therethrough which is closed at one end by the cap 386. The shoe assemblies 346a-346c are mounted on the carousel frame 344 between the upper and lower plates 354, 356 at spaced apart locations. The shoe assemblies 346a-346c rotate relative to the carousel frame 344, and are independently rotatable relative to each other. While three shoe assemblies 346a-346c are shown and described, it is to be understood that two spaced apart shoe assemblies, or more than three spaced apart shoe assemblies can provided on the carousel frame 344. In addition, while as shown and described herein that the upper and lower plates 354, 356 of the carousel frame 344 are formed of a triangular shape having arms 364a-364c, 370a-370c, the upper and lower plates 354, 356 could instead by circular or take any other suitable shape, provided the shape allows for the spacing of the shoe assemblies. The triangular shape shown herein reduces the weight of the carousel frame 344.

As shown, the upper plate 354 is generally triangular and is formed from arms 364a-364c extending radially outwardly from the central tube 358. Each arm 364a-364c has a pair of spaced apart apertures 366a-366c, 368a-368c provided at the ends thereof. The central tube 358 extends through an aperture in the center of the upper plate 354. As shown, the lower plate 356 is generally triangular and is formed from arms 370a-370c extending radially outwardly from the central tube 358. Each arm 370a-370c has a pair of spaced apart apertures 372a-372c, 374a-374c and an curved slot 376a-376c provided at the ends thereof. The slots 376a-376c are radially inwardly of the apertures 372a-372c, 374a-374c. A square central aperture 378 is provided in the center of the lower plate 356 and aligns with the passageway through the central tube 358.

Figure 26:
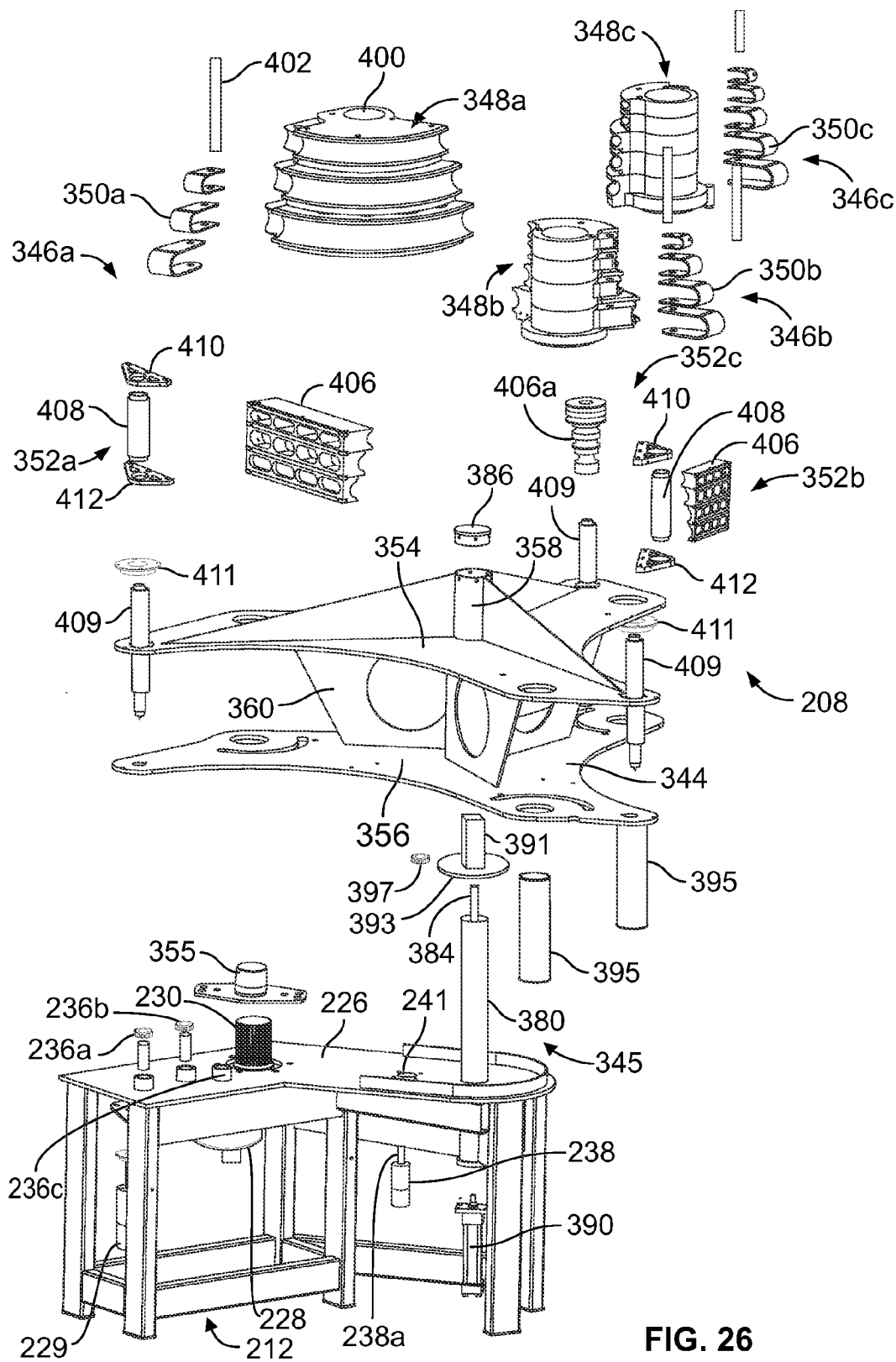
FIG. 26 is an exploded perspective view of a portion of the automated bender.

The carousel lifting assembly 345, see FIG. 26, lifts the carousel frame 344 away from the top plate 226 of the second frame assembly 212. The carousel lifting assembly 345 is attached to the second frame assembly 212 and includes a shaft 380 and a motor 390 and its actuating rod 384. The shaft 380 extends through the aperture 240 in the top plate 226, through the central aperture 378 in the lower plate 356 and through the central tube 358. The shaft 380 is affixed to the underside of the top plate 226 of the second portion 226b. The motor 390 is mounted to the lower end of the shaft 280 and the actuating rod 384 extends from the motor 390 and through the shaft 380. The end of the actuating rod 384 abuts against the cap 386. The control device 25 is in communication with the motor 390 for controlling and for monitoring the motor 390. The memory 27 and/or processor 30 may accordingly be configured to control movement of the carousel lifting assembly 345 for purposes of lifting the carousel frame 344 in accordance with some example embodiments. Suitable motors 390 include, but are not limited to, servo motors, stepper motors and DC motors.

To lift the carousel frame 344 relative to the top plate 226, the motor 390 moves the actuating rod 384 vertically upwardly in the direction of arrow 293. The engagement of the end of the actuating rod 384 with the underside of the cap 386 move the carousel frame 344 upwardly relative to the top plate 226 of the second frame assembly 212. The carousel frame 344 can be pivoted when in a raised position.

The carousel frame 344 can be rotated relative to the second portion 226b of the top plate 226. The carousel frame 344 may be rotated around a vertical axis when in a raised position to rotate the shoe assemblies 346a-346c to the operating position, e.g., based on the type of workpiece 22 to be shaped. To effect this rotational movement, a rotation tube 391 seats around the shaft 380. The rotation tube 391 can rotate relative to the shaft 380, and has a lower plate 393 which has a circular profile and an upstanding tube 295 which has square exterior profile. The lower plate 393 has a plurality of teeth on its periphery. The shaft 380 extends through an aperture in the lower plate 393 and through a passageway in the tube 295. The rotation tube 391 extends through the square central aperture 378 in the lower plate 358. Thus, the rotation tube 391 cannot rotate relative to carousel frame 344. The motor 238 is affixed to the underside of the top plate 226 and a drive shaft 238a of the motor 238 extends through the opening 241 and engages with a gear 397. The gear 397 is coupled to the lower plate 393 by a drive chain (not shown).

When the motor 238 is actuated, its drive shaft 238a rotates the gear 397 which rotates the chain, which in turn, rotates the rotation tube 391. This causes the carousel frame 344 to rotate. The carousel frame 344 is rotated when the carousel frame 344 is in the up position (when raised by the carousel lifting assembly 345). The control device 25 may be in communication with the motor 238 such that the memory 27 and/or processor 30 may be configured to control rotation of the rotation tube 391 for purposes of carousel frame 344.

Each shoe assembly 346a-346c includes a bending shoe 348a-348c, saddles 350a-350c, and a follower assembly 352a-352c to provide proper bend to the workpiece 22, e.g., based on the data indicating the size of the workpiece 22, see FIG. 26. As shown and described herein, three sets of shoes/saddles/follower assemblies are provided, however, it is to be understood that at least two sets are to be provided, but more than three sets can be provided. The shoe assemblies 346a-346c are mounted between the plates 354, 356 of the carousel frame 344. Shoe 348a is proximate to follower assembly 352a; shoe 348b is proximate to follower assembly 352b; shoe 348c is proximate to follower assembly 352c. Shoe 348a and its follower assembly 352a are mounted between arms 364a, 370a; shoe 348b and its follower assembly 352b are mounted between arms 364b, 370b; shoe 348c and its follower assembly 352c are mounted between arms 364c, 370c.

Figure 30:
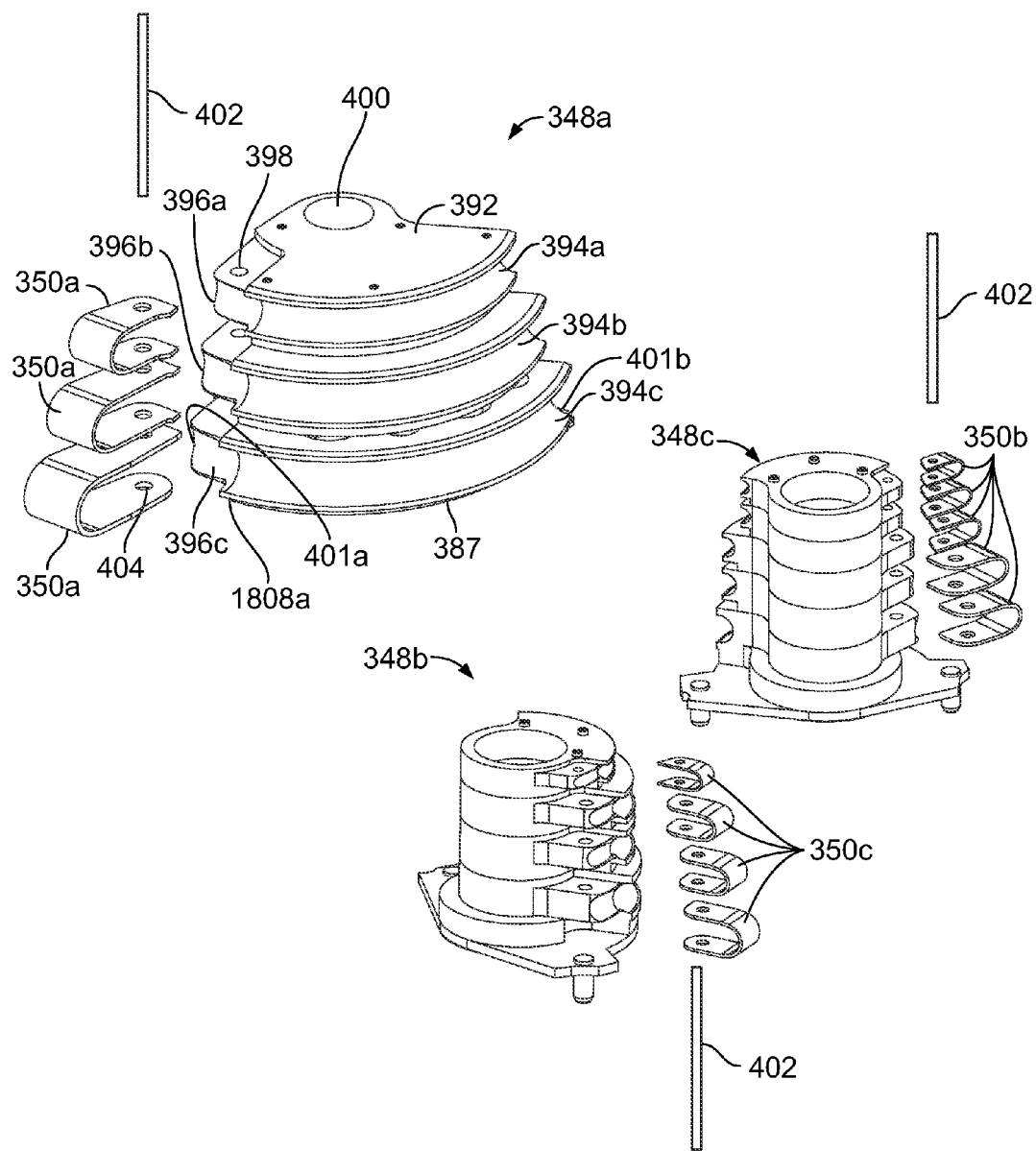
FIGS. 30 and 31 are exploded perspective views of a portion of the automated bender.

As shown in FIGS. 26 and 30, shoe 348a is formed from a body 392 having a plurality of arc-shaped channels 394a-394c in a side surface thereof, an arc-shaped bearing surface 387 extending downwardly from the lowest arc-shaped channel 394d, and a vertical pivot tube 395 which attaches the body 392 to the carousel frame 344.

The channels 394a-394c are horizontal, are stacked on top of each other, and are offset vertically from each other. Each channel 394a-394c has a first end 401a and a second end 401b. A reduced height shoulder 396a-396c is provided at the first end 401a of each channel 394a-394c. A vertical passageway 398 extends through each shoulder 396a-396c and the passageways 398 are aligned with each other. A vertical passageway 400 extends from a top surface of the body 392 to a bottom surface of the body 392. The shoe 348a may be formed of a unitary body, or may be formed of a plurality of bodies stacked on top of each other. When formed of a plurality of bodies, each body has a channel, a shoulder and a passageway; the channels are stacked on top of each other, and the passageways align with each other. The channels 394a-394c have different diameters so that a variety of workpieces can be accommodated.

As shown in FIG. 30, the arc-shaped bearing surface 387 preferably has the same radius of curvature as the lowest arc-shaped channel 394d. The arc-shaped bearing surface 387 has a first end 387a and an opposite second end 387b. The first end 387a is provided proximate to the first end 401a of the channels 394a-394c and the second end 397a is provided proximate to the second end 401b of the channels 394a-394c.

Figure 31:
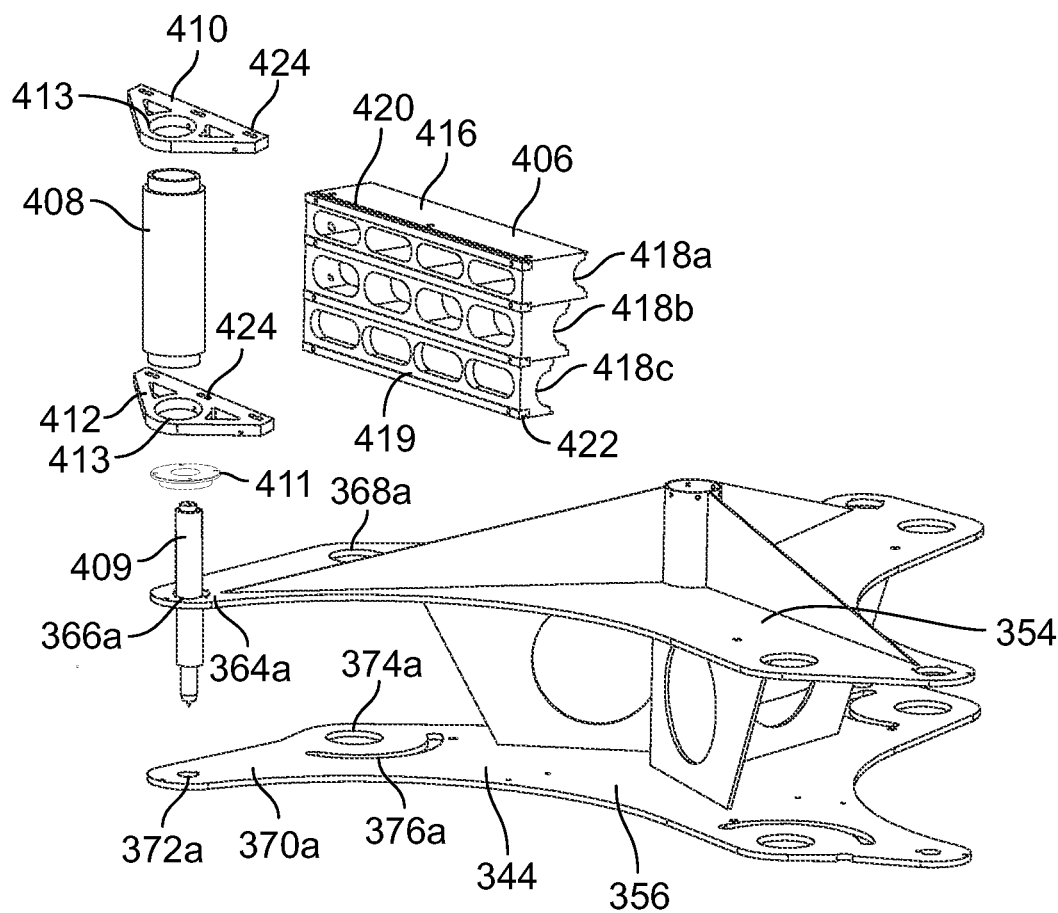
Figure 32:
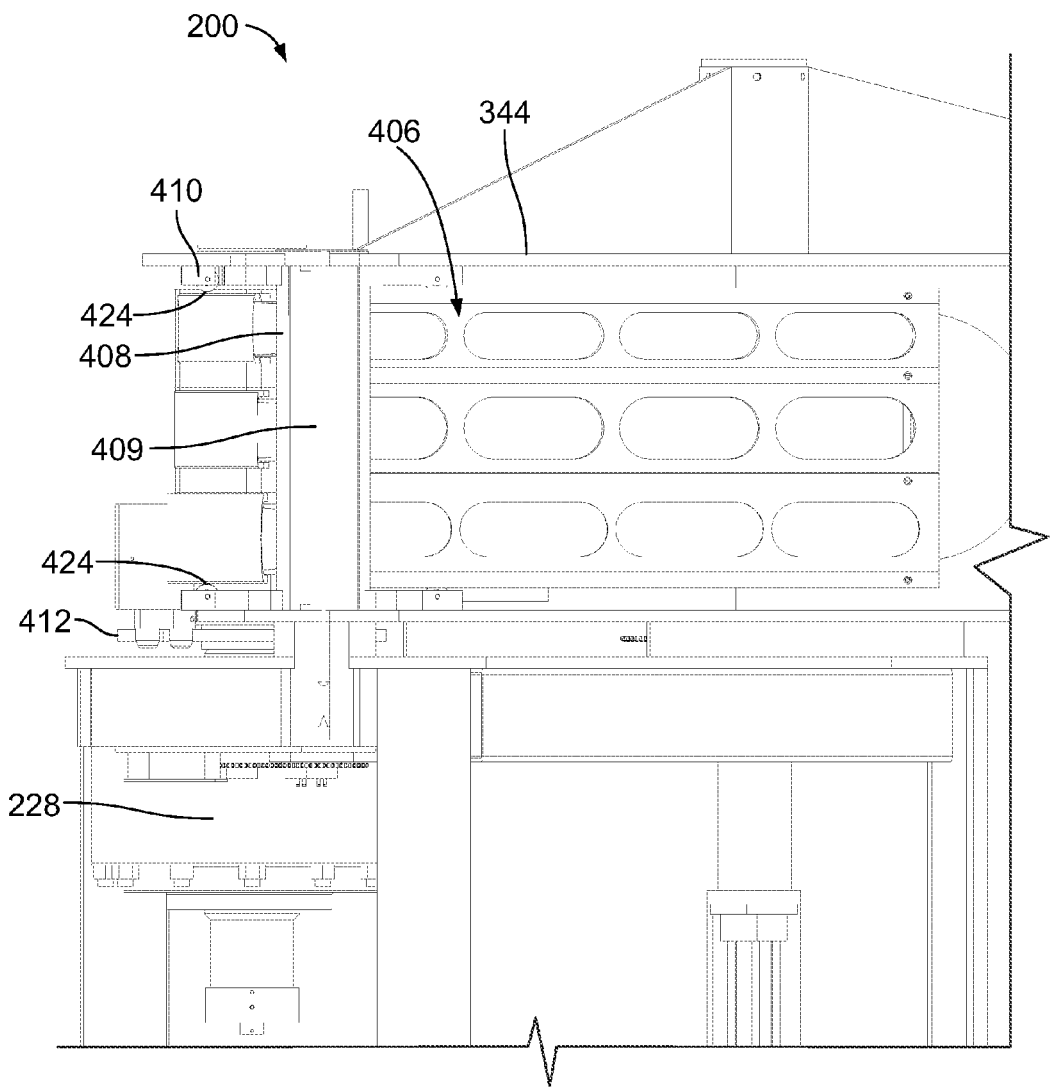
FIG. 32 is a cross-section view of a portion of the automated bender.

As shown in FIG. 26, the shoe 348a is attached to the carousel frame 344 by the pivot tube 395 extending through the aligned apertures 368a, 374a, see FIG. 31, in the plates 354, 356 of the carousel frame 344 and through the passageway 400. In use, the shoe 348a rotates relative to the pivot tube 395.

A U-shaped saddle 350a is pivotally attached to each shoulder 396a-396c. A pivot rod 402 extends through the passageway 398 and through apertures 404 in the saddles 350a to attach the saddles 350a to the shoulders 396a-396c. Each saddle 350a can include a spring (not shown) for causing the saddle 350a to resume its initial position. As shown, three channels 394a-394c and saddles 350a are provided in shoe assembly 346a.

As best shown in FIGS. 26 and 31, each follower assembly 352a-352c includes a follower bar 406, a roller 408 having an eccentric shaft 409 mounted therein, an upper track member 410, a lower track member 412. A motor 229 is used to drive the follower assembly 352a-352c as described herein.

The follower bar 406 is formed of a body 416 having a first end 416a and a second end 416b having elongated, horizontal, linear channels 418a-418c formed on one side thereof and having a planar opposite side 419. The channels 418a-418c are stacked on top of each other. An upper track 420 is formed in the top surface of the body 416 proximate to the planar side 419, and a lower track 422 is formed in the lower surface of the body 416 proximate to the planar side 419. Each channel 418a-418c is arc-shaped and has a diameter that matches the channels 394a-394c of the shoe 348a-348c.

The track members 410, 412 are formed from plates, which as shown are generally triangular but may take other shaped, having a plurality of wheels 424 mounted thereon. Each track member 410, 412 has an aperture 413 therethrough. The ends of the roller 408 seat within the apertures 413, and the roller 408 can rotate relative to the track members 410, 412.

The shaft 409 extends through the aperture 366a in arm 364a, through aperture 413 in upper track member 410, through the roller 408, through aperture 413 in track member 412, through the aperture 372a in arm 370a, and extends downwardly from the arm 370a. A cap 411 is attached to the top end of the shaft 409 and secured to plate 354. When the eccentric shaft 409 is rotated as discussed herein, the roller 408 is rotated relative to the track members 410, 412.

As shown in FIG. 1, the planar side 419 of the body 416 engages against the roller 408, and the wheels 424 on the track members 410, 412 engage within the tracks 420, 422 on the body 416. The following description is directed to shoe 348a, for the ease in description of the invention. It is be understood that this description applies to shoes 348b and 348c. The body 416 is positioned between the roller 408 and the shoe 348a. In an initial position, the follower bar 406 is positioned proximate to the channels 394a-394c of the shoe 348a such that the saddles 350a are proximate to the first end 416a of the follower bar 406. The body 416 can translate relative to the roller 408.

Shoe assembly 346b is identically formed to that of shoe assembly 346a, except that four channels are provided in the shoe 348b and in the follower assembly 352b, that the diameters of the channels in the shoe 348b and in the follower assembly 352b are different than those of the shoe 348a and the follower assembly 352a, and that a spacer 349 is mounted between the upper track member 410 and the arm 354b of the carousel frame 344. The spacer 349 is provided since the shoe 348b and the follower assembly 352b are shorter than the shoe 348a and the follower assembly 352a.

The shoe 348c in shoe assembly 346c is identically formed to that of shoe assembly 346a, except that five channels are provided in in the shoe 348c and in the follower assembly 352c, that the diameters of the channels in the shoe 348c and in the follower assembly 352c are different than those of shoes 348a, 348b and follower assemblies 352a, 352b, that the arc-shaped bearing surface 387 may be eliminated, and that a spacer 351 is mounted between the upper track member 410 and the arm 354c of the carousel frame 344. The spacer 351 is provided since the shoe 348c and the follower assembly 352c are shorter than the shoe 348a and the follower assembly 352a. In shoe assembly 346c, the diameters of the channels are smaller. As a result, the bar-shaped follower bar 406 may be replaced by a circular follower tube 406a that has a plurality of horizontal channels provided therein, however, a follower bar 406 like those used with shoe assemblies 346a, 346b may be provided.

The channels in the various shoe 348a-348c and follower assemblies 352a-352c are sized to accept a variety of workpiece diameters. As a result, some of the channels can be used to bend rigid or intermediate metal conduit (IMC) type conduit, and others are used to bend electrical metallic tubing (EMT) type conduit.

Figure 25:
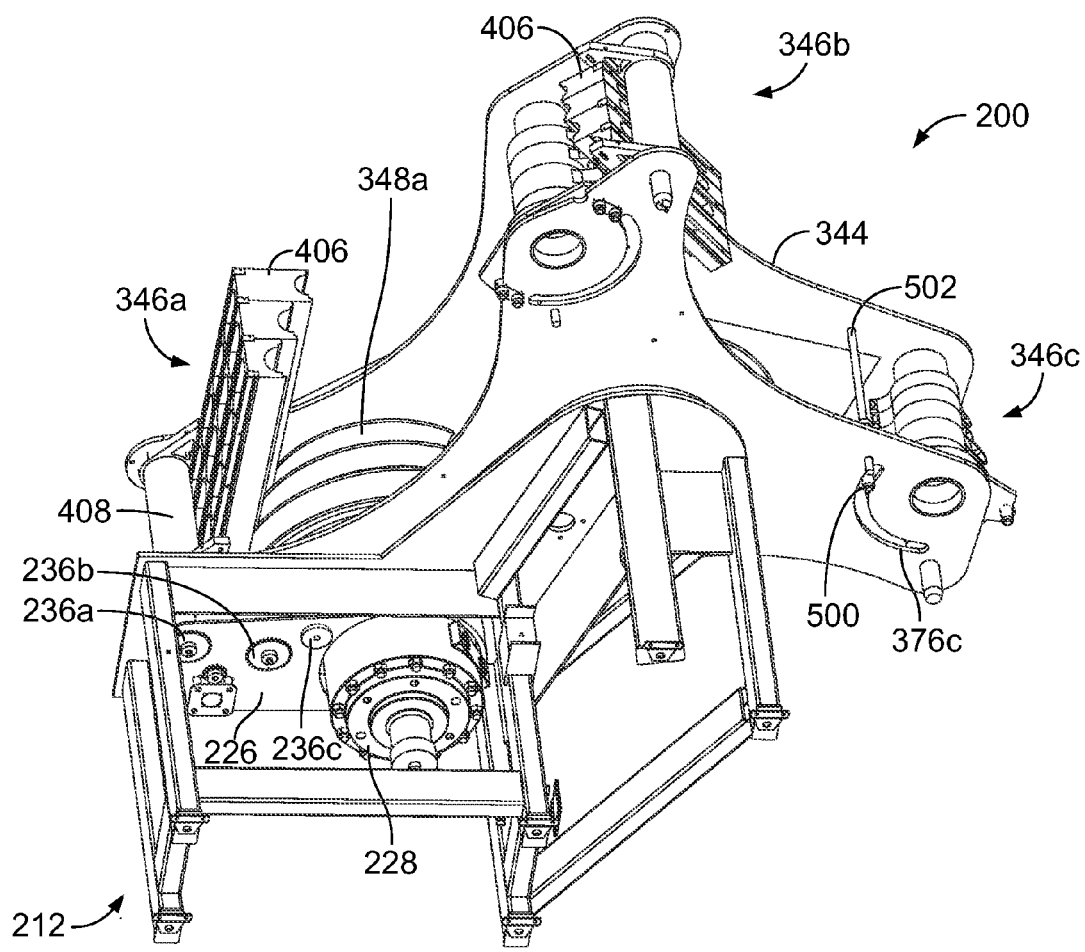

Motor 228, see FIG. 25, is attached to an underside of the top plate 226 of the first portion 226a. The drive shaft 230 of the motor 228 extends through the aperture 232 in the first portion 226a and mates with a drive hub 355 which engages with the pivot tube 395 when the respective shoe assembly 346a, 346b, 346c is positioned over the motor 228 in the bending position. When the motor 228 is actuated, the pivot tube 395 is rotated in the direction of arrows 389, see FIG. 3, to rotate the respective shoe 348a, 348b, 348c.

The control device 25 (e.g., the memory 27 and/or processor 30) controls and monitors the motors 228, 229 based on data that is inputted to the control device 25, e.g., the data that the application 901 automatically determined from architectural drawings for controlling the bending carousel apparatus 208 to bend the workpieces 22. The motor 229 is attached to an underside of the top plate 226 of the first portion 226a. The motor 229 drives gearing 236a-236c associated with apertures 234a-234c, The gearing 236a-236c mates with the shaft 409 when the respective shoe assembly 346a, 346b, 346c is positioned over the motor 229 in the bending position. When the motor 229 is actuated, the eccentric shaft 409 is rotated. This action causes the body 416 of the follower bar 416 to linearly translate towards or away from the shoe 348a-348c.

In use, the user programs into the control device 25 the size of the workpiece 22 to be clamped by the clamping apparatus 20, the type of workpiece 22 (for example IMC conduit) and the types of bends to be made to the workpiece 22 by the bending carousel apparatus 208. As a result of the programming, the carousel frame 344 is lifted upwardly by the carousel lifting assembly 345 and rotated until the arm, for example arm 364a, containing the proper channel is positioned over the bending position, that is, the position above the motors 228, 229. The carousel frame 344 is then lowered by carousel lifting assembly 345. When lowered, the shaft 409 of the follower assembly, for example follower assembly 352a, engages with the appropriate gearing, for example gearing 236a, on the second frame assembly 212, and the pivot tube 395 engages with the drive shaft 230 of the motor 228.

In an initial state, the first and second assemblies 206a, 206b forming the workpiece holding apparatus are positioned at its lowest position so that a user can easily seat a workpiece 22 thereon, the seats 312, 334 are aligned, and the clamping apparatus 20 is aligned with the seats 312, 334. The pockets in the seats 312, 334 securely hold the workpiece 22 on the seats 312, 334. After the workpiece 22 is placed onto the first and second assemblies 206a, 206b, the lift assemblies 298, 324 are actuated to lift the seats 312, 334 upwardly to align the end of the workpiece 22 with the working centerline that passes through the center of the openings 64, 90 of the clamping apparatus 20. The control device 25 is programmed to determine a distance the workpiece 22 is to be lifted by the first and second assemblies 206a, 206b so that the workpiece 22 can be inserted into the clamping apparatus 20.

The clamping apparatus 20 is then moved in the direction of arrow 254 to effect entry of the end of the workpiece 22 into the clamping apparatus 20. The stop plate 125 prevents the workpiece 22 from contacting the drive shaft 126. A plurality of mounts 140 are mounted on the flat side surface 82b of actuator plate 48 by fasteners 142. Each mount 140 is formed as a block and has a tapered surface 144 which tapers inwardly toward the opening 90. When the workpiece 22 is inserted into the clamp assembly 44, if the workpiece 22 is off-center, the workpiece 22 will engage the tapered surface(s) 144 of the mount(s) 140 and the tapered surface(s) 144 direct the workpiece 22 into the opening 90. The workpiece 22 is inserted until the end of the workpiece 22 engages against the base plate 120 of the frame 110.

The clamping apparatus 20 is then engaged with the end of the workpiece 22. Rotation of the motor 104 causes drive rod 100 to rotate which moves drive coupling 102 along the drive rod 100, which imparts rotational movement to the actuator plates 48, 52, and inward radial movement of the drive fasteners 56a, 56b, 56c, 59a, 59b, 59c and a corresponding inward pivoting movement of the jaws 46a, 46b, 46c, 50a, 50b, 50c, toward the center of the clamp assembly 24 via the movement of the pivot fasteners 54a, 54b, 54c in their slots 92a, 92b, 92c. This inward pivoting movement of the jaws 46a, 46b, 46c, 50a, 50b, 50c moves them into an aligned gripping engagement with the end of the workpiece 22. The serrations on the workpiece engaging surface 74 may bite into the workpiece 22 to secure the workpiece 22 in the clamp assembly 24, thereby preventing the workpiece 22 from slipping in the jaws 46a, 46b, 46c, 50a, 50b, 50c. When the current draw sensor and the distance sensor indicate that the appropriate clamping force on the workpiece 22 has been achieved, the control device 25 sends a signal to stop actuation of the motor 104. If the incorrect size of the workpiece 22 has been programmed into the control device 25, the control device 25 will be able to determine this because the programmed current draw level and distance travel amount would not be properly reached or will be exceeded. If the control device 25 determines that an incorrect workpiece size has been programmed, the user may be notified and asked to verify the size of the workpiece 22. In addition, if the workpiece 22 is galvanized, as the jaws 46a, 46b, 46c, 50a, 50b, 50c, engage with the workpiece 22, the galvanization may wear away and cause the jaws 46a, 46b, 46c, 50a, 50b, 50c, to slip on the surface of the workpiece 22. In some embodiments, if such slippage occurs and provided the current and travel limits have not yet been reached, then the clamping apparatus 20 is directed by the control device 25 to continue clamping the workpiece 22. The workpiece 22 will re-center in the clamp assembly 24. The control device 25 is programmed to determine the appropriate amount of current draw on the motor 104 and the distance that the drive coupling 102 will travel along the drive rod 100 to achieve the desired clamping force on the workpiece 22.

To ensure that the clamping apparatus 20 has the required amount of clamping force to rotate the workpiece 22 using the drive mechanism 26, the control device 25 determines the current draw and the distance travel amount from the motor 104. These parameters are monitored by the control device 25 and if at any time the parameters are outside of the requirements for the workpiece 22, the operation will stop. This aids in preventing damage to the clamping apparatus 20 as well as to the workpiece 22. For example, if a workpiece 22 having a 4" outer diameter is expected by the program in the control device 25, and a workpiece 22 having a 1" outer diameter is inserted into the clamping apparatus 20, when the expected distance travel is met, but the current draw is not met, then the control device 25 is programmed to notify the user that there is an issue. Likewise, if a workpiece 22 having a 1" outer diameter is expected by the program in the control device 25, and a workpiece 22 having a 4" outer diameter is inserted into the clamping apparatus 20, when the expected current draw is met, but the distance measurement is not met, then the control device 25 is programmed to notify the user that there is an issue.

As an alternative, the size of the workpiece 22 is not programmed into the control device 25 by the user. Instead, the control device 25 determines the size of the workpiece 22 by monitoring the current draw and the distance measurement and comparing this information to known parameters for workpiece sizes stored in the memory 27.

Once the workpiece 22 is gripped by the clamping apparatus 20, the clamping apparatus 20 is retracted in the direction of arrow 254 until the sensor 320 in the first assembly 206a of the workpiece holding apparatus 296 indicates that the end of the workpiece 22 has been detected. Thereafter, the lift assembly 324 of the second assembly 206b is retracted downwardly such that the seat 334 is not engaged with the workpiece 22. The workpiece 22 remains supported at its front end by the first assembly 206a and at its rear end by the clamping apparatus 20.

Next, the workpiece 22 is moved to the aligned position with the channel, for example channel 394a, that has been designated in the bending carousel apparatus 208 (channel 418a and shoe assembly 346a are used in the following description, but it is to be understood that it is only illustrative). The carriage assembly 204 is moved in the direction of arrow 274 to be behind the bending carousel apparatus 208. This first assembly 206a slides along the tubes 294. Thereafter, the first lift assembly 295 of the first assembly 206a is actuated to raise the second lift assembly 298 relative thereto, and the second mount 280 of the carriage assembly 204 is raised to align the end of the workpiece 22 seated on the first assembly 206a with the position where the desired channel 394a is located. The first lift assembly 296 is actuated to lift the second lift assembly 298 relative to the mounting bracket 296 to align the end of the workpiece 22 with the desired channel 394a.

The workpiece 22 is introduced into the corresponding channel 418a of the follower bar 406 by moving the clamping apparatus 20 toward the shoe assembly 346a. By continuing movement of the clamping apparatus 20 in this same direction, the workpiece 22 travels along the channel 418a of the follower bar 406 and travels between the channel 418a in the follower bar 406 and the channel 394a in the shoe 348a. The workpiece 22 is advanced along the channels 418a, 384a until the workpiece 22 passes between the shoulder 396a and the saddle 350a. Once the control device 25 has determined that the workpiece 22 has been advanced to the position where the bend is to be effected, the lift assembly 206a then drops out of position and returns back to where it started. If needed, motor 229 is actuated to rotate the eccentric shaft 409, linearly translating the roller 408 and follower bar 406 towards the shoe 348a. The motor 228 is actuated to rotate the shoe 348a. The shoe 348a starts to rotate and the saddle 350a engages with the workpiece 22. As the shoe 348a continues to rotate, the follower bar 406 translates linearly and "squeezes" the workpiece 22 between the shoe 348a and the follower bar 406. It is to be noted that the squeeze is effected with workpieces 22 that are formed of thin wall conduit, tube and pipe. This creates the desired bend in the workpiece 22. A pin 500 is attached to the bottom of the respective shoe 348a-348c and seats within the respective arcade slot 376a-376c to limit the rotational movement of the shoe 348a relative to the carousel frame 344. A stop bar 502 is also provided between each of the arms 364a, 370a; 364b, 370b; 364c, 370c for preventing the rotational movement of the shoes 348a-348c relative to the carousel frame 344 when the carousel 334 is being rotated in the air.

After the bend is completed, motor 229 is actuated to rotate the eccentric shaft 409 and translate linearly, roller 408 and follower bar 406 away from the shoe 348a. The shoe 348a is rotated by motor 228 in the opposite direction to release the saddle 350a from engagement with the workpiece 22. The follower bar 406 also translates linearly in the reverse direction.

To form a subsequent bend in the workpiece 22, the clamping apparatus 20 is moved toward the shoe 348a until the portion of the workpiece 22 to be bent is positioned between the saddle 350a and the shoe 348a. The motor 116 is then operated to rotate the frame 110, the clamp assembly 24 and its mounted drive mechanism 26 and the attached workpiece 22 relative to the second mount 280 in either direction. The motor 116 can be used to rotate the clamp assembly 24 and its mounted drive mechanism 26 around 360 degrees. This rotation allows the workpiece 22 to be positioned in a variety of rotational positions to allow for infinitely variable bending shapes. The bending operation is then repeated.

After the desired bends have been effected in the workpiece 22, drive mechanism 26 is actuated to release the workpiece 22. The workpiece 22 is removed from the bender 200. The bender 200 is then returned to its initial position and is ready to accept another workpiece.

Figure 33:
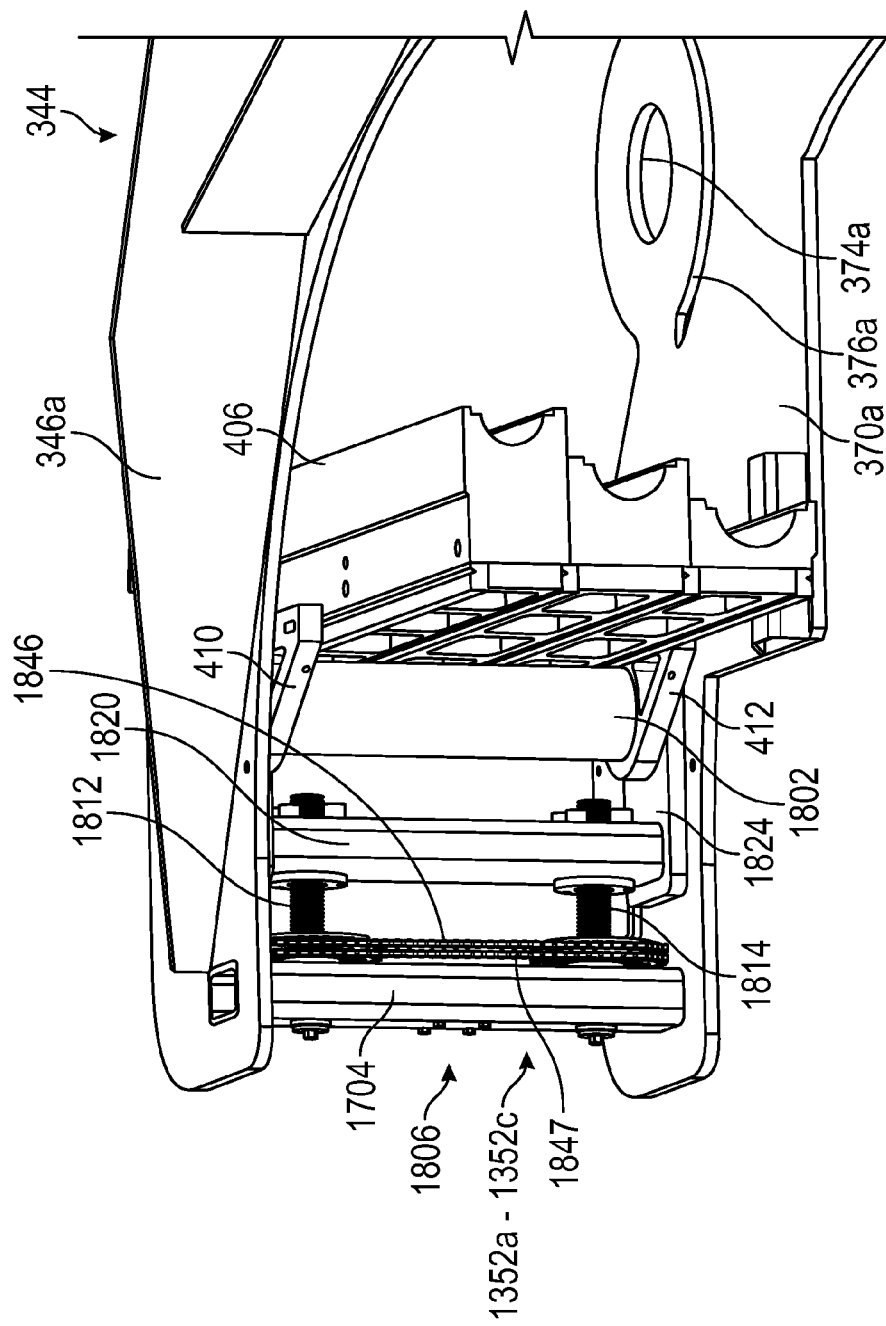
FIG. 33 is a perspective view of a portion of the carousel and a follower bar assembly used in the automated bender.
Figure 34:
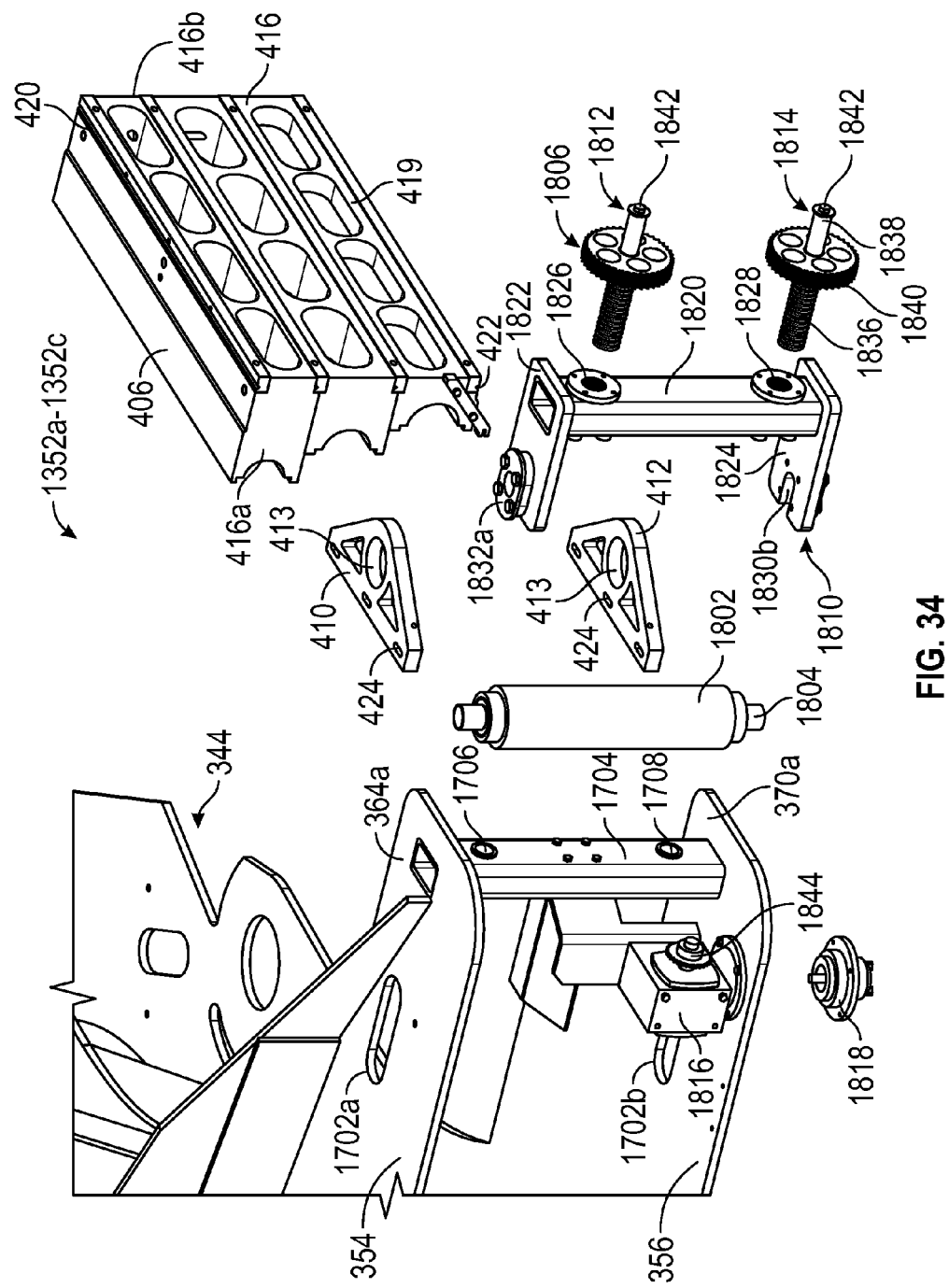
FIGS. 34 and 35 are exploded perspective views of the components of FIG. 33.
Figure 35:
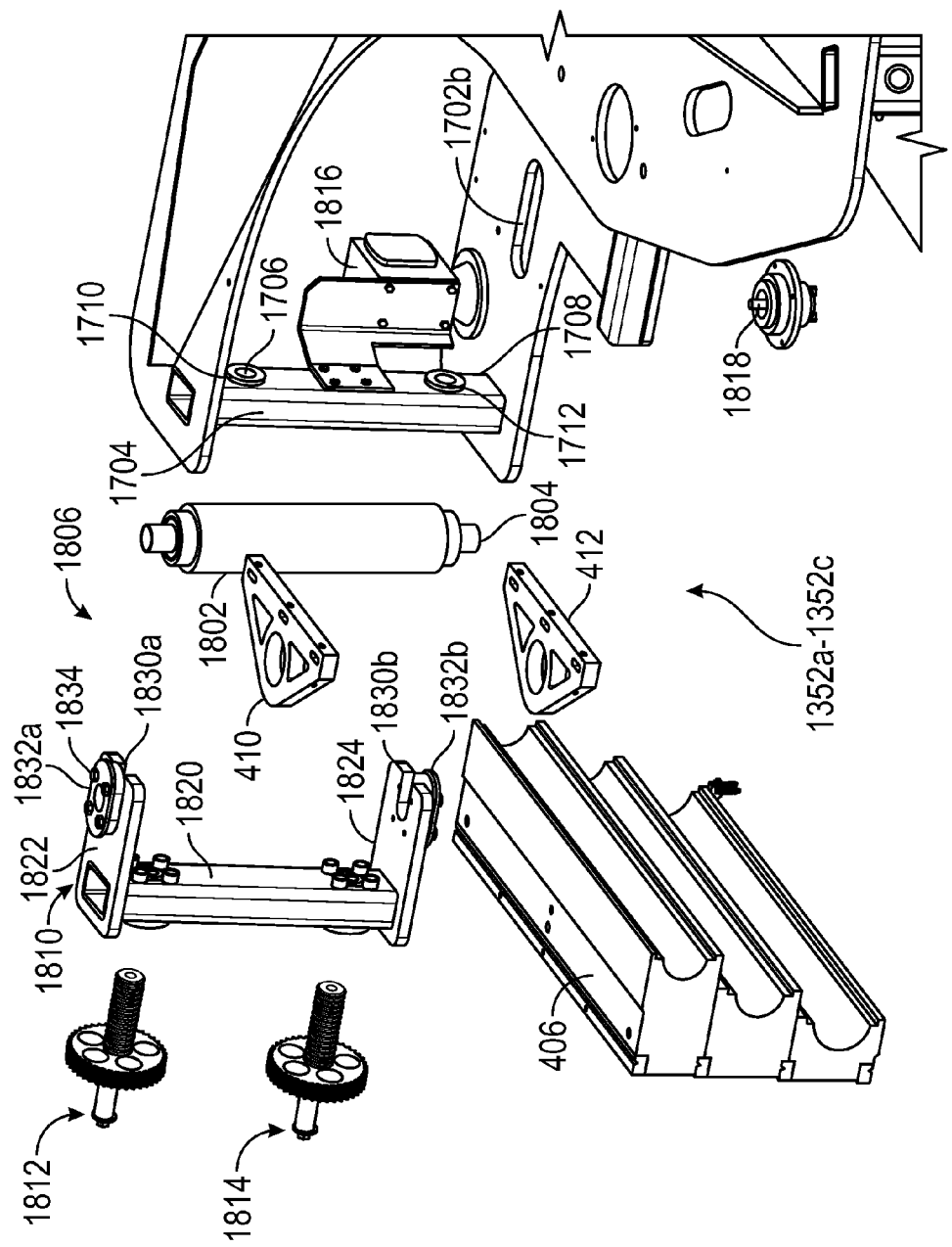

FIGS. 1, 3, 4, 25, 26, 31 and 32 show a first embodiment of the follower assembly 352a-352c. FIGS. 33-35 show a second embodiment of the follower assembly 1352a-1352c.

As shown and described herein, three sets of shoes/saddles/follower assemblies are provided, however, it is to be understood that at least two sets are to be provided, but more than three sets can be provided. The shoe assemblies 346a-346c are mounted between the plates 354, 356 of the carousel frame 344. Shoe 348a is proximate to follower assembly 1352a; shoe 348b is proximate to follower assembly 1352b; shoe 348c is proximate to follower assembly 1352c. Shoe 348a and its follower assembly 1352a are mounted between arms 364a, 370a; shoe 348b and its follower assembly 1352b are mounted between arms 364b, 370b; shoe 348c and its follower assembly 1352c are mounted between arms 364c, 370c. Each shoe 348a-348c are formed in an identical manner and attached to the carousel frame 344 by the pivot tube 395 in an identical manner to that described above. Therefore, the specifics are not repeated.

The carousel frame 344 is modified to accommodate the follower assembly 1352a-1352c of the second embodiment. An elongated slot 1702a, 1702b is provided the upper and lower plates 354, 356 of the carousel frame 344 proximate to, but spaced from, the outer end of each arm 364a-364c. The slots 1702a, 1702b are vertically aligned. A vertical frame member 1704 extends between the upper and lower plates 354, 356 proximate to, but spaced from, the outer end of each arm 364a-364c, 370a-370c. The frame member 1704 is between the end of the arms 364a-364c, 370a-370c and the elongated slots 1702a, 1702b. The frame member 1704 includes an aperture 1706 provided therethrough proximate to its upper end, and an aperture 1708 provided therethrough proximate to its lower end. A thrust bearing surface 1710, 1712 is provided on an inner surface of the frame member 1704 around the apertures 1706, 1708.

Figure 36:
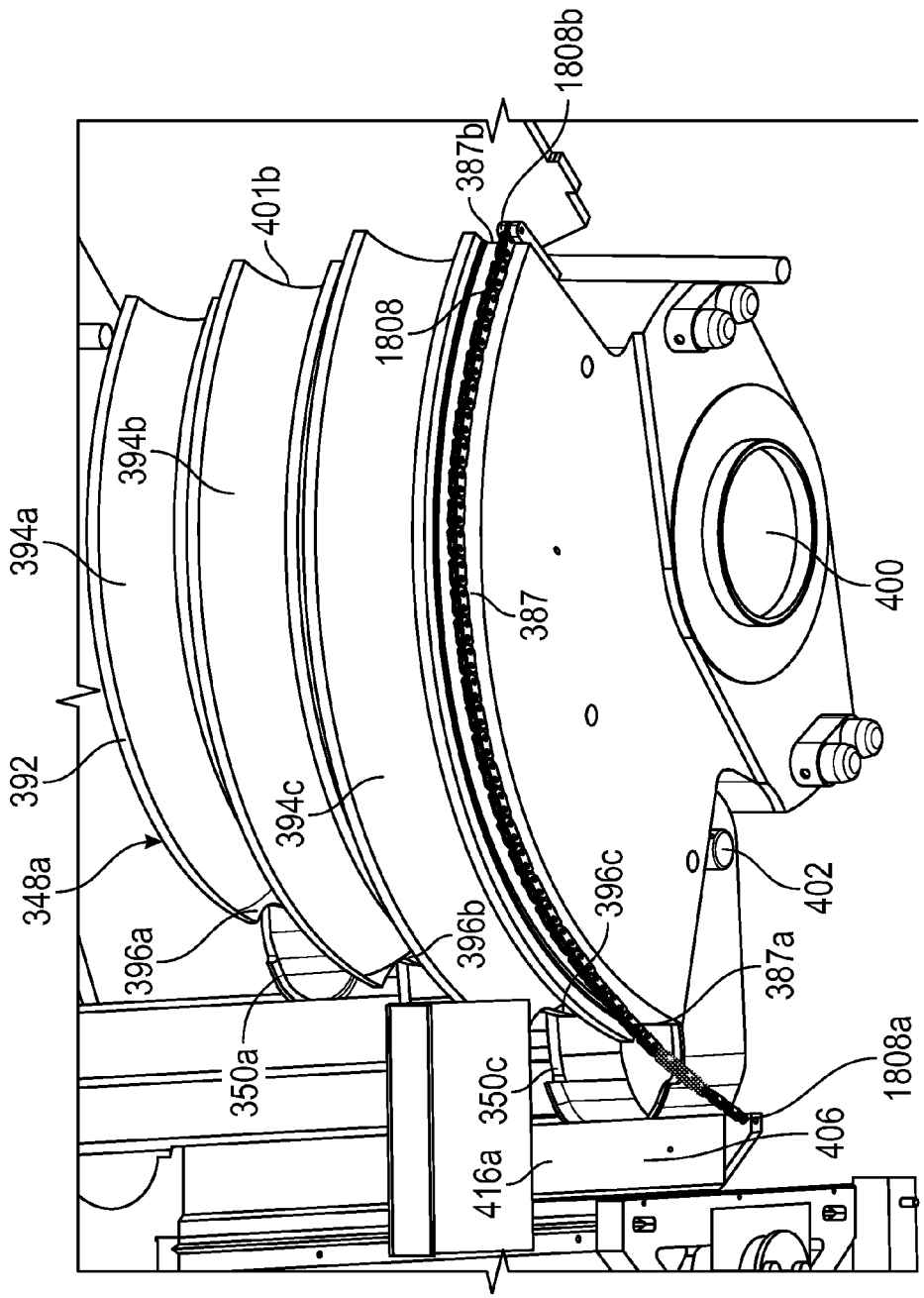
FIG. 36 is a perspective views of a shoe assembly and the follower bar assembly used in the automated bender.

The follower assembly 1352a-1352c includes the follower bar 406 and its upper and lower track members 410, 412, a roller 1802 having a shaft 1804 mounted therein, an adjustable arm assembly 1806 and a retraction member 1808, see FIG. 36, which is capable of engaging with the arc-shaped bearing surface 387 on the shoe 348a-348c. The follower bar 406 and its upper and lower track members 410, 412 are identical to that of the first embodiment and the specifics are not repeated herein.

The adjustable arm assembly 1806 includes a mount 1810 upon which the follower bar 406, its upper and lower track members 410, 412 and the roller 1802 are mounted, an upper drive member 1812 extending through the mount 1810 and engaged with the vertical frame member 1704, and a lower drive member 1814 extending through the mount 1810 and engaged with the frame member 1704. The drive members 1812, 1814 are driven by a gearbox 1816 that is powered by motor 229 via a drive hub assembly 1818 provided on the second frame assembly 212. Each drive member 1812, 1814 is preferably formed of a screw.

The mount 1810 includes a vertical base wall 1820, an upper horizontal wall 1822 extending perpendicularly from the base wall 1820, and a lower horizontal wall extending 1824 perpendicularly from the base wall 1820. Upper and lower apertures 1826, 1828 are provided through the base wall 1802 for acceptance of the threaded drive members 1812, 1814 therethrough. The upper wall 1822 has a slot 1830a extending from its free end, and a block 1832a extending upwardly from an upper surface of the upper wall 1820. The lower wall 1824 has a slot 1830b extending from its free end, and a block 1832b extending downwardly from a lower surface of the lower wall 1824. Each block 1832a, 1832b has an aperture 1834 therethrough which aligns with the slot 1830a, 1830b.

The upper end of the shaft 1804 of the roller 1802 seats in the slot 1830a and in the aperture 1834 in the block 1832a to affix the upper end of the roller 1802 to the mount 1810. The lower end of the shaft 1804 of the roller 1802 seats in the slot 1830b and in the aperture 1834 in the block 1832b to affix the lower end of the roller 1802 to the mount 1810. The roller 1802 is free to rotate relative to the mount 1810. The base wall 1820 is positioned proximate to, and inwardly of, the frame member 1704 of the carousel frame 344. The upper block 1832a seats in the upper elongated slot 1702a in the upper plate 354 of the carousel frame 344. The upper surface of the upper wall 1822 seats against the lower surface of the upper plate 354. The lower block 1832b seats in the lower elongated slot 1702b in the lower plate 356 of the carousel frame 344. The lower surface of the lower wall 1824 seats against the upper surface of the lower plate 356. Each block 1832a, 1832b has a length which is less than the length of the slot 1702a, 1702b to allow the mount 1810, the follower bar 406 and the roller 1802 to translate inwardly and outwardly relative to the shoe 348a-348c.

The planar side 419 of the body 416 engages against the roller 1408, and the wheels 424 on the track members 410, 412 engage within the tracks 420, 422 on the body 416. The body 416 is positioned between the roller 408 and the shoe 348a-348c. The follower bar 406 is positioned proximate to the channels 394a-394c of the shoe 348a such that the saddles 350a are proximate to the first end 416a of the follower bar 406. The body 416 can translate relative to the roller 1408.

The upper aperture 1706 of the frame member 1704 aligns horizontally with the upper aperture 1826 through the base wall 1820; the lower aperture 1708 of the frame member 1704 aligns horizontally with the lower aperture 1828 through the base wall 1820. The drive members 1812, 1814 are identically formed and preferably include a threaded portion 1836, an unthreaded portion 1838 extending therefrom, and an enlarged toothed sprocket 1840 extending from the juncture between the threaded portion 1836 and the unthreaded portion 1838. The unthreaded portions 1838 extends through the apertures 1706, 1708 in the frame member 1704, and are affixed to the outside of the frame member 1704 by suitable means such as nut 1842. The threaded portion 1836 extends through the apertures 1826, 1828 in the base wall 1820 of the mount 1810. The sprockets 1840 are positioned between the frame member 1704 and the base wall 1820. The mount 1810 can translate along the length of the threaded portion 1836 of the drive members 1812, 1814 to move the follower member 406 mounted thereon toward or away from the shoe 348a-346c. Preferably, each sprocket 1840 has three rows of teeth, of which only two rows are used. A chain 1846 is used on one of the rows of teeth to link drive members 1812 and 1814 together.

The gearbox 1816 mates with the motor 229 via the drive hub assembly 1818. The gearbox 1816 has a drive sprocket 1844 extending therefrom. A second chain 1847 is used on the opposing row to link drive member 1814 to drive sprocket 1844. It is to be understood that instead of providing two chains 1846, 1847 that one chain may be used to link all three sprockets 1840, 1844, with sprockets 1840 would having one row of teeth.

When the drive sprocket 1844 is driven, the chains 1846, 1847 rotate the drive members 1812, 1814 which causes the mount 1810 and follower bar 406 to linearly translate on the drive members 1812, 1814. This causes the follower bar 406 to move toward or away from the shoe 348a-348c to adjust the squeeze on the workpiece 22. The drive members 1812, 1814 are preferably designed to minimize the torque required to lower or retract the drive members 1812, 1814 under load. This may be effected by selecting a screw diameter and lead where the back drive torque created by the load is as near as possible to the frictional resistance resulting in a near zero torque to release the load.

The retraction member 1808 is formed of a high-strength, flexible member, such as a metal cable or a chain. The retraction member 1808 has a first end 1808a connected to the first end 416a of the follower bar 406 and a second end 1808b connected to the second end 387b of the arc-shaped bearing surface 387 on the shoe 348a-348c. The retraction member 1808 is capable of engaging with the arc-shaped bearing surface 387 on the shoe 348a-348c.

In use, the user programs into the control device 25 the size of the workpiece 22 to be clamped by the clamping apparatus 20, the type of workpiece 22 (for example IMC conduit, EMT conduit, or other type of conduit) and the types of bends to be made to the workpiece 22 by the bending carousel apparatus 208, and the carousel frame 344 is lifted and rotated as described previously. When the carousel frame 344 is lowered, the shaft of the gearbox 1816 engages with the drive hub assembly 1818 of the motor 229, and the pivot tube 395 engages with the drive shaft 230 of the motor 228.

The workpiece 22 is seated on the first and second assemblies 206a, 206b and fed between the carousel apparatus 208 and the appropriate follower assembly 1352a-1352c as described herein with regard to the first embodiment of the follower assembly 352a-352c. The workpiece 22 is introduced into the corresponding channel 418a of the follower bar 406 (channels 418a and shoe assembly 346a are used in the following description, but it is to be understood that it is only illustrative) by moving the clamping apparatus 20 toward the shoe assembly 346a. By continuing movement of the clamping apparatus 20 in this same direction, the workpiece 22 travels along the channel 418a of the follower bar 406 and travels between the channel 418a in the follower bar 406 and the channel 394a in the shoe 348a. The workpiece 22 is advanced along the channels 418a, 384a until the workpiece 22 passes between the shoulder 396a and the saddle 350a. Once the control device 25 has determined that the workpiece 22 has been advanced to the position where the bend is to be effected, the lift assembly 206a then drops out of position and returns back to where it started. If needed, motor 229 is actuated to linearly move the arm 1820 and the follower bar 406 thereon towards the shoe 348a to adjust the squeeze on the workpiece 22. The motor 228 is actuated to rotate the shoe 348a. The shoe 348a starts to rotate and the saddle 350a engages with the workpiece 22. As the shoe 348a continues to rotate, the follower bar 406 translates linearly and "squeezes" the workpiece 22 between the shoe 348a and the follower bar 406. It is to be noted that the squeeze is effected with workpieces 22 that are formed of thin wall conduit, tube and pipe. This creates the desired bend in the workpiece 22. The pin 500 is attached to the bottom of the respective shoe 348a-348c and seats within the respective arcade slot 376a-376c to limit the rotational movement of the shoe 348a relative to the carousel frame 344. The stop bar 502 is also provided between each of the arms 364a, 370a; 364b, 370b; 364c, 370c for preventing the rotational movement of the shoes 348a-348c relative to the carousel frame 344 when the carousel 334 is being rotated in the air. As the shoe 348a rotates to effect the bend, the retraction member 1808 becomes slack allowing the follower bar 406 to translate along its tracks 420, 422.

After the bend is completed, the shoe 348a is rotated by motor 228 in the opposite direction to release the saddle 350a from engagement with the workpiece 22. When the shoe 348a is rotated in this opposite direction, any slack in the refraction member 1808 is taken up first and thereafter, the retraction member 1808 re-engages with the arc-shaped bearing surface 387. This pulls the follower bar 406 linearly in the reverse direction as the follower bar 406 travels along its tracks 420, 422. The length of the retraction member 1808 is set so when the shoe 348a is returned to its initial position for acceptance of a workpiece 22, the follower bar 406 is also at its initial position. The radius of the retraction member 1808 is selected to be great enough that the retraction member 1808 will not be put under increased tension during the bending process to keep it from breaking. The radius of the arc-shaped bearing surface 387 is therefore preferably at least as great as the neutral bending radius for the largest channel (e.g. channel 394d).

To form a subsequent bend in the workpiece 22, the clamping apparatus 20 is moved toward the shoe 348a until the portion of the workpiece 22 to be bent is positioned between the saddle 350a and the shoe 348a. The motor 116 is then operated to rotate the frame 110, the clamp assembly 24 and its mounted drive mechanism 26 and the attached workpiece 22 relative to the second mount 280 in either direction. The motor 116 can be used to rotate the clamp assembly 24 and its mounted drive mechanism 26 around 360 degrees. This allows the workpiece 22 to be positioned in a variety of rotational positions to allow for infinitely variable bending shapes. The bending operation is then repeated.

After the desired bends have been effected in the workpiece 22, drive mechanism 26 is actuated to release the workpiece 22. The workpiece 22 is removed from the bender 200. The bender 200 is then returned to its initial position and is ready to accept another workpiece. second embodiment of the follower assembly 1352a-1352c allows for a greater range of spacing between the follower bar 406 and the shoe 348a-348b than is provided for in the first embodiment of the follower assembly 352a-352c. This allows for a connection coupling 43 at the end of the workpiece 22 to be inserted between the follower bar 406 and the shoe 348a-348b. The connection coupling 43 has a larger diameter than the remainder of the workpiece 22. After the larger diameter connection coupling 43 is inserted past the saddle 350a-350c, the control device 25 operates to move the mount 1810 and the follower bar 406 toward the shoe 348a-348c to effect the squeeze on the smaller diameter workpiece 22.

Allowing placement of the follower bars 406 in different positions provides several operational advantages: 1) thinner wall workpieces 22 need the follower bar 406 to be positioned close to the shoe 348a-348c to create a higher compression force when bending to prevent wrinkling the workpiece 22; 2) the follower bar 406 needs to be positioned further away from the shoe 348a-348c when bending thicker wall workpieces 22 to reduce the forces created when bending; 3) when the shoe 348a-348c and follower bar 406 retract to the start position after a bend, the workpiece 22 is to remain stationary. The follower bar 406 must be retracted further to create enough clearance to prevent the workpiece 22 from binding with the shoe 348a-348c and the follower bar 406 and imparting excessive forces on the drives that hold the workpiece 22 in place; 4) when inserting a workpiece 22 with a connection coupling 43 on it, the follower bar 406 must be retracted even further to provide the clearance needed to fit the larger diameter connection coupling 43 into the shoe 348a-348c.

While the retraction member 1808 is described with regard to the second embodiment of the follower assembly 1352a-1352c, the retraction member 1808 can be used with the first embodiment of the follower assembly 352a-352c. When the retraction member 1808 is used with the first embodiment of the follower assembly 352a-352c, the motor 229 is disengaged to allow the roller 408 to freely rotate and allow the follower bar 408 to translate as described herein.

Figure 39:
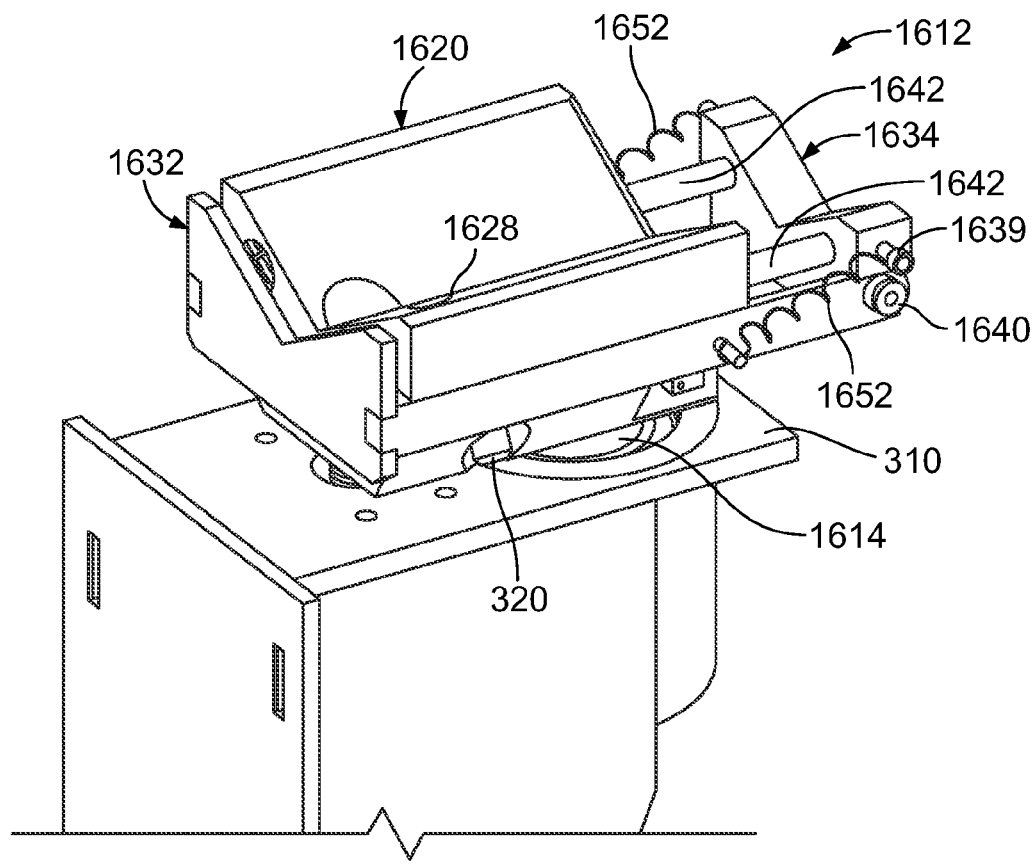
FIG. 39 is a perspective view of the seat of FIG. 37, in a second position.

FIG. 20 shows the first embodiment of the seat 312 and the sensor 320 which can be used with the automated bender 200. FIGS. 37-39 show the second embodiment of the seat 1612 into which the sensor 320 can be mounted, such seat 1612 being substituted for seat 312 as shown herein. In this second embodiment, the seat 1612 seats on top of the bracket 310, and an elongated tube 1614, identical to tube 314, extends from the lower surface of the seat 1612 and through the aperture 316 in the bracket 310. The second lift assembly 298 is used to raise and lower the seat 1612 toward/away from the top of the bracket 310 in the direction of arrows 292, see FIG. 4. As described herein, the actuating rod 308 can be lifted. When the actuating rod 308 is lifted high enough, the end of the actuating rod 308 engages the underside of the seat 1612 to move the seat 1612 upwardly relative to the mounting bracket 296 in the directions of arrows 292.

The seat 1612 is formed as a block 1620 having a first end 1620a, an opposite second end 1620b, side surfaces extending between the ends 1620a, 1620b, an upper end and a lower end. A pocket 1618, such as a V-shaped pocket, is formed in the upper end into which the workpiece 22 seats as described herein. Each side surface has an upper portion 1622a and a lower portion 1622b which is recessed from the upper portion 1622a and extends from the first end 1620a to the second end 1620b. A pair of spaced apart passageways 1624 extend through the seat 1612 from the first end 1620a to the second end 1620b. The ends of the passageways 1624 proximate to the first end 1620a of the seat 1612 have a counterbore 1626 therein. One lower portion 1622b has a recess 1623 proximate to the second end 1620b of the block 1620.

The sensor 320 is mounted in an aperture 1628 which has an open end in the pocket 1618. The sensor 320 is used to determine whether the workpiece 22 is seated on the seat 1612, and further may be used to determine when an end of the workpiece 22 is positioned proximate to the sensor 320.

A workpiece positioning assembly 1630 is attached to the seat 1612 and is used to accommodate the connection coupling 43 provided on the end of the workpiece 22. The workpiece positioning assembly 1630 generally includes a push plate 1632 pivotally connected to a support plate 1634 by a pair of arms 1636.

The push plate 1632 has a first end surface 1632a, an opposite second end surface 1632b, sides 1632c extending between the end surfaces 1632a, 1632b, an upper surface and a lower surface. A pocket 1636, such as a V-shaped pocket, is formed in the upper surface into which the workpiece 22 seats as described herein.

The support plate 1634 has a first end surface 1634a, an opposite second end surface 1634b, sides 1634c extending between the end surfaces, an upper surface and a lower surface. A pocket 1638, such as a V-shaped pocket, is formed in the upper surface into which the workpiece 22 seats as described herein. An upper pin 1639 extends outwardly from each side surface 1634c. A lower pin 1640 extends outwardly from each side surface 1634c, and is spaced from the respective upper pin 1639. A pair of spaced apart support rods 1642 extend from the first end surface 1634a. The support rods 1642 seat within the passageways 1624 in the block 1620 and the free ends of the support rods 1642 have a spring connection aperture 1644 therethrough.

A spring 1646 is mounted in each passageway 1624 and an end of each spring 1646 is anchored to the respective passageway 1624 by a pin 1648 which seats in the counterbore 1626. Other suitable means may be provided to anchor the ends of the springs 1646 to the passageways 1624. The opposite ends of the springs 1646 are attached to the spring connection apertures 1644 in the respective support rods 1642. Other suitable means may be provided to anchor the springs 1646 to the support rods 1642.

The block 1620 is between the plates 1632, 1634. The second end 1632b of the push plate 1632 is proximate to the first end 1620a of the block 1620. The first end 1634a of the support plate 1634 is proximate to the second end 1620b of the block 1620. The support rods 1642 enter into the block 1620 at the second end 1620b and the free ends connect with the springs 1646 within the passageways 1624. The springs 1646 are normally in a compressed condition.

The arms 1636 are affixed to the sides 1632c of the push plate 1632 and are pivotally connected to the sides 1634c of the support plate 1634 by the pins 1640. The arms 1636 seat within the lower recessed portions 1622b of the block 1620. A pin 1650 extends outwardly from each arm 1636. Springs 1652 are connected between the pins 1650, 1639 and are normally in a compressed condition.

A sensor 1654 is mounted on the block 1620 in the recess 1623 by suitable means. The sensor 1654 senses movement of the support plate 1634 relative to the block 1620. The sensor 1654 is in communication with the control device 25 and can be embodied as any of a variety of sensors capable of detecting presence and/or proximity of a workpiece 22, such as by way of non-limiting example, a laser sensor, a photoelectric sensor or a proximity sensor.

With this second embodiment of the seat 1612, the end of the workpiece 22 is determined regardless of whether the connection coupling 43 is installed on the end of the workpiece 22. This enables the accurate positioning of the workpiece 22 so the bends are made in the correct locations.

When the workpiece 22 is placed onto the seat 1612, the end of the workpiece 22 to be fed into the shoe assemblies 346a-346c is placed on the block 1618. When the workpiece 22 is positioned on the pockets 1636, 1618, 1638 of the push plate 1632, the block 1620 and the support plate 1634, the connection coupling 43 is seated in front of the push plate 1632 such that the rear end of the connection coupling 43 abuts against the first end surface 1632a of the push plate 1632. The sensor 320 senses whether the workpiece 22 is present and communicates this information to the control device 25.

As described herein, the clamping apparatus 20 then pulls the workpiece 22 away from the shoe assemblies 346a-346c. If a connection coupling 43 is not on the end of the workpiece 22, the clamping apparatus 20 is used to continue to pull the workpiece 22 back until the sensor 320 senses the end of the workpiece 22. If a connection coupling 43 is mounted on the end of the workpiece 22, the clamping apparatus 20 is used to pull the workpiece 22 back until the larger diameter connection coupling 43 contacts the push plate 1632 and pushes the push plate 1632 towards the first end 1620a of the block 1620, which also moves the attached arms 1636 and moves the support plate 1634 away from the second end 1620b of the block 1620 to the position shown in FIG. 39. The sensor 1654 detects the movement of the support plate 1634 and communicates to the control device 25 that a connection coupling 43 is on the end of the workpiece 22. The end of the workpiece 22 is then determined by the control device 25, such as based on the known standard nominal length of the end of the workpiece 22 and the known position of a bump plate that the other end of the workpiece 22 is set against, or based upon factory set depths known as to where the connection coupling 43 is threaded onto the workpiece 22. As the workpiece 22 is moved towards the shoe assemblies 346a-346c by the clamping apparatus 20, the springs 1646 return the push plate 1632, the arms 1636 and the support plate 1634 to their original position as shown in FIG. 37.

When the workpiece 22 is initially set in the block 1620, it is possible that the workpiece 22 could be set down unevenly. If the workpiece 22 is set down unevenly, the push plate 1632 and the arms 1636 pivots about the pins 640 to avoid damage to the block 1620. After the workpiece 22 is level, the springs 1652 return the push plate 1632 and the arms 1636 to the original position shown in FIG. 37.

As a result of the structure of the clamp assembly 24, 24', a large variety of diameters of workpieces 22 can be clamped by the clamp assembly 24, 24' without having to change any parts of the clamp assembly 24, 24'. As discussed above, workpieces 22 used with the clamp assembly 24, 24' may have an outer diameter between 0.5" and 7". This provides for a "zero change-over" in the clamp assembly 24, 24'.

The automated bender 200 allows for the fabrication of workpieces based upon data that is automatically extracted from architectural drawing models using application 901. The architectural drawing models may, for example, include building information modeling (BIM) drawings. The BIM drawings may be produced by software used by architects, structural engineers, mechanical, electrical and plumbing (MEP) engineers, designers and contractors, etc. Example types of BIM software include AUTODESK REVIT, BENTLY and other BIM applications.

For the sake of simplicity the data extraction application is described as the application 901, however add-on, stand-alone and other types of applications may also be used to determine the data described herein. The extraction applications may be implemented by software, firmware, hardware or a combination thereof. The application 901 may be added, for example, as an AUTODESK REVIT ribbon (see e.g., 901 of FIG. 42). The application 901 determines the data that is used by the automated bender 200, or other bender, to construct workpieces 22 with the appropriate bends in accordance with the BIM drawings. The data from the application 901 may be used for various types of bending including hand benders, electrical benders and hydraulic benders. While FIGS. 1 and 3-39 show embodiments of a suitable automated bender 200, it is to be understood that the embodiments of the systems and methods are not limiting. For example, another example automated bender is the 855GX manufactured by Greenlee Textron Inc.

Figure 40A:
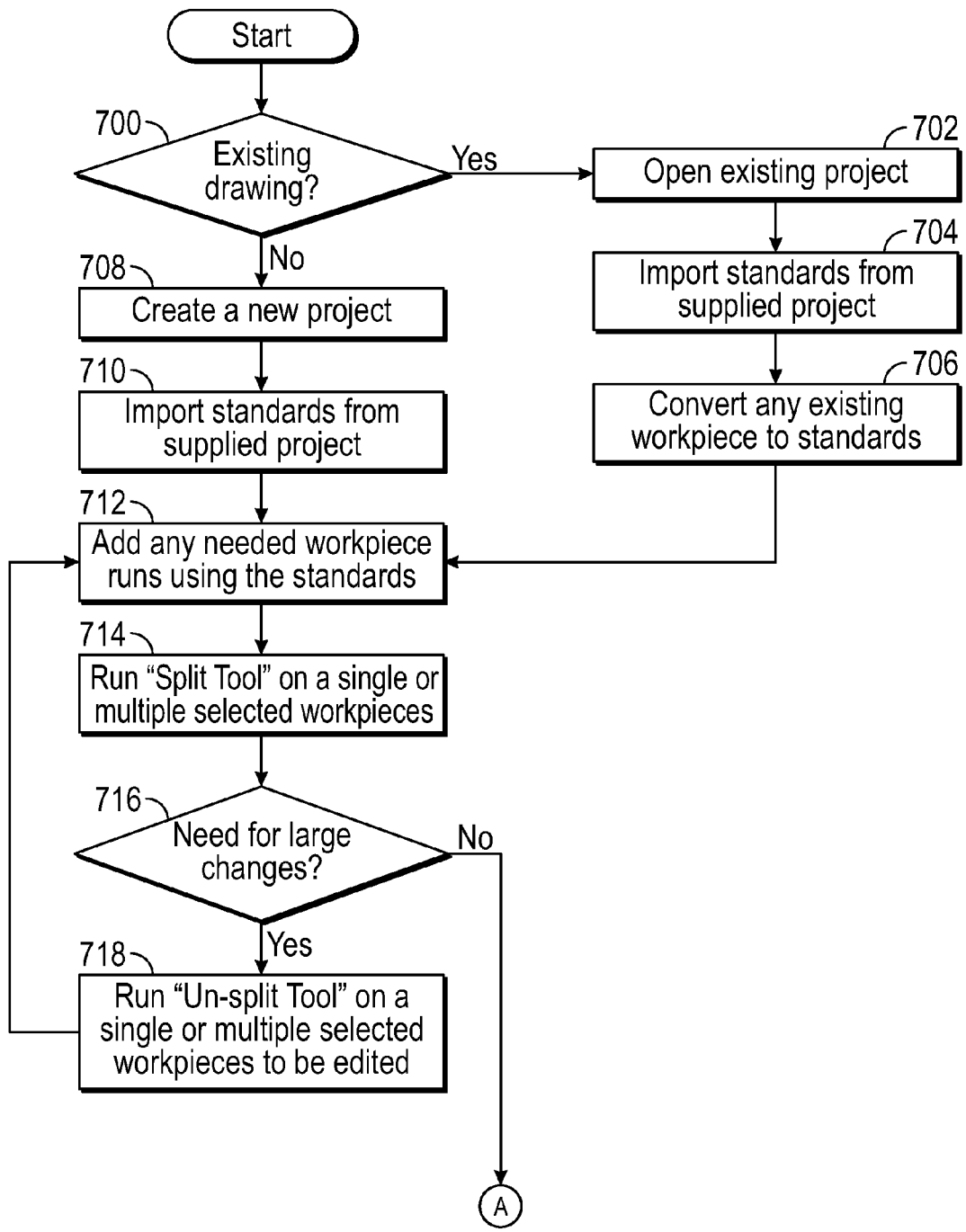
FIGS. 40A-40C are flowcharts of an example process for converting architectural drawings to data used for fabricating, including prefabricated, workpieces.
Figure 40B:
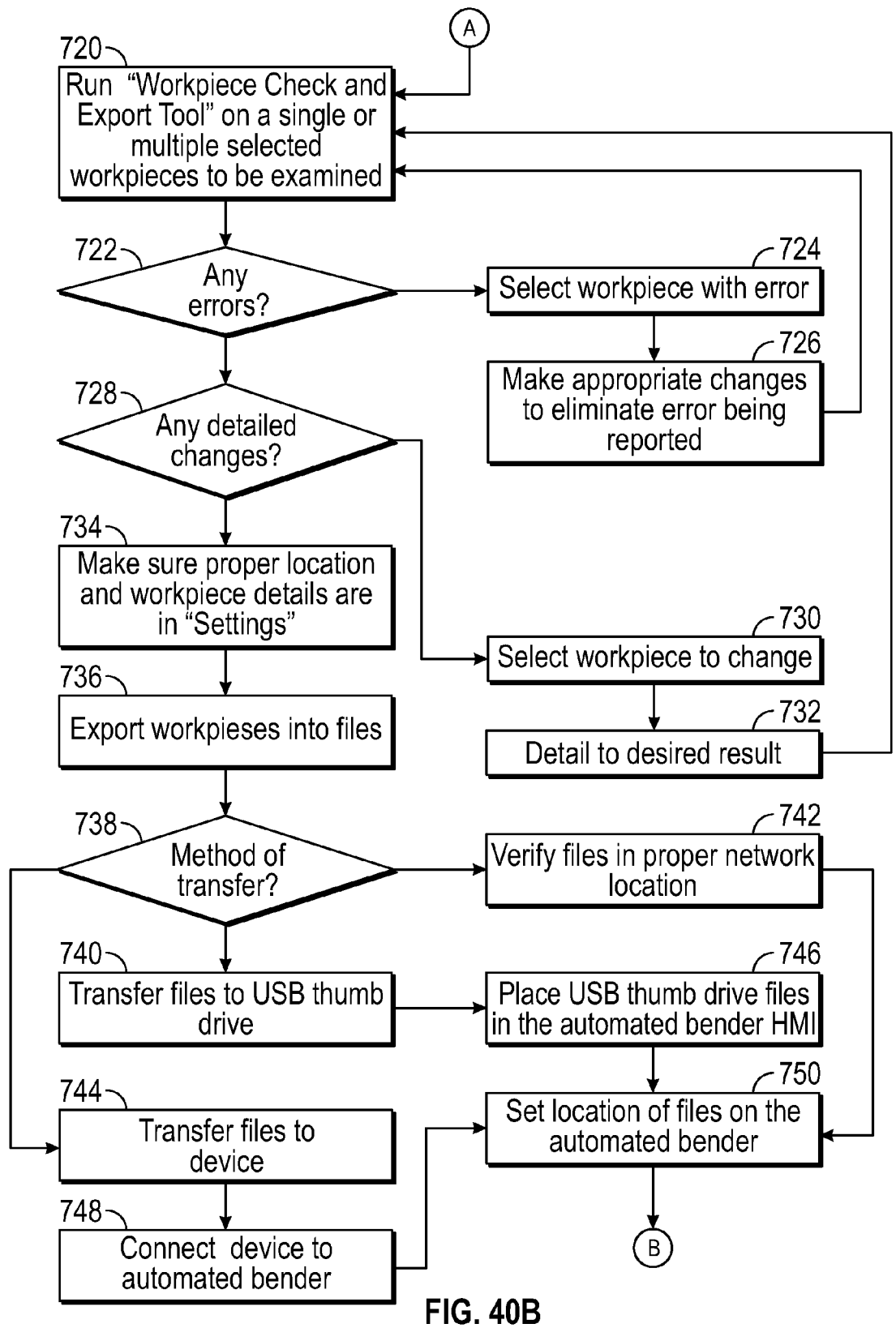
Figure 40C:
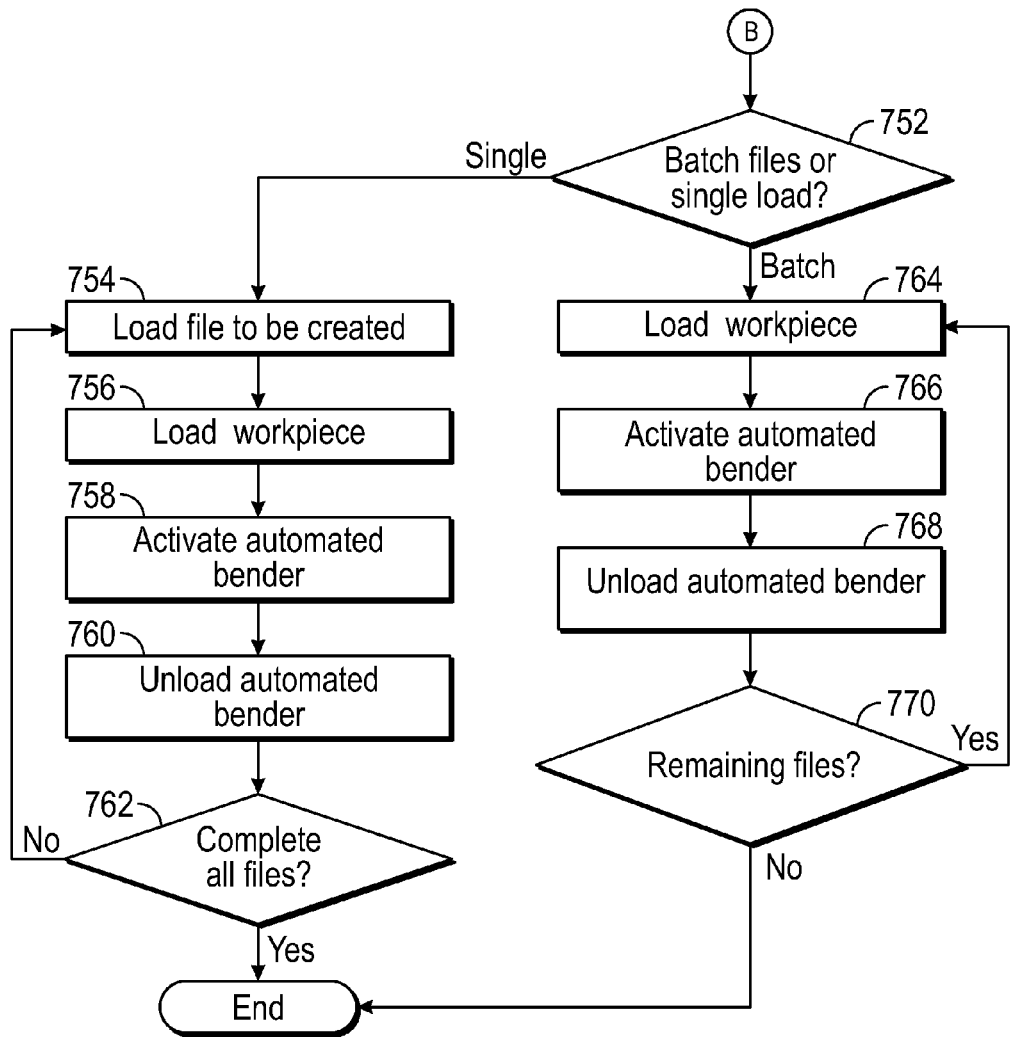

FIGS. 40A-40C are flowcharts of an example process for converting architectural drawings to data used for fabricating, including prefabricating, workpieces 22. The application 901 may be stored as code in memory, such as memory 27, and executed by a processor, such as processor 30, on a computer having the architectural software. The application 901 processes architectural drawings to determine data from the drawings needed by the automated bender 200 or other benders to create workpieces 22. The application 901 may be loaded onto the computer for executing with the architectural BIM drawing tool, e.g., AUTODESK REVIT, BENTLEY, etc. or may be stored separately, e.g., in the cloud. For existing drawings (700), the drawing project is opened in the BIM software (702) and a standard or set of standards for the workpieces 22 (generally referred to as standards) are imported from the application 901 (704). For example, Greenlee Textron Inc. has a set of workpiece bending standards which may be imported from the application 901. Other types of standards for standard organizations or manufacturers may be used. The application 901 converts existing workpiece runs in the drawings to match the standards (706), e.g., by replacing the size, types and/or bends of the existing workpieces 22 to match the standards. The standards include optimal bend radii for determined types of sizes of workpieces 22. The data determined by the application 901 for the conduit size, types and bends, etc. (see, e.g., FIG. 44) are sent to automated bender 200 and then used by the automated bender 200 to perform the bends using the shoes 348a-c of the shoe assembly 346a-c of the automated bender 200. Depending on an implementation, the application 901 may also provide for other types of standards that differ from the standards. If a new project drawing is being created (708), the application 901 imports the standards for use with the creation of the new drawing (710).

After the workpieces 22 are drawn or converted to the desired standard, any sections of the run that are missing, and any runs of workpieces 22 that are missing, are added to the drawings to make for continuous runs based on the standard (712). The runs include, for example, the number of workpieces 22, the size of the workpieces 22 and bends, etc. needed for the workpieces 22 to travel from point A to point B, for example, from one electrical box to another electrical box. The standards help ensure that the bends are drawn as accurately as possible using the BIM software and are not too close to an end of the workpiece 22, that the automated bender 200 may perform the bend, etc.

A split tool of the application 901 may be executed for a single or multiple workpieces 22 (714). The split tool divides a long run into sections based on a length of the workpieces 22 to be used, e.g., 10 foot or 20 foot lengths in most cases for conduit. A user of the software may select the lengths of the workpieces 22 to be used and select the start point of the splits. The split tool may start splitting the run from one end of the run, e.g., point A, to the other end of run, e.g., point B, or in an optimized way to try to make each workpiece 22 with a bend a determined length, e.g., 10', and select the straight section splits at a determined length, e.g., 20', to minimize the number of cut pieces. After executing the split tool, if the user wants to change the application's determined splits (716), the un-split tool may be executed for a single or multiple selected workpieces 22 to be edited (718).

The user may then initiate a workpiece check and export tool of the application 901 for single or multiple selected workpieces 22 to be examined (720). The application 901 determines whether there are any errors, e.g., whether the workpieces 22 meet the specifications for the standards that may be imported to the drawing application (722). Types of determined errors may include, for example, that the workpiece 22 cannot be physically bent the way it is drawn, that there is not enough space between a bend and an end of the workpiece 22 based on an orientation of the workpiece 22 being fed into the bender 200, that there is not enough clearance between bends in order to make the bends on the single workpiece 22, etc. The application 901 may output a table or other data structure (see e.g., FIG. 44), that lists the name of the workpiece 22, how many bends are in the workpiece 22, whether there were errors, the type of errors, etc. The output data structure may, for example, be formatted as a spreadsheet interpretable by a spreadsheet application, such as by way of non-limiting example, EXCEL by MICROSOFT, as a list of comma separated values, and/or other data structure capable of organizing the output data in a manner that may be interpreted by a computer application and/or by a human operator. The application 901 may select the workpieces 22 with errors (724) and the drawing may be modified, e.g., using the un-split tool described above, to correct the error being reported (726). After the modifications are made to the drawing, the workpiece check and export tool may be re-executed and the outputted table re-checked for errors (720).

After any errors are corrected, the application 901 checks for any detail changes (728). Detail changes include changing an orientation of the workpieces 22 to look ascetically pleasing, e.g., by having connection couplings of proximate workpieces 22 line up next to each other when the workpieces 22 are installed. The workpieces 22 with details to be changed are selected (730) and the details of the workpieces 22 are changed based on the users desired result (732). The workpiece check and export tool of the application 901 is re-executed and the outputted table re-checked for errors (720).

The application 901 includes a settings menu such as for setting details about the workpiece 22 including length of the workpiece 22, the number of bends for concentric or segmented bending, and for setting a location of where to export determined workpiece bending data. The user may set desired workpiece details and data export location in the settings menu (734). The data determined by the application 901 based on the architectural drawings may be exported in files (736) (see e.g., FIG. 44). One example file is a comma separated values (CSV), but other file formats may be used. The files may be transferred to on-board storage (e.g., a hard drive, flash memory, and/or other on-board storage) of the computer executing the application 901 and/or external memory (738), such as a universal serial bus (USB) flash memory device that may be inserted into the automated bender 200 or other automated bender such as the 855GX automated bender manufactured by Greenlee Textron Inc. (740). Additionally or alternatively, the data may be sent over a wireless and/or wired communications network, e.g., to a memory location accessible by the automated bender 200 (742). Additionally or alternatively, the data may be transferred by a wired or wireless capable device, e.g., a computer, a tablet, a smartphone, etc. (744). Additionally or alternatively, the data may be transferred via a cloud memory storage, etc. The USB device may be inserted in a USB slot of the user interface 25 (746). Additionally or alternatively, the wired or wireless capable device may connect with the automated bender 200 to communicate the data files via a wired, wireless or hybrid communication to the control device 25 of the automated bender 200 (748). Wired technologies include but are not limited to telephone networks, cable networks, fiber-optic communications, the Ethernet, etc. Wireless technologies include but are not limited to WiFi, BLUETOOTH, ZigBee, Z-wave, WirelessUSB, WirelessHD, Wireless HART, UWB, Wireless Regional Area Network (WRAN), near field communication (NFC), ISA100a, Radio Frequency Identification (RFID), Infrared (IR), ISM Band, Institute of Electrical and Electronics Engineers (IEEE) 802.15.4, ANT+, 6LoWPAN, Ultra Wideband, satellite networks, cellular networks, etc.

Figure 41:
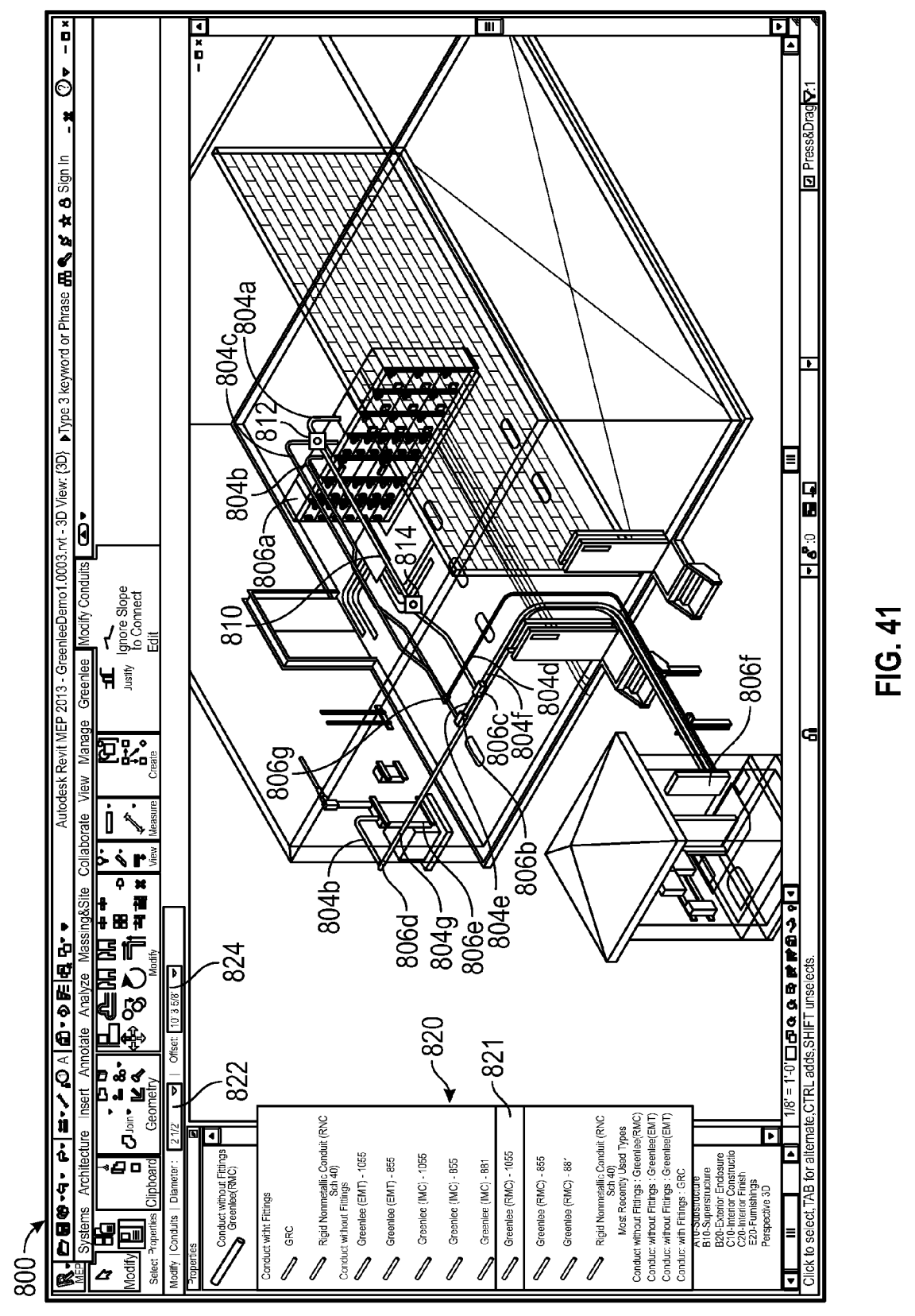

To describe in more detail where the data from the application 901 comes from, FIG. 41 is a screenshot 800 of an example BIM drawing for use with the application 901. The BIM drawing includes conduit runs 804a-h connected between electrical boxes 806a-g. Using the application 901 each conduit run 804*a-h* may be broken down to standard sized workpieces 22. Selected workpiece 810 is a user or application selected conduit section of the conduit run 804*a*. The selected workpiece 810 includes an identified start point 812 and endpoint 814. The application 901 also allows for selection of properties 820 of the selected workpiece 810. In this example, the Greenlee Textron Inc. RMC conduit standard is selected for bending on a Greenlee Textron Inc. 1055 automated bender 200 (821). Various types of workpieces 22, e.g., EMT, RMC and IMC conduit, may be selected as well as different automated benders to bend the workpieces 22, e.g., the Greenlee Textron Inc. model 855, 881 and 1055 benders. The diameter 822 of the conduit workpiece 810 is also be selected as is an offset 824, e.g., length of the selected workpiece 810.

Figure 42:
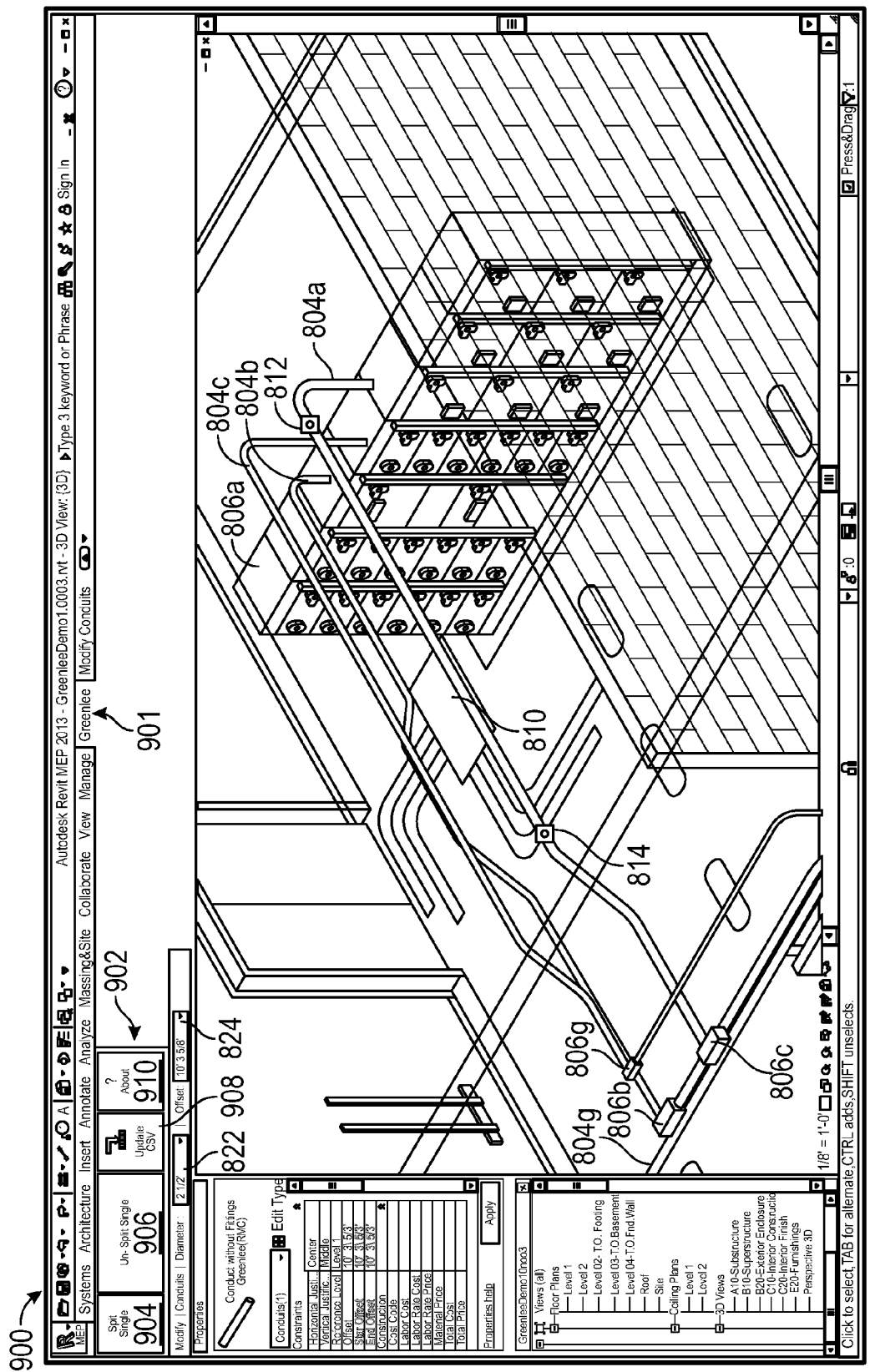
FIG. 42 is another screenshot of the example BIM drawing of FIG. 34.

FIG. 42 is another screenshot 900 of the example BIM drawing of FIG. 41. A link to the application 901 is displayed on a ribbon of the drawing application, such as an AUTODESK REVIT ribbon. When clicking the application 901 of the BIM drawing software, conduit run splitter options 902 are displayed to a user. The application 901 allows for single splits 904, single un-splitting 906, updating the CSV file 908, an information icon 910, and further options may include providing for multiple splits by type, multiple splits by selection, multiple un-splits, conduit check and export, setting, help, a select conduit tool for searching the BIM file and selecting conduit based on criteria such as size or type, etc. Once the conduit runs 804*a-h* are split into segments, the update CSV icon 908 may be used to update the data determined from the application 901 for the individual workpiece segments that were edited, e.g., based on the error checking described above (see e.g., 722 of FIG. 40B).

Figure 43:
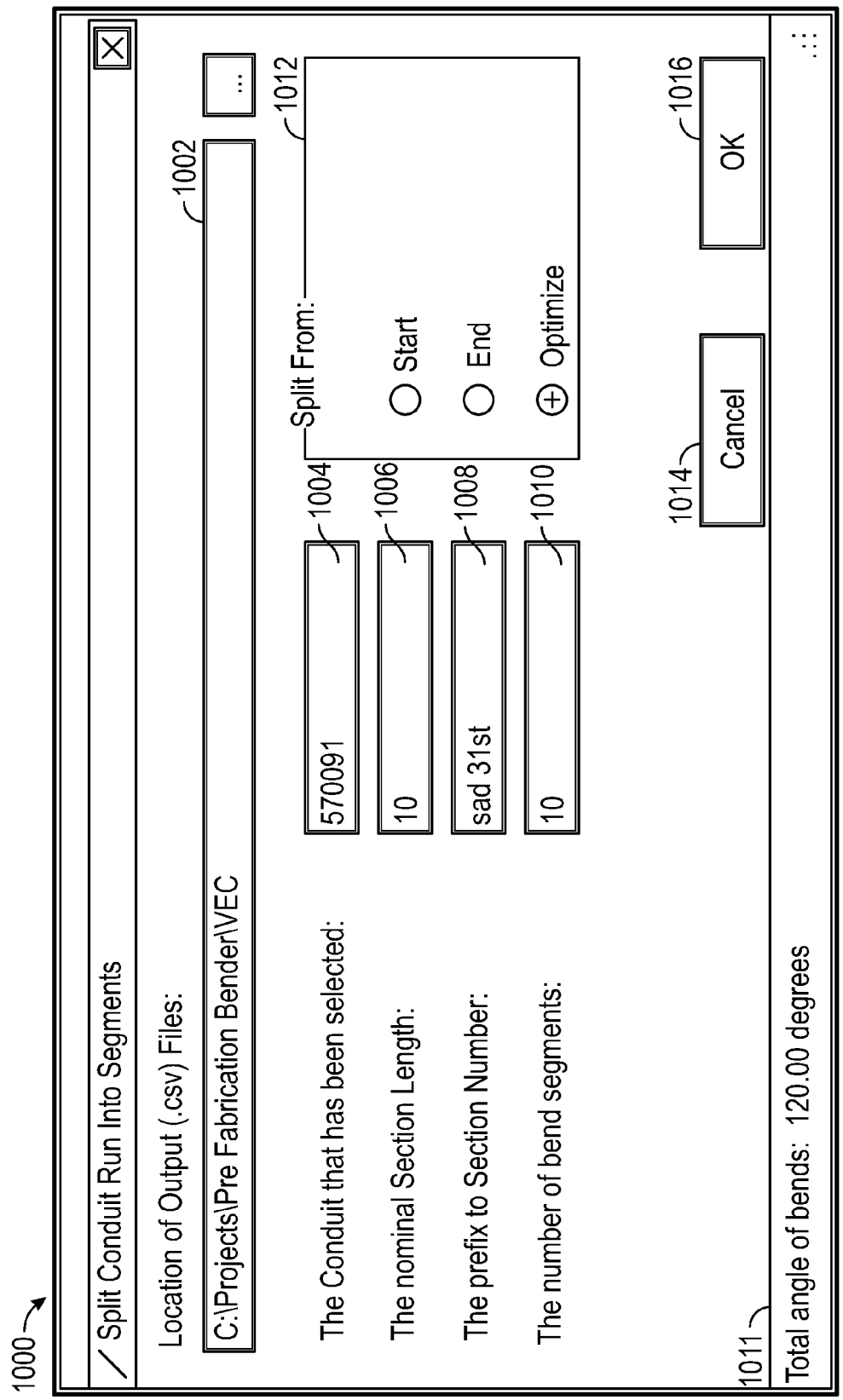
FIG. 43 is an example pop-up window that an application provides when splitting a conduit run.

FIG. 43 is an example pop-up window 1000 that the application 901 provides when splitting a conduit run 804*a-h* (e.g., 904 of FIG. 42). The pop-up window 1000 displays a storage location of the CSV file 1002, an identification number 1004 of the conduit workpiece 810 that the user has selected, a nominal section length 1006 of the conduit workpiece 810, a prefix to the section number 1008 and the number of selected bend segments 1010. The nominal section length 1006 of the conduit workpiece 810 is selected by a user, e.g., from about 1 foot to 20 feet in length. The conduit run, e.g., 804*a*, that is being split may be assigned a unique prefix to enable the conduit run to be uniquely identified. For example, in some embodiments, a user may specify prefix 1008 (e.g., sad3tst) to be added to the section number to uniquely identify the conduit run, e.g., 804*a*, that is being split. The number of bend segments 1010 is inputted for a custom bend radii. For example, if the user want a 90 degree bend with a 36" radius, the user selects a 36" radius in the BIM drawings and sets the bend segments, e.g., to 18 segments, to provide for eighteen 5 degree segments based on the 36" radius. The user may also select where to start the split 1012, e.g., from the start 812 of the selected workpiece 810, the end 814 of the selected workpiece 810, or to optimize to minimize a number of cut workpieces 22 for the conduit run 804*a*. The application 901 may display a total angle of bends 1011 based on the information inputted to the pop-up window 1000. The user may cancel 1014 the pop-up window inputs or click ok 1016 to accept the inputs.

FIG. 44 is a table of an example CSV output file 1100 including data as determined by the application 901. The output file 1100 may be outputted to a spreadsheet application, such as MICROSOFT EXCEL, or other application. The output file 1100 shows the version of the file format 1102 and units 1104, e.g., English or Metric. The application 901 outputs the bend type 1106, e.g., sequential (SEQUENT). Other bend types include but are not limited to concentric, stub up/kick(STUB), 3 bend saddle (SAD3), 4 bend saddle (SAD4), offset from start of bend(OFFSTART), offset from end of bend(OFFEND), u-shaped bend (UBEND) and three dimensional bend(3D). Architectural applications, e.g., AUTODESK REVIT utilize sequential and concentric bend types. For the other bend types, the height 1112, length 1114, angle 1116, straight 1118, h1 1120, h2 1122 and vangle 1124 data is outputted by the application 901. The bend type data is used in equations to set the marks for where the bends occur. For example, for a STUB bend type the user inputs the height 1112 and angle 1116 data used for that type of bend. The application 901 outputs the workpiece type 1108, e.g., EMT, RIG, IMC PVC, ALRIG and SSRIG, and the workpiece size 1110, e.g., 1" (written as 100) or other workpiece 22 sizes such as 0.5", 0.75", 1.25", 1.5", 2", 2.5", 3", 3.5", 4", 5", 6", etc., or whatever workpiece types and workpiece sizes are valid for the vendor.

The application 901 also outputs the workpiece number (pipe-num) 1126 including a user named job prefix, e.g., SEAN_0000, SEAN_0001 and SEAN_0002. The middle number, SEAN_0001, is the name of the workpiece 22 being bent, the first number, SEAN_0000, is the name of the connecting workpiece 22 that precedes the pipe being bent, and the third number, SEAN_0002, is the name of the connecting workpiece 22 that comes after the workpiece being bent. The workpiece numbers are used for labeling in the prefabrication environment so that installers may connect the workpieces 22 in the proper order. The sequential bend (seq_bend) parameter 1128 indicates the number of bends being made on the workpiece 22 being bent. The data l1_a1 1130, l2_a2 1132, l3_a3 1134, l4_a4 1136 and l5_a5 1138 indicate the distance of the start of the bend (l) and the angle (a) of the bend for sequential type bends. The sequential type bend data is determined and output by the application 901. The number of concentric bends in the angle (conc_bend) 1140, the angle of the concentric bend (conc_angle) 1142, the start position of the concentric bend (conc_start) 1144 and the overall radius achieved by the concentric bend (conc_radi) 1146 are determined and outputted by the application 901 as the data for concentric type bends. The PL_batch 1148 data output by the application 901 indicates the anticipated workpiece 22 length in the first column and whether or not the file has been process in the second column, e.g., 0 for an unprocessed file and 1 for a processed file. Therefore, as each file is processed the 0 may be changed to a 1 to flag the file as completed by the automated bender 200, or other automated bender, which may continue processing files until all of the files have been completed. If there is a need to bend based on the file another time, the user may select the file again and the number becomes incremented accordingly. Any number other than zero implies completion, but also lets the operator know if any files needed to be repeated.

The output file (e.g., an EXCEL file) and/or an application that may be used to read or otherwise access the output file may include a macro application to convert the output data to a format or visual picture that a user may read to bend the workpieces 22. As described above, the application 901 determines the data from architectural drawings and outputs the data as output files 1100, such as CSV files, to be used by the automated bender 200 to bend workpieces 22. This may provide accuracy and save a lot of time and money over currently known methods.

Referring again to FIGS. 40A-40C, the control device 25 of the automated bender 200 or other bender interface allows the user to set a location of the bend file or files storage so that the automated bender 200 or other bender may find the files to use data determined from the application 901 for bending (750). For example, the control device 25 allows the user to identify a network location of the data file or files. If multiple files are stored at the location, the automated bender 200 may obtain and work through all the files one-by-one. For example, the automated bender 200 may work through a series of files corresponding to such the workpieces 22 to be used for a particular job construction site or subsection of the job site. When an autoloader is used together with the automated bender 200, all of the workpieces 22 may be loaded into the autoloader and the automated bender 200 may receive the workpieces 22 one-by-one from the autoloader to bend the workpieces 22 based on the data in the files, without the need for each workpiece 22 to be individually loaded into the automated bender 200 by a user. All or some of the workpieces 22 may be loaded into the autoloader at the same time. When the autoloader runs out of workpieces 22, more workpieces 22 may be loaded into the autoloader. In some example embodiments, regardless of whether the workpieces 22 are individually loaded or batch loaded, the control device 25 may prompt the user regarding what type of workpiece 22 to load in the automated bender 200, when to place the workpiece 22 in the automated bender 200 and when the bending of the workpiece 22 is completed and the workpiece 22 is ready to be removed from the automated bender 200.

The control device 25 determines if the files containing the data for creating the bent workpieces 22 are for a batch or single load (752). For single files, the control device 25 loads the data from the file to the automated bender 200 (754). The proper workpiece size and type is loaded into the automated bender 200 (756). The automated bender 200 bends the workpiece 22 based on the data provided by the application 901 (758). The processor 30 of the control device 25 executes the programs stored in memory 27 with the data to perform the bends on the workpieces 22. The data provided by the application 901 for the input interface 25 includes the lengths and diameters of the workpieces 22 to be clamped by the clamping apparatus 20, the types of workpiece 22 (e.g., IMC conduit) and the types of bends to be made to the workpieces 22 (e.g., sequential) by the bending carousel apparatus 208. As a result of the controlled programming using the data from the application 901, the carousel frame 344 is lifted upwardly by the carousel lifting assembly 345 and rotated until the arm, for example arm 364a, containing the proper channel is positioned over the bending position. The carousel frame 344 is then lowered by carousel lifting assembly 345. The control device 25 is programmed by the data determined from the application 901 to control how far the workpiece 22 is to be lifted by the first and second assemblies 206a, 206b so that the workpiece 22 may be inserted into the clamping apparatus 20. The clamping apparatus 20 is then moved to effect entry of the end of the workpiece 22 into the clamping apparatus 20.

Next, the workpiece 22 is moved according to the data processed by the processor 30 to the aligned position with the channel, for example channel 394a, that has been designated in the bending carousel apparatus 208 (channel 394a is used in the following description, but it is to be understood that it is only illustrative). The workpiece 22 is introduced into the corresponding channel 418a of the follower bar 406 by moving the clamping apparatus 20 toward the shoe assembly 346a. The workpiece 22 then travels along the channel 418a of the follower bar 406 and travels between the channel 418a in the follower bar 406 and the channel 394a in the shoe 348a. The workpiece 22 advances along the channels 418a, 384a until the workpiece 22 passes between the shoulder 396a and the saddle 350a. Once the control device 25 has determined based on the data that the workpiece 22 has been advanced to the position where the bend is to be effected, the lift assembly 206a then drops out of position and returns back to where it started. The shoe 348a starts to rotate and the saddle 350a engages with the workpiece 22. As the shoe 348a continues to rotate, the follower bar 406 translates linearly and "squeezes" the workpiece 22 between the shoe 348a and the follower 406. It is to be noted that the squeeze is effected with workpieces 22 that are formed of thin wall conduit, tube and pipe. This creates the desired bend in the workpiece 22.

After the bend is completed, the shoe 348a is rotated in the opposite direction to release the saddle 350a from engagement with the workpiece 22. The follower bar 406 also translates linearly in the reverse direction. To form a subsequent bend in the workpiece 22, the clamping apparatus 20 is moved toward the shoe 348a until the portion of the workpiece 22 to be bent is positioned based on the data between the saddle 350a and the shoe 348a. The motor 116 is then operated to rotate the frame 110, the clamp assembly 24 and its mounted drive mechanism 26 and the attached workpiece 22 in either direction. The motor 116 may be used to rotate the clamp assembly 24 and its mounted drive mechanism 26 around 360 degrees. This allows the workpiece 22 to be positioned in a variety of rotational positions to allow for infinitely variable bending shapes. The bending operation is then repeated.

After the desired bends have been effected in the workpiece 22, drive mechanism 26 is actuated to release the workpiece 22. The workpiece 22 is removed from the bender 200 (760). The bender 200 is then returned to its initial position and is ready to accept another workpiece 22. The control device 25 determines if all the files for workpieces to be bent have been completed (762). If not, data from a next file to be completed is loaded to the automated bender 200 (754).

If the files are being processed as a batch of files, then the sizes and types of workpieces 22 for those files are loaded into the automated bender 200. The loaded workpieces 22 are shaped based on the data in the batch of files (764). For example, all or a portion of the workpieces 22 for a job site are loaded at once to an auto-loader. The control device 25 may point to a directory containing the batch of files, either stored locally in memory 27 of the control device 25 and/or stored remotely. The automated bender 200 is activated to shape the workpieces 22 based on the data in the files (766). The shaped workpieces 22 are unloaded from the automated bender 200 after the bends are completed (768). After the workpieces 22 are shaped based on the batch of files, the automated bender 200 may determine if there are any more files remaining to be processed (770). A flag may be set in the file once it is processed so that the automated bender 200 may determine which files, if any, remain to be processed (see e.g., 1148 in FIG. 44).

The automated bender 200 may include a labeler such that the workpieces 22 may be labeled for assembling the shaped workpieces 22 in the correct locations and order at a jobsite. The label may include assembly information, e.g., a unique identifier for the workpiece 22 as well as the identity of the workpieces 22 it attaches to on both ends. The label may be applied in several ways and at one or more of several different locations on the automated bender 200. The labeler may be mounted before or after the bending carousel apparatus 208. For example, the label may be applied before and/or after completion of the bends, and/or after and/or before the workpiece 22 is removed from the automated bender 200. In one example the label is applied by laser or thermal printing, or as a decal, e.g., as a barcode by a barcode printer, such as a barcode printer available from ZEBRA located on the automated bender 200. In another example, the label includes an RFID tag encoded and printed by ZEBRA RFID printer models. The label printing may be triggered when the control device 25 is activated to unload the automated bender 200 upon completion of the bends (blocks 760 or 768). Additionally or alternatively, an inkjet printer head, etcher or ball pen may apply a label directly to the workpieces 22 as the workpieces 22 are loaded into the automated bender 200 (blocks 756 or 764).

While it is described that the data inputted to the automated bender 200 may be based at least in part from architectural drawings as determined by a processor, it should be appreciated that the data to be input may be determined in other ways. For example, data where the bends are located may be input by a user after taking measurements.

While particular embodiments are illustrated in and described with respect to the drawings, it is envisioned that those skilled in the art may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure and the appended claims.

What is claimed is:

1. A bender comprising:
a rotatable carousel plate having a first side defining a first surface and a second opposite side defining a second surface, the carousel plate being rotatable around a rotational axis; and
at least two bending shoes extending outwardly from the first surface of the carousel plate, each bending shoe having a plurality of channels therein configured to receive a workpiece, each bending shoe being rotationally attached to the carousel plate along a rotational axis, the rotational axes of the bending shoes being spaced apart from each other on the carousel plate and spaced apart from the rotational axis of the carousel plate, the rotational axes of the bending shoes and the carousel plate being parallel to each other, each bending shoe being rotatable around its rotational axis independently of the other bending shoes.

2. A bender comprising:
a carousel plate having a first side and a second opposite side;
at least two bending shoes attached to the first side of the carousel plate, each bending shoe having a plurality of channels therein configured to receive a workpiece, each bending shoe being rotatable relative to the carousel plate, each bending shoe being rotatable independently of the other bending shoes;
a mounting frame upon which the carousel plate is rotatably mounted; and
a motor attached to the mounting frame,
wherein when the carousel plate is rotated, one of the bending shoes engages with the motor.

3. The bender of claim 2, further comprising a second motor attached to the mounting frame, wherein the carousel plate can be lifted relative to the mounting frame by the second motor.

4. The bender of claim 1, wherein the carousel plate is mounted on a vertical pivot, and the channels of the bending shoes are horizontal.

5. The bender of claim 1, further comprising a clamping apparatus which is configured to receive the workpiece, the clamping apparatus being movable relative to the carousel plate.

6. The bender of claim 5, further including a mounting frame, and wherein the carousel plate and the clamping apparatus are mounted on the mounting frame, the carousel plate being rotatable relative to the mounting frame and the clamping apparatus being movable relative to the mounting frame.

7. The bender of claim 1, wherein at least three bending shoes are provided.

8. The bender of claim 1, further comprising a labeler mounted by the carousel, the labeler configured to add a label to the workpiece, the label including information for assembling the workpiece in a correct location at a jobsite.

9. A bender comprising:
a carousel plate having a first side and a second opposite side;
at least two bending shoes attached to the first side of the carousel plate, each bending shoe having a plurality of channels therein configured to receive a workpiece, each bending shoe being rotatable relative to the carousel plate, each bending shoe being rotatable independently of the other bending shoes; and
a follower bar attached to the carousel plate and movable relative to a first one of the bending shoes during a bending operation, the follower bar having a plurality of channels therein configured to receive the workpiece.

10. The bender of claim 9, further comprising a second follower bar attached to the carousel plate and movable relative to one of the bending shoes, the second follower bar having a plurality of channels therein configured to receive the workpiece.

11. The bender of claim 9, further comprising a roller attached to the carousel plate and engaged against the follower bar, the roller having an eccentric shaft extending therefrom, wherein rotation of the shaft causes the follower bar to translate toward or away from the first bending shoe.

12. The bender of claim 9, further comprising a roller attached to the carousel plate and engaged against the follower bar, the roller mounted on a mount capable of movement toward or away from the first bending shoe.

13. The bender of claim 12, wherein the mount has at least one drive member connected to the mount and to the carousel plate, the drive member configured to move the mount toward or away from the first bending shoe.

14. The bender of claim 9, further comprising a flexible member attached to the first bending shoe and the follower bar, wherein movement of the first bending shoe causes movement of the follower bar via movement of the flexible member.

15. The bender of claim 14, wherein the flexible member is a chain.

16. The bender of claim 9, wherein the follower bar is mounted on a mount which is capable of movement toward or away from the first bending shoe such that a space between the follower bar and the first bending shoe is increased or decreased.

17. A bender comprising:
a mounting frame,
a carousel plate rotatably mounted on the mounting frame, the carousel plate having a first side and a second opposite side;
at least two bending shoes attached to the first side of the carousel plate, each bending shoe having a plurality of channels therein configured to receive a workpiece, each bending shoe being rotatable relative to the carousel plate, each bending shoe being rotatable independently of the other bending shoes;
a clamping apparatus mounted on the mounting frame and configured to receive the workpiece, the clamping apparatus being movable relative to the carousel plate and relative to the mounting frame; and
a first seat configured to receive the workpiece, the first seat being positioned between the clamping apparatus and the carousel plate, the first seat is capable of movement relative to the clamping apparatus, and is capable of movement with the clamping apparatus.

18. The bender of claim 17, further comprising a second seat configured to receive the workpiece, the second seat being positioned between the clamping apparatus and the first seat, the second seat is capable of movement relative to the clamping apparatus.

19. The bender of claim 17, wherein the first seat has a sensor configured to sense the workpiece.

20. The bender of claim 19, wherein the first seat includes a block, a support plate attached to the block and movable relative thereto, a push plate pivotally attached to the support plate, the block being positioned between the support plate and the push plate, the push plate being capable of pivoting relative to the block.

21. The bender of claim 17, further comprising a first sensor on the block configured to sense the workpiece, and a second sensor on the block configured to sense movement of the support plate relative to the block.

22. A bender comprising:
a mounting frame;
a carousel plate rotatably mounted on the mounting frame, the carousel plate having a first side and a second opposite side; and
at least first and second bending shoes attached to the first side of the carousel plate, each bending shoe having a plurality of channels therein configured to receive a workpiece, each bending shoe being rotatable relative to the carousel plate, each bending shoe being rotatable independently of the other bending shoes;
a first follower bar attached to the first side of the carousel plate and movable relative to the first bending shoe, the first follower bar having a plurality of channels therein configured to receive the workpiece;
a second follower bar attached to the first side of the carousel plate and movable relative to the second bending shoe, the second follower bar having a plurality of channels therein configured to receive the workpiece; and
a motor attached to the mounting frame, wherein when the carousel plate is rotated, one of the bending shoes engages with the motor.

23. The bender of claim 22, further comprising a second motor attached to the mounting frame, wherein the carousel plate can be lifted relative to the mounting frame by the second motor.

24. The bender of claim 22, further comprising a clamping apparatus mounted on the mounting frame and which is configured to receive the workpiece, the clamping apparatus being movable relative to the mounting frame and to the carousel plate.

25. The bender of claim 22, further comprising a seat mounted on the mounting frame and which is configured to receive the workpiece, the seat being positioned between the clamping apparatus and the carousel plate, the seat is capable of movement relative to the clamping apparatus, and is capable of movement with the clamping apparatus, the seat has a sensor a configured to sense the workpiece.

26. The bender of claim 22, wherein the carousel plate is mounted on a vertical pivot, and the channels are horizontal.

27. A bender comprising:
a mounting frame;
a carousel plate rotatably mounted on the mounting frame, the carousel plate having a first side and a second opposite side;
first and second bending shoes attached to the first side of the carousel plate, each bending shoe having a plurality of channels therein configured to receive a workpiece, each bending shoe being rotatable relative to the carousel plate, each bending shoe being rotatable independently of the other bending shoes;
a first follower bar attached to the first side of the carousel plate and movable relative to the first bending shoe, the first follower bar having a plurality of channels therein configured to receive the workpiece;
a second follower bar attached to the first side of the carousel plate and movable relative to the second bending shoe, the second follower bar having a plurality of channels therein configured to receive the workpiece;
a clamping apparatus mounted on the mounting frame and which is configured to receive the workpiece, the clamping apparatus being movable relative to the mounting frame and to the carousel plate; and
a seat mounted on the mounting frame and which is configured to receive the workpiece, the seat being positioned between the clamping apparatus and the carousel plate, wherein the seat is capable of movement relative to the clamping apparatus, and is capable of movement with the clamping apparatus.

28. The bender of claim 27, wherein the carousel plate is mounted on a vertical pivot, and the channels of the bending shoes and the channels of the follower bars are horizontal.

* * * * *

UNITED STATES PATENT AND TRADEMARK OFFICE
CERTIFICATE OF CORRECTION

PATENT NO. : 9,849,494 B2  
APPLICATION NO. : 14/541541  
DATED : December 26, 2017  
INVENTOR(S) : Plummer et al.

Page 1 of 2

It is certified that error appears in the above-identified patent and that said Letters Patent is hereby corrected as shown below:

In the Drawings

In Fig. 42, Sheet 34 of 36, for Tag "904", in Line 1, delete "Spit" and insert -- Split --, therefor.

In Fig. 42, Sheet 34 of 36, delete " 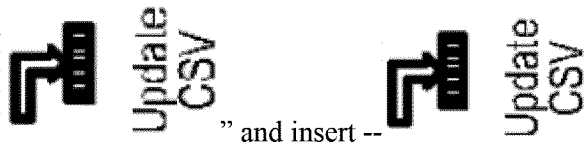 " and insert -- 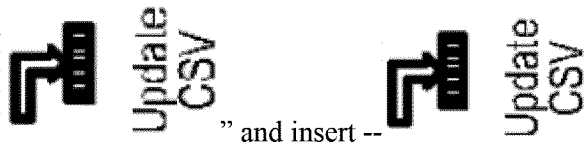 --, therefor.

In Fig. 42, Sheet 34 of 36, delete "Star" and insert -- Start --, therefor.

In Fig. 42, Sheet 34 of 36, delete "Sile" and insert -- Site --, therefor.

In the Specification

In Column 4, Line 44, delete "FIG. 34;" and insert -- FIG. 41; --, therefor.

In Column 7, Line 38, delete "carriage assembly 202" and insert -- carriage assembly 204 --, therefor.

In Column 8, Lines 32-33, delete "second mount 288," and insert -- second mount 280, --, therefor.

In Column 13, Line 61, delete "seat 212," and insert -- seat 312, --, therefor.

In Column 15, Line 57, delete "shaft 280" and insert -- shaft 380 --, therefor.

In Column 16, Lines 21-22, delete "lower plate 358." and insert -- lower plate 356. --, therefor.

In Column 18, Line 61, delete "apertures 234a-234c, The" and insert -- apertures 234a-234c. The --, therefor.

Signed and Sealed this  
Sixth Day of November, 2018

Andrei Iancu  
*Director of the United States Patent and Trademark Office*

CERTIFICATE OF CORRECTION (continued)
U.S. Pat. No. 9,849,494 B2

In Column 18, Line 66, delete "follower bar 416" and insert -- follower bar 406 --, therefor.

In Column 19, Line 41, delete "clamp assembly 44," and insert -- clamp assembly 24, --, therefor.

In Column 21, Line 4, delete "first lift assembly 296" and insert -- first lift assembly 295 --, therefor.

In Column 21, Line 38, delete "carousel 334" and insert -- carousel 344 --, therefor.

In Column 22, Lines 58-59, delete "base wall 1802" and insert -- base wall 1820 --, therefor.

In Column 22, Lines 62-63, delete "upper wall 1820." and insert -- upper wall 1822. --, therefor.

In Column 24, Line 62, delete "carousel 334" and insert -- carousel 344 --, therefor.

In Column 25, Line 3, delete "refraction member" and insert -- retraction member --, therefor.

In Column 25, Line 34, delete "workpiece. second" and insert -- workpiece. Second --, therefor.

In Column 26, Line 6, delete "follower bar 408" and insert -- follower bar 406 --, therefor.

In Column 27, Line 42, delete "block 1618." and insert -- block 1620. --, therefor.

In Column 32, Line 50, delete "a 1" and insert -- 1 --, therefor.

In the Claims

In Column 37, Line 7, in Claim 17, delete "frame," and insert -- frame; --, therefor.

In Column 37, Line 47, in Claim 22, delete "side; and" and insert -- side; --, therefor.

In Column 38, Line 23, in Claim 25, delete "sensor a" and insert -- sensor --, therefor.